United States Patent
Bridges et al.

(10) Patent No.: US 6,673,039 B1
(45) Date of Patent: Jan. 6, 2004

(54) COMPOSITIONS, KITS, METHODS, AND APPARATUS FOR TRANSVASCULAR DELIVERY OF A COMPOSITION TO AN EXTRAVASCULAR TISSUE OF A MAMMAL

(75) Inventors: Charles R. Bridges, Villanova, PA (US); Hansell H. Stedman, Ambler, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/597,890

(22) Filed: Jun. 19, 2000

Related U.S. Application Data

(63) Continuation of application No. PCT/US98/27072, filed on Dec. 18, 1998.
(60) Provisional application No. 60/068,317, filed on Dec. 19, 1997.

(51) Int. Cl.⁷ .................... A61M 29/00; A61M 37/00
(52) U.S. Cl. ............. 604/96.01; 604/6.16; 604/101.01; 604/101.03; 604/101.05
(58) Field of Search ................ 604/4.01, 5.01, 604/6.16, 96.01, 101.01–101.05, 103.04; 600/433–435

(56) References Cited

U.S. PATENT DOCUMENTS

| | | | | | |
|---|---|---|---|---|---|
| 4,366,819 | A | * | 1/1983 | Kaster ...................... | 606/153 |
| 4,824,436 | A | * | 4/1989 | Wolinsky .............. | 604/101.03 |
| 4,836,204 | A | * | 6/1989 | Landymore et al. ... | 604/101.05 |
| 5,314,409 | A | * | 5/1994 | Sarosiek et al. ....... | 604/101.03 |
| 5,384,128 | A | | 1/1995 | Meezan et al. | |
| 5,433,700 | A | | 7/1995 | Peters | |
| 5,478,309 | A | * | 12/1995 | Sweezer et al. ....... | 604/101.04 |
| 5,484,412 | A | * | 1/1996 | Pierpont ................ | 604/101.03 |
| 5,558,644 | A | * | 9/1996 | Boyd et al. ............ | 604/102.02 |
| 6,234,995 | B1 | * | 5/2001 | Peacock, III ............. | 604/96.01 |
| 6,254,563 | B1 | * | 7/2001 | Macoviak et al. ..... | 604/101.05 |
| 6,306,116 | B1 | * | 10/2001 | Hancock ..................... | 600/18 |

OTHER PUBLICATIONS

Acsadi et al., 1994, Hum. Molec. Genet. 3:579–584.
Acsadi et al., 1991, Nature 352:815–819.
Akhter et al., 1998, Science 280:574–577.
Boland et al., 1996, Pediatric Neurology 14:7–12.
Bönnemann et al., 1995, Nature Genetics 11:266–273.
Eyre, 1970, J. Pharm. Pharmacol. 22:104–109.
Ferrara et al., 1996, Nature 380:439–442.
Fisher et al., 1997, Nature Med. 3:306–312.
Graham et al., 1977, J. Gen. Virol. 36:59–74.
Greelish et al., 1999, Nature Medicine 5(4):439–443.
Helbling–Leclerc et al., 1995, Nature Genet. 11:216–215.
Jaynes et al., 1988, Mol. Cell. Biol. 8:62–70.
Koening et al., 1988, Cell 53:219–288.

(List continued on next page.)

*Primary Examiner*—Angela D. Sykes
*Assistant Examiner*—Leslie R Deak
(74) *Attorney, Agent, or Firm*—Duane Morris LLP

(57) ABSTRACT

Compositions, methods, kits, and apparatus are provided for delivering a macromolecular assembly such as a plasmid, virus vector, or other gene vector, to an extravascular tissue such as muscle tissue. The composition comprises the macromolecular assembly and a vascular permeability-enhancing agent. In another embodiment, the composition further comprises a vasodilating agent. The method of the invention comprises proving a vascular permeability-enhancing agent to a blood vessel and providing a macromolecular assembly to the vessel. An oxygenator useful for providing oxygen to a fluid extracorporeally prior to providing the fluid to a blood vessel of a mammal is included in the invention. Kits, apparatus, and methods for using the catheters described herein for isolating cardiac circulation, diverting caval blood flow from the right atrium, and for other purposes, are also described.

1 Claim, 24 Drawing Sheets

OTHER PUBLICATIONS

Kozarsky et al., 1993, Som. Cell Molec. Genet. 5:449–458.
Kozarsky et al., 1994, J. Biol. Chem. 268:13695–13702.
Kozarsky et al., 1996, Nature Genet. 13:54–62.
Krogh, 1919, J. Physiol. 52: 409–415.
Lim et al., 1995, Nature Genet.11:257–265.
Majno et al, 1961, J. Biophys. Biochem. Cytol. 11:571–604.
Nigro et al., 1997, Hum. Mol. Genet. 6:601–607.
Pappenheimer et al., 1951, Am. J. Physiol. 167:13–28.
Parker et al., 1997, Am. Heart J. 93(1):66–72 (Abstract only).
Piccolo et al., 1995, Neuromusc. Disord. 4:143–146.
Quantin et al., 1992, Proc. Natl. Acad. Sci. USA 89:2581–2584.
Ragot et al., 1993, Nature 361:647–650.
Raper et al., 1996 Pancreas 12:401–410.
Rippe et al., 1994, Physiol. Rev. 74:163–219.
Roberts et al., 1995, J. Cell Sci. 108:2369–2379.
Roberts et al., 1997, Cancer Res. 57:765–772.
Sanes et al., 1986, EMBO J. 5:3133–3142.
Schlenker et al., 1991, J. Appl. Physiol. 71:1655–1662.
Senger et al., 1990, Cancer Res. 50:1774–1778.
Silverman et al., 1988, J. Appl. Physiol. 64:210–217.
Smith et al., 1987, New Engl. J. Med. 316:1197–1205.
Starling, 1896, J. Physiol. 19:312–326.
Stedman et al., 1991, Nature 352:536–539.
Stewart et al. 1993, EMBO J. 12:2589–2599.
Thom et al., 1995, J. Clin. Oncol. 13:264–273.
Weinbaum et al., 1995 Symp. Soc. Exp. Biol. 49:323–345.
Wennmalm, 1994, J. Int. Med. 235:317–327.
Wilson, 1996, New Eng. J. Med. 334:1185–1187.
Yang et al., 1994, Nature Genet. 7:362–369.
Yeh et al., 1996, J. Virol. 70(1):559–565.

\* cited by examiner

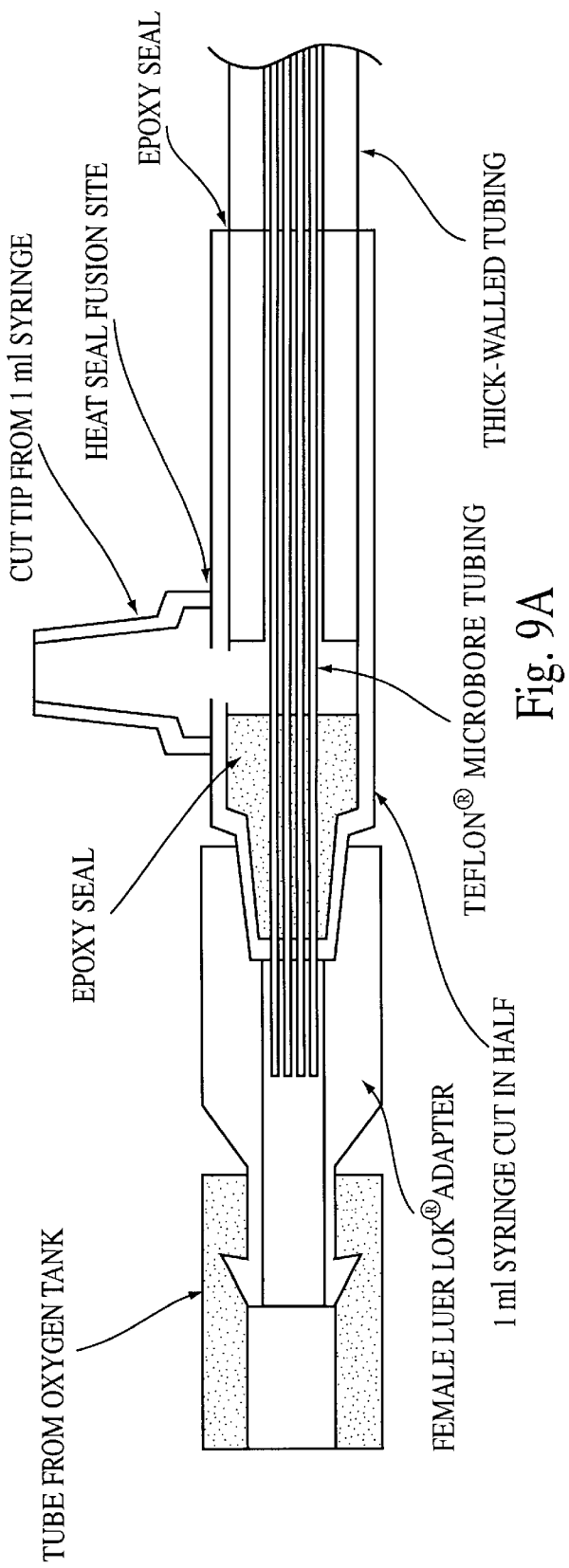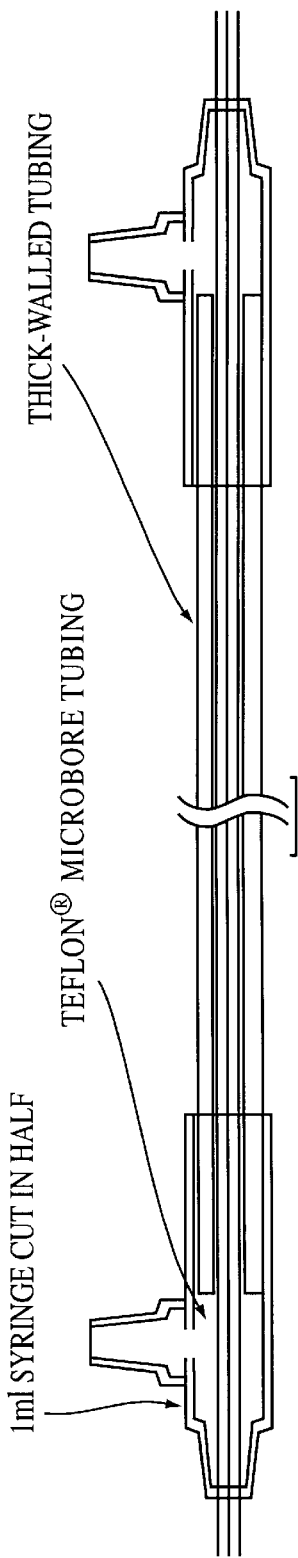
Fig. 9A
Fig. 9B

COMPOSITIONS, KITS, METHODS, AND APPARATUS FOR TRANSVASCULAR DELIVERY OF A COMPOSITION TO AN EXTRAVASCULAR TISSUE OF A MAMMAL

CROSS-REFERENCE TO RELATED APPLICATIONS

This application is a continuation of international patent application PCT/US98/27072, which was filed on Dec. 18, 1998, and is entitled to priority thereto pursuant to 35 U.S.C. §120 and is also entitled to priority pursuant to 35 U.S.C. §119(e) to U.S. provisional patent application No. 60/068,317, which was filed on Dec. 19, 1997.

BACKGROUND OF THE INVENTION

The field of the invention is gene therapy and cardiac therapy.

It is well known that viruses naturally deliver nucleic acids to cells and have therefore been exploited as gene delivery vehicles. However, in order for a recombinant virus to delivery a nucleic acid to a cell, the virus must first have access to the cell. Circulating virus in a mammal may not have ready access to cells to which it is desired that a nucleic acid be delivered. The present invention provides a means of providing to a virus access to cells to which it is desired that a nucleic acid be delivered.

The recent cloning of full length cDNAs for gene products implicated in several muscular dystrophies (Lim et al., 1995, Nature Genetics 11: 257–265; Piccolo et al., 1995, Nature Genetics, 10: 243–245; Nigro et al., 1996, Nature Genetics 14:195–198; Bonnemann et al., 1995, Nature Genetics 11: 266–273; and Helbling-Leclerc et al., 1995, Nature Genetics 11:216–218) has been paralleled by improvement in a variety of virus-based vector systems for use in somatic gene transfer (Yang et al., 1994, Nature Genetics 7:362–369; Yeh et al. 1996, J. Virology 70: 559–565; and Wilson, 1996, New Eng. J. Med. 334:1185–1187). The universal muscle involvement and resulting respiratory insufficiency in these diseases have focussed attention on the need for systemic vector delivery in vivo to mammal tissues and organs (Boland et al., 1996, Pediatric Neurology, 14: 7–12; Stedman et al., 1991, Nature 352: 536–539; Schlenker et al., 1991, J. Appl. Physiol. 71: 1655–1662; and Smith et al., 1987, New Engl. J. Med. 316: 1197–1205). Under physiologic conditions, the continuous endothelium of the skeletal muscle microvasculature is virtually impermeable to proteins larger than albumin (Stokes radius 3.5 nanometers; Berne et al., 1992, In: Physiology, Mosby, St. Louis), and the underlying basal lamina restricts the diffusion of larger macromolecular aggregates (Majno et al., 1961, J. Biophys. Biochem. Cytol. 11:571–597).

There is an acute need to develop compositions and methods which facilitate access of large macromolecules to muscle for the purposes of delivery of compounds which are of therapeutic benefit to mammals in need of such compounds. The present invention satisfies this need.

Muscular dystrophies and other myopathies are inherited, generally progressive disorders in which non-expression or abnormal expression of a muscular gene causes weakness, hypertrophy, and/or loss of normal muscular control. Many of these disorders have been associated with chromosomal mutations, although some (e.g. mitochondrial myopathies) are instead associated with deletions in mitochondrial DNA. For example, Duchenne muscular dystrophy (DMD) has been associated with mutations in the human gene encoding dystrophin protein.

Although respiratory compromise dominates the clinical course of end-stage DMD, underlying cardiomyopathy is universally present in such DMD patients. In some muscular dystrophies, including those involving dystrophinopathy (e.g. Becker muscular dystrophy) and those involving sarcoglycanopathy (e.g. limb-girdle muscular dystrophy), heart failure severe enough to require transplantation is sometimes observed (Piccolo et al., 1994, Neuromusc. Disord. 4:143–146; Fadic et al., 1996, N. Engl. J. Med. 334:362–366). In addition, at least a dozen other gene products have been implicated in the pathogenesis of recessively inherited dilated cardiomyopathy in humans (Fadic et al., 1996, N. Engl. J. Med. 334:362–366; Piccolo et al., 1995, Nature Genet. 10:243–245; Lim et al., 1995, Nature Genet. 11:257–265; Noguchi et al., 1995, Science 270:819–822; Nigro et al., 1996, Nature Genet. 14:195–198; Nigro et al., 1997, Hum. Mol. Genet. 6:601–607; Bione et al., 1994, Nature Genet. 8:323–327; Taroni et al., 1992, Proc. Nat. Acad. Sci. U.S.A. 89:8429–8433; Witt et al., 1992, J. Neurol. 239:302–306; Ho et al., 1994, Cell 77:869–880; Reichmann et al., 1991, Eur. Heart J. 12(Suppl. D):169–170; Eishi et al., 1985, Hum. Pathol. 16:193–197; Bione et al., 1996, Nature Genet. 12:385–389; Yokoyama et al., 1987, Br. Heart J. 57:296–299; Elleder et al., 1990, Virchows Arch. A Pathol. Anat. Histopathol. 417:449–455; Nagao et al., 1991, Clin. Genet. 39:233–237; Schultheiss et al., 1996, Mol. Cell Biochem. 163–164:319–327).

By way of example, common human cardiac diseases have been reproduced in mice in order to exploit the ability of germline gene transfer to achieve transgene expression in all cardiac myocytes. Two studies by others suggest the potential therapeutic benefit of transgenes expressed in the heart following somatic gene transfer in the adult mammal, provided that gene transfer occurs in a large majority of, or even all, cardiac myocytes. G protein mediated signaling pathways are targeted in both studies, addressing diseases as divergent as cardiac hypertrophy and dilated cardiomyopathy.

In the first study, cDNA encoding a peptide inhibitor of beta adrenergic receptor kinase 1 (bARK1) was expressed under the control of the cardiac muscle-specific alpha myosin heavy chain promoter (Rockman et al., 1998, Proc. Natl. Acad. Sci. USA 95:7000–7005). Breeding of transgenic mice integrating this construct with mice from a recently developed cardiomyopathic line (muscle LIM protein deficient {$MLP^{-/-}$}) led to the striking finding that the cardiomyopathy was prevented in the offspring. $MLP^{-/-}$ mice exhibit numerous abnormalities of cardiac myocyte structure and function that resemble those seen in a broad variety of human cardiomyopathies. The transgene-encoded inhibitor prevented these abnormalities through a general mechanism that is not directly coupled to normal functioning of the LIM protein This study indicates that delivery of a similar gene construct to human cardiac tissue could have significant therapeutic benefit for humans afflicted with a wide variety of cardiomyopathies, if only such a gene construct could specifically delivered to human cardiac myocytes with high efficiency.

In the second study, cDNA encoding a peptide inhibitor of binding between cardiac myocyte adrenergic receptors and a protein of the Gq subclass was expressed under the control of the cardiac muscle-specific alpha myosin heavy chain promoter (Akhter et al., 1998, Science 280:574–577). Transgenic mice integrating this construct were subjected to cardiac pressure overload by undergoing surgical transverse aortic constriction. Cardiac overexpression of this inhibitor greatly reduced the cardiac hypertrophic response to pressure overload. Several signal transduction pathways implicated in the human cardiopathological response to cardiac overload were demonstrated to be activated as a result of the surgical procedure. In the setting of strong signal activation, the reduction in cardiac hypertrophy associated with expression of the peptide inhibitor demonstrates that the inhibitor acts at a position common to multiple signal transduction cascades. This study also indicates that delivery of a similar gene construct to human cardiac tissue could have significant therapeutic benefit for humans afflicted with a wide variety of cardiomyopathies, if only such a gene construct could specifically delivered to human cardiac myocytes with high efficiency.

Other cardiac disorders (e.g. heart failure, myocardial infarction, rheumatic fever, arrhythmia, congestive heart failure, infective endocarditis, and pericarditis) are known to be associated with numerous non-congenital causes, but might nonetheless benefit from gene therapy methods if gene vectors comprising a nucleic acid encoding a beneficial gene product could be provided specifically and safely to cardiac tissue.

Unfortunately, the position of the heart within the human body has, in the past, required the use of highly invasive procedures for providing therapy directly and locally to cardiac tissue. In addition to the serious physiological complications which sometimes accompany such highly invasive procedures, these interventions may also exact a high psychological toll from patients who undergo them. These patients endure the physical trauma and long recovery periods associated with invasive cardiac procedures, and often emerge from recovery scarred, both physically and mentally.

Patients afflicted with cardiac and other myopathies are unable to benefit from many of the improvements being made to gene vectors, and from greater understanding of how their afflictions might be alleviated using gene therapy methods, because of a severe paucity of methods for performing local gene therapy in cardiac and other muscle tissues. The present invention provides local muscular gene therapy methods, compositions, kits, and apparatus which satisfy this critical need.

SUMMARY OF THE INVENTION

The invention relates to a cardiac isolation catheter which is insertable within the vena cava of a mammal. The catheter comprises (a) a hollow tubular body having a venous blood flow lumen extending longitudinally therein, a proximal end, a distal end, a proximal port, and a distal port;

(b) a distal vessel seat attached to the body; and (c) a proximal vessel seat attached to the body.

The catheter is positionable within the vena cava of the mammal such that one vessel seat is positioned in the superior vena cava of the mammal between the right atrium and the junction of the brachiocephalic veins and the other vessel seat is positioned in the inferior vena cava between the right atrium and the hepatic veins. The distal port is located distally with respect to the distal vessel seat. The proximal port is located proximally with respect to the proximal vessel seat. When the catheter is emplaced within the vena cava of the mammal, blood in the junction of the brachiocephalic veins and blood in the hepatic veins is in fluid communication with the venous blood flow lumen by way of the ports.

In one embodiment of the cardiac isolation catheter of the invention, at least one of the distal vessel seat and the proximal vessel seat comprises a raised surface extending circumferentially about the body. By way of example, the vessel seat may comprise a pair of closely-spaced raised surfaces, whereby the vena cava is securely seated at the vessel seat by ensnaring the vena cava between the pair of raised surfaces. Alternately, the vessel seat may comprise a pair of closely-spaced raised surfaces, and the body of the catheter may have a suction lumen extending longitudinally therein and communicating with a suction port situated between the pair of closely-spaced raised surfaces, whereby the vena cava is securely seated at the vessel seat by application of suction to the suction lumen.

In another embodiment, at least one of the distal vessel seat and the proximal vessel seat is expandable. The expandable vessel seat may comprise a balloon attached to the body and having an interior which communicates with an inflation lumen extending longitudinally in the body, whereby the vena cava may be securely seated at the vessel seat by expanding the balloon after positioning the catheter in the vena cava of the mammal. Both of the distal vessel seat and the proximal vessel seat may be balloons attached to the body and having interiors which communicate with the inflation lumen.

In a different embodiment of the cardiac isolation catheter of the invention, the body of the catheter has an access lumen extending longitudinally therein and an access port positioned between the distal vessel seat and the proximal vessel seat. The access port communicates with the access lumen. In this embodiment, the cardiac isolation catheter of claim 8, further comprises a second catheter having a distal end. The second catheter is positionable within the access lumen and can be urged through the access port. The distal end of the second catheter may comprise a curved portion for positioning the distal end of the second catheter within the pulmonary artery of the mammal. For example, the distal end of the second catheter may be adapted to the shape of a human heart. Alternately, or in addition, the distal end of the second catheter may have a deformable portion for positioning the distal end of the second catheter within the pulmonary artery of the mammal. The second catheter may be a wire-wrapped catheter, may comprise a pulmonary balloon at the distal end thereof, and/or may have a pressure relief lumen extending longitudinally therein and a right ventricle pressure relief port in fluid communication with the pressure relief lumen.

In still another embodiment, the cardiac isolation catheter of the invention has a fluid flow lumen extending longitudinally in the body thereof and a right atrium fluid access port located in the body between the distal vessel seat and the proximal vessel seat. The body may have a plurality of right atrium fluid access ports circumferentially arranged about the body.

The cardiac isolation catheter of the invention may further comprise at least one non-invasively detectable marker.

The invention also relates to a surgical kit comprising the cardiac isolation catheter of the invention.

The invention further relates to a kit for isolating the heart of a mammal from the rest of the circulatory system of the mammal. The kit comprises (a) cardiac isolation catheter of the invention having at least one access lumen extending therein from the proximal thereof;

(b) a second catheter insertable within the access lumen; and (c) an endoaortic catheter.

The second catheter has a distal portion and an inflation lumen extending longitudinally therein and comprises a balloon on the distal portion thereof. The interior of the balloon of the second catheter is in fluid communication with the inflation lumen of the second catheter. The endoaortic catheter comprises a flexible rod having a distal portion and a distal tip and an aortic vessel seat attached to the distal portion of the flexible rod. The aortic vessel seat may attached to the flexible rod at the distal tip thereof. In one embodiment, the flexible rod is hollow and has an expansion lumen extending longitudinally therein. In this embodiment, the aortic vessel seat comprises a balloon attached to the flexible rod and having an interior which communicates with the expansion lumen, whereby the aorta may be securely seated at the aortic vessel seat by expanding the balloon after positioning the distal portion of the endoaortic catheter in the aorta of the mammal. In another embodiment, the balloon is not located at the distal tip of the flexible body and the flexible body has a liquid access lumen extending longitudinally therein and a liquid access port located on the distal portion of the flexible body. The liquid access port is in fluid communication with the liquid access lumen and is located nearer the distal tip of the flexible body than is the balloon. In yet another embodiment of the kit, the second catheter has a fluid uptake lumen extending longitudinally therein and a fluid uptake port on the distal portion of the second catheter, wherein the fluid uptake port communicates with the fluid uptake lumen.

This kit may further comprise other components such as any one or more of the following:

(d) a cannula for insertion into a femoral artery of the mammal, the cannula having an arterial blood flow lumen extending longitudinally therein;

(e) a pump for withdrawing blood from the venous blood flow lumen of the cardiac isolation catheter and providing blood to the arterial blood flow lumen of the cannula;

(f) a blood oxygenator for oxygenating blood removed from the mammal; and (g) an azygous vein occluder, such as one selected from the group consisting of a hemostat, a cross clamp, a balloon catheter, and a tourniquet.

The kit may also comprise an inflammatory mediator selected from the group consisting of a vascular permeability-enhancing agent (e.g. histamine) and/or a vasodilating agent (e.g. papaverine).

The invention relates to a composition for delivering a macromolecular assembly to an extravascular tissue of an animal comprising the macromolecular assembly and a vascular permeability-enhancing agent. In one embodiment, the macromolecular assembly is a gene vector. In another embodiment, the vascular permeability-enhancing agent is selected from the group consisting of histamine, acetylcholine, an adenosine nucleotide, arachidonic acid, bradykinin, cyanide, endothelin, endotoxin, interleukin-2, ionophore A23187, nitroprusside, a leukotriene, an oxygen radical, phospholipase, platelet activating factor, protamine, serotonin, tumor necrosis factor, vascular endothelial growth factor, a venom, and a vasoactive amine, and is preferably histamine or vascular endothelial growth factor.

In another aspect of the invention, the composition comprises the macromolecular assembly a vascular permeability-enhancing agent, and a vasodilating agent. In one embodiment, the vasodilating agent is selected from the group consisting of papaverine, nimodipine, hydralazine, nitric oxide, epoprostenol, tolazoline, amrinone, milrinone, nitroglycerine, isosorbide dinitrate, isosorbide mononitrate, and an organic nitrate compound, and is preferably papaverine.

In yet another aspect of the invention, the composition comprises the macromolecular assembly a vascular permeability-enhancing agent, and an oxygen-transporting agent.

The invention also provides a kit for providing a macromolecular assembly to an extravascular tissue of an animal. The kit comprises a vascular permeability-enhancing agent and a vasodilating agent. In one embodiment, the kit further comprises the macromolecular assembly. In another embodiment, the macromolecular assembly is a gene vector comprising a human gene selected from the group consisting of a gene encoding dystrophin, a gene encoding eutrophin, a gene encoding a sarcoglycan, and a gene encoding a minidystrophin.

In yet another aspect, the kit comprises a vascular permeability-enhancing agent, a vasodilating agent, and an oxygen-transporting agent.

In a further aspect of the invention, the kit comprises a vascular permeability-enhancing agent, a vasodilating agent, and at least one disposable element of an extracorporeal circulatory support and oxygenation system. In one embodiment, the at least one disposable element is an oxygenator having a hollow body, a liquid inlet in fluid communication with the interior of the body, a liquid outlet in fluid communication with the interior of the body, a gas inlet for providing gas to the interior of a gas chamber, at least one gas-permeable membrane separating the gas chamber from the interior of the body, and a gas outlet for permitting gas to exit from the gas chamber, whereby gas exchange is enabled between a fluid in the interior of the body and a gas in the gas chamber. In another embodiment of the kit comprising an oxygenator, the body is a tube, the gas-permeable membrane comprises polytetrafluoroethylene (PTFE) tubing extending within at least a portion of the tube, and the gas chamber comprises the interior of the PTFE tubing.

The invention further relates to a method of delivering a macromolecular assembly to an extravascular tissue of an animal, preferably a human. The method comprises the steps of providing a vascular permeability-altering agent to a blood vessel associated with the tissue to increase the permeability of the endothelial layer of the vessel and providing the macromolecular assembly to the vessel, whereby the assembly is delivered to the tissue through the endothelial layer of the vessel. In one embodiment of the method, the macromolecular assembly is a gene vector, preferably an adenoviral gene vector. The gene vector preferably comprises a human gene, such as a gene selected from the group consisting of a gene encoding human dystrophin, a gene encoding eutrophin, a gene encoding a sarcoglycan, and a gene encoding a minidystrophin. In another embodiment, the gene vector comprises a promoter/regulatory region operably linked to the human gene, wherein the promoter/enhancer region is selected from the group consisting of a human skeletal muscle creatine phosphokinase promoter/regulatory region, a murine skeletal muscle creatine phosphokinase promoter/regulatory region, a promoter/regulatory region of a gene which is ordinarily expressed in a human skeletal muscle cell, and a human constitutive promoter region.

In another aspect of the invention, the method further comprises the step of providing a vasodilating agent to the vessel.

In another aspect of the invention, the tissue to which the macromolecular assembly is delivered is muscle tissue, preferably striated muscle tissue.

In yet another aspect, the method further comprises the step of increasing the perfusion pressure within the vessel above the normal physiological perfusion pressure after providing the macromolecular assembly to the vessel.

In still another aspect, the method further comprises the step of isolating the vessel from the blood circulatory system of the animal prior to providing the macromolecular assembly to the vessel. In one embodiment, the step of isolating the vessel from the blood circulatory system of the animal is performed prior to providing the vascular permeability-enhancing agent to the vessel. In another embodiment, the method further comprises the step of providing a clearance solution to the vessel after providing the macromolecular assembly to the vessel, the clearance solution being substantially free of the vascular permeability-enhancing agent.

In another aspect, the method further comprises the step of providing an oxygen-transporting agent to the vessel after isolating the vessel from the blood circulatory system.

In yet another aspect, the method further comprises the step of subjecting the animal to extracorporeal circulatory support and oxygenation prior to providing the vascular permeability-enhancing agent.

In still another aspect, the method further comprises the step of occluding the blood supply to the liver of the animal prior to providing the macromolecular assembly.

The invention also relates to a method of delivering a gene vector to an extravascular tissue of an animal, the method comprising the steps of
 a) isolating a blood vessel associated with the tissue from the blood circulatory system of the animal;
 b) thereafter providing a vasodilating agent to the vessel;
 c) thereafter providing a vascular permeability-enhancing agent to the vessel to increase the permeability of the endothelial layer of the vessel;
  providing the gene vector to the vessel, whereby the vector is delivered to the tissue through the endothelial layer of the vessel;
  increasing the perfusion pressure within the vessel above the normal physiological perfusion pressure; and
  providing an oxygen-transporting agent to the vessel; and
 d) thereafter providing a clearance solution to the vessel, the clearance solution being substantially free of the vascular permeability-enhancing agent.

The invention further relates to a method of providing a gene vector to substantially all muscle tissues of an animal, the method comprising the steps of
 a) subjecting the animal to extracorporeal circulatory support and oxygenation;
 b) thereafter providing a vasodilating agent to the blood circulatory system of the animal;
  providing a vascular permeability-enhancing agent to the blood circulatory system to increase the permeability of the endothelial layer of the vessels of the blood circulatory system;
  providing the gene vector to the blood circulatory system, whereby the vector is delivered to substantially all muscle tissues through the endothelial layer of the vessels of the blood circulatory system; and
  increasing the perfusion pressure within the vessel above the normal physiological perfusion pressure.

The invention further relates to a therapeutic gene vector for treating a human afflicted with muscular dystrophy. The therapeutic gene vector comprising a nucleic acid which comprises a promoter operably linked with the coding region of a human gene selected from the group consisting of a dystrophin gene, a eutrophin gene, a sarcoglycan gene, and a minidystrophin gene.

The invention also relates to a caval blood uptake kit. This kit comprises a catheter and a pair of vessel seats attached thereto. The catheter has a pair of venous blood uptake ports in communication with a venous blood flow lumen extending longitudinally within the catheter from the venous blood uptake ports to a proximal portion of the catheter. The catheter is insertable within the vena cava of a mammal. In one embodiment of the kit, the catheter is the cardiac isolation catheter of the invention. In another embodiment, the catheter has a notch in the exterior surface thereof, wherein the notch is adapted to fit the body of a second catheter. In yet another embodiment, the kit further comprises an azygous vein occluder.

The invention also includes another caval blood uptake kit. This kit comprising a pair of catheters. Each catheter has a vessel seat attached thereto and a venous blood uptake ports in communication with a venous blood flow lumen extending longitudinally therein from the venous blood uptake port to a proximal portion of the catheter. Each catheter is insertable within the vena cava of a mammal. In one embodiment, at least one of the catheters has a notch on the outer surface thereof, wherein the notch is adapted to fit the body of a second catheter. The kit may further comprise an azygous vein occluder.

The invention further relates to a method of diverting venous blood flow from the vena cavae of a mammal. This method comprising emplacing a cardiac isolation catheter of the invention within the vena cavae of the mammal. In one embodiment of this method, the venous blood flow lumen of the catheter is in fluid communication with an extracorporeal oxygenating device.

The invention still further relates to a method of diverting venous blood flow from the vena cavae of a mammal, the method comprising emplacing a superior caval return catheter within the superior vena cava of the mammal and emplacing an inferior caval return catheter within the inferior vena cava of the mammal, wherein each of the superior caval return catheter and the inferior caval return catheter comprises
 (i) a hollow tubular body having a distal end, a port, and a venous blood uptake lumen extending longitudinally within the body from the port to a proximal portion of the body; and
 (ii) a vessel seat attached to the body, wherein the vessel seat is located nearer the distal end of the body than is the port.

The superior caval return catheter is positionable within the superior vena cava of the mammal such that the vessel seat of the superior caval return catheter is positioned between the right atrium and the junction of the of the brachiocephalic veins. The inferior caval return catheter is positionable within the inferior vena cava of the mammal such that the vessel seat of the inferior caval return catheter is positioned between the right atrium and the hepatic veins. When the inferior and superior vena cavae of the mammal are seated against the vessel seats, venous blood flow from the vena cavae of the mammal is diverted into the ports and into the venous blood flow lumens. In one embodiment of this method, the hollow body of at least one of the inferior caval return catheter and the superior caval return catheter has an access lumen extending from the distal tip of the body to the proximal portion of the body. The body of that catheter further comprises at least one penetrable seal disposed within the access lumen for permitting passage of a body through the seal while not permitting flow of venous blood through the access lumen from the distal tip to the proximal portion of the body. For example, the penetrable seal may comprise at least one balloon.

The invention also relates to a method of providing an agent to a single compartment selected from the group consisting of the cardiac circulation of a mammal and the non-cardiac, non-pulmonary circulation of the mammal. This method comprises isolating the cardiac circulation from the non-cardiac, non-pulmonary circulation and providing the agent to the single compartment. In one embodiment of this method, the cardiac circulation is isolated from the non-cardiac, non-pulmonary circulation by
 (1) inserting a cardiac isolation catheter of the invention into the vena cavae of the mammal,
 (2) seating the vena cavae against the distal and proximal vessel seats,
 (3) inserting an endoaortic catheter comprising an aortic vessel seat into the aorta of the mammal, and
 (4) seating the aorta against the vessel seat.

The cardiac circulation is thereby isolated from the systemic circulation. The cardiac isolation catheter may be a single catheter having at least two vessel seats or, as described herein, a pair of catheters having at least one vessel seat. In one embodiment of this method, the pulmonary artery of the mammal is also occluded, for example by threading a second catheter comprising an arterial vessel seat through a lumen extending longitudinally within the caval catheter, through an access port located between the vessel seats of the caval catheter, through the right atrium and right ventricle of the mammal's heart, and into the pulmonary artery of the mammal, and then seating the pulmonary artery against the arterial vessel seat. In another embodiment of this method, the azygous vein of the mammal is also occluded. The agent which is delivered by this method may, for example, be selected from the group consisting of a pharmaceutical composition, a composition comprising an imaging agent, and a gene vector (e.g. an adenovirus vector or an adeno associated vector). According to this method, at least one of the cardiac circulation and the non-cardiac, non-pulmonary circulation may be connected with an extracorporeal oxygenating unit.

The invention also includes a method of providing an apparatus to a venous blood cavity of the heart of a mammal. This method comprises inserting at least one catheter into the vena cavae of the mammal, diverting blood flow from the vena cavae of the mammal, and providing the apparatus to the cavity. The catheter comprises at least two vessel seats positionable within the vena cavae of the mammal and has an access port, an access lumen extending longitudinally within the catheter from the access port to a proximal portion of the catheter, at least two blood uptake ports, and at least one venous blood flow lumen extending longitudinally within the catheter from the ports to the proximal portion of the catheter. Blood flow through the vena cavae is diverted by seating the vena cavae against the vessel seats, whereby venous blood flows from the vena cavae, through the blood uptake ports, and into the venous blood flow lumen. The apparatus is provided to the cavity by passing the apparatus through the access port by way of the access lumen and into the cavity.

BRIEF DESCRIPTION OF THE DRAWINGS

FIG. 1 is a series of images depicting patterns of gene transfer in rat muscle in the absence of inflammatory mediators and demonstrates the integrity of the vascular endothelial barrier to adenovirus transport.

FIG. 6b is a graph which summarizes physiological data obtained from an approximately 40 kilogram sheep to which 300 milligrams of papaverine and 5 grams of histamine were administered. Abbreviations are the same as in FIG. 6a.

FIG. 9 is a diagram which illustrates the construction of one embodiment of the oxygenator depicted in FIG. 7.

FIG. 16, comprising FIG. 16A depicts the structure of the distal end of the catheter; the proximal end of the catheter is not shown. FIGS. 16B, 16C, and 16D depict cross-sections of the catheter depicted in FIG. 16A, along the planes indicated in FIG. 16A.

FIG. 17, comprising In FIG. 17A, the second catheter 40 is threaded through an access port 20 of the cardiac isolation catheter, as described herein. In FIG. 17B, the second catheter 40 is emplaced through the superior vena cava independently of the cardiac isolation catheter, but fits within a notch or indentation in the exterior surface of the cardiac isolation catheter at the location at which a snare S seats the superior vena cava against a vessel seat of the cardiac isolation catheter.

FIG. 19, comprising In FIG. 19A, an endoaortic catheter (EC) and a cardiac isolation catheter (CIC) are implanted within the subject, and an extracorporeal blood oxygenator (EBO) and an extracorporeal fluid circuit (EFC) are connected thereto, as described herein. In FIG. 19B, an endoaortic catheter (EC), a superior caval return catheter (SCRC), and an inferior caval return catheter (ICRC) are implanted within the subject, and an extracorporeal blood oxygenator (EBO) and an extracorporeal fluid circuit (EFC) are connected thereto, as described herein.

FIG. 20, comprising

DETAILED DESCRIPTION OF THE INVENTION

Figure 1A:
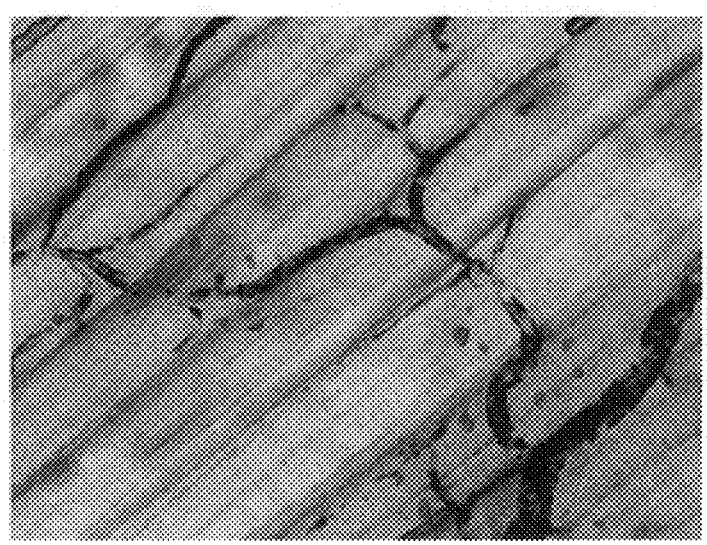
FIG. 1a is an image depicting, at 500×magnification, marker gene activity in the biceps femoris of an adult rat four days after arterial infusion of AdCMVlacZ (Table 1, series C) as assessed by staining with Xgal.

The invention includes compositions, methods, and an apparatus for delivering a macromolecular assembly such as a gene vector, to an extravascular tissue, such as muscle tissue. The compositions, methods, and apparatus of the invention involve the use of a vascular permeability-enhancing agent to alter the permeability of the endothelial layer of blood vessels of the vascular system. In some aspects of the invention, the compositions, methods, and apparatus involve the use of a vasodilating agent to improve the ability of the macromolecular assembly to be delivered to portions of a blood vessel that would, in the absence of the vasodilating agent, be too narrow to accommodate the assembly. Thus, in some aspects, the compositions, methods, and apparatus of the invention involve the use of both a vasodilating agent to improve delivery of a gene transfer vector to ordinarily inaccessible portions of a blood vessel and a vascular permeability-enhancing agent to improve passage of the vector through the endothelial layer of the vessel. Compositions useful for performing the method of the invention are provided, as is an apparatus comprising an oxygenator and a kit comprising one or more compositions and/or apparatus(es) for performing the method of the invention.

The invention is exemplified by the (independent) use of an adenovirus vector and an adeno associated vector as gene delivery vectors, the use of a vascular permeability-enhancing agent such as histamine, and the use of a vasodilating agent such as papaverine, to alter microvascular access and permeability. Thus, while the invention is not limited to the use of these virus vectors as gene delivery vehicles, the invention is exemplified by the use of these virus vectors to demonstrate the efficacy of the compositions, methods, and apparatus which have been developed to enhance microvascular access and permeability with respect to macromolecular assemblies. The invention should therefore not be construed to be limited solely to the use of these virus as gene delivery vehicles or to the use of histamine and papaverine as a means of altering microvascular access and permeability.

The continuous endothelium of the blood vessels which provide blood supply to skeletal muscle tissue blocks egress of an adenovirus from the vascular space to the muscle tissue. Different staining patterns arise after a marker virus is injected into the femoral artery upstream of a series of muscle fibers, as compared with the staining patters which arise after the marker is injected directly into the interstitium of the muscle fibers.

It has been hypothesized by others that adenovirus vector uptake by cells of an extravascular tissue is dependent wholly or primarily upon the presence on those cells of a virus receptor protein which is specifically bound by the vector, thereby facilitating uptake. Thus, it has been previously thought that adenovirus vectors were poor vectors for gene delivery to muscle tissue via the blood circulatory system of a mammal on account of a dearth of appropriate adenovirus receptor proteins on muscle cells. The data presented herein, as well as the observation that adenovirus vectors delivered directly to muscle tissue, for example, by direct injection of a vector suspension into muscle tissue, demonstrate that the ability of an adenovirus vector to deliver a gene to muscle tissue via the bloodstream is far more dependent upon the ability of the vector to penetrate the endothelial layer of the blood vessel than upon the presence of an adenovirus receptor protein on the surfaces of the cells of the tissue.

The appearance of mouse liver at necropsy following adenovirus gene vector delivery via the bloodstream, the effects of the Pringle maneuver upon the appearance of the mouse liver, and the discontinuity of the hepatic microvasculature, establish that the endothelial wall of the blood capillaries supplying the liver have discontinuities of up to one micron in diameter. These discontinuities accommodate chylomicrons of up to 600 nanometers in diameter, as indicated by the fact that they pass freely from the vascular space into the spaces around hepatocytes. The liver therefore removes, by a process analogous to filtration, particles of any sort including, for example, a circulating adenovirus gene vector. Where delivery of an adenovirus gene vector to an extravascular tissue such as striated muscle is desired, sequestration of the vector in the liver is undesirable. Thus, it has been discovered in the present invention that performance of the Pringle maneuver in conjunction with supplying a macromolecular assembly such as, for example, an adenovirus gene vector, to the bloodstream of a mammal, reduces hepatic sequestration of the assembly, enabling more efficient delivery of the assembly to a desired extravascular tissue such as muscle tissue.

Skeletal muscle is a highly vascular tissue. Since muscle performs a unique physiological role for the mammal, the extreme vascularity would appear to be an advantage to the gene therapist. The tissue has the greatest metabolic scope of all tissues, the metabolic scope being the ratio of the basal metabolic rate in non-stimulated tissue compared with its metabolic rate following maximal stimulation. For example, the resting metabolic rate in skeletal muscle tissue is equivalent to hydrolysis of about 2 micromoles of adenosine triphosphate per gram of wet tissue per minute. At maximal stimulation, the metabolic rate is equivalent to hydrolysis of about 120 micromoles of adenosine triphosphate per gram of wet tissue per minute. During anaerobic sprint, the metabolic rate is equivalent to hydrolysis of about 480 micromoles of adenosine triphosphate per gram of wet tissue per minute. Importantly, most capillaries in skeletal muscle tissue are not perfused at rest. Nonetheless, skeletal muscle is the preferred tissue for free tissue transfer in reconstructive surgery because of its vascularity.

Striated muscle is a formidable target for gene transfer. It comprises about half of the body weight of most mammals. Cardiac muscle is a form of striated muscle. Patients afflicted with muscular dystrophy are also afflicted with heart disease. Muscle is supplied with blood by blood vessels having a continuous epithelium. Under ordinary physiological conditions, the epithelial layer of these blood vessels is virtually impermeable to albumin, a protein having a Stokes radius of about 3 nanometers, which is about one thirtieth the radius of an adenovirus, which has a Stokes radius of about 70–90 nanometers. Thus, it is necessary that the permeability of the endothelial layer of the blood vessels which supply blood to muscle tissue be significantly increased relative to the layer's permeability under ordinary physiological conditions, if adenovirus gene vectors are to be permitted to pass through the layer.

Muscle is a very vascular tissue comprising much greater than half of the total capillary surface area in a mammalian body. Consequently, if the endothelium of muscle suddenly becomes permeable to albumin-sized molecules, circulatory collapse ensues in the absence of extracorporeal circulatory support, and the mammal experiences shock. Thus, the endothelial barrier is critical to homeostasis of the circulating blood volume. During normal circulatory homeostasis, the flow rate of blood past individual cells in the body provides oxygen at a rate which is adequate to meet the individual demands of the cell. During shock, this flow rate falls below that level to a non-sustainable level resulting in oxygen starvation of cells and, if the shock persists for a sufficient length of time, cell death ensues.

Endothelial pathophysiology, i.e., dysfunction of the walls of the microcirculatory channels in the body, occurs in a wide range of pathological states including inflammation, systemic anaphylaxis, septic shock, cardiopulmonary bypass, carcinoid syndrome, and carcinoid crisis. Each of these states involves an increase in vascular endothelial permeability which allows not only water, cations, and anions, but also large macromolecules to permeate the endothelial barrier.

The present invention is premised upon the observation that vascular endothelial permeabilization facilitates transfer of a macromolecular assembly, such as an adenovirus gene vector, from the vascular space across the vascular endothelium to an extravascular tissue, such as muscle tissue. As is described herein, vascular endothelial permeability can be pharmacologically enhanced. Therefore, it is possible to manipulate endothelial permeability using a vascular permeability-enhancing agent such as an inflammatory mediator or a derivative thereof, without necessarily inducing anaphylactic shock. Vascular permeability-enhancing agents are the mediators of choice because of the rapidity with which they act to alter endothelial permeability and the reversibility of their action.

The composition of the invention comprises a macromolecular assembly, such as a gene delivery vector, and a vascular permeability-enhancing agent. Preferred gene delivery vectors are virus vectors, more particularly adenovirus vectors.

Preferably, such a gene vector comprises a human gene, such as the gene encoding dystrophin, a gene encoding eutrophin, a gene encoding a sarcoglycan, or a gene encoding a minidystrophin. The gene vector may also comprise a promoter/regulatory region operably linked to the human gene, such as the human skeletal muscle creatine phosphokinase promoter/regulatory region, the murine skeletal muscle creatine phosphokinase promoter/regulatory region, a promoter/regulatory region of a gene which is ordinarily expressed in a human skeletal muscle cell, or a human constitutive promoter region. Methods of constructing gene vectors are well known in the art.

Preferable vascular permeability-enhancing agents are those which alter permeability of the vascular endothelium to the extent that the endothelium will accommodate a virus vector having a diameter of approximately 150–200 nanometers. Numerous vascular permeability-enhancing agents are known, including, but not limited to, histamine, acetylcholine, adenosine nucleotides, arachidonic acid, bradykinin, cyanide, endothelin, various endotoxins, interleukin-2, ionophore A23187, nitroprusside, various leukotrienes, oxygen radicals, phospholipases, platelet activating factor, protamine, serotonin, tumor necrosis factor, vascular endothelial growth factor (VEGF), numerous venoms, and numerous vasoactive amines. Of the agents listed herein, two are preferred, namely histamine and VEGF.

Histamine has been widely characterized, and its pharmacologic properties are relatively well understood. As described herein, histamine is an efficacious agent for enhancing vascular endothelial permeability to the extent that an adenovirus gene vector can pass from the bloodstream to an extracellular tissue. Hence, histamine is a preferred vascular permeability-enhancing agent of the invention. Administration of histamine to a mammal has numerous known and undesirable side effects. Numerous compositions, such as antihistamines and histamine receptor antagonists, are known which are useful for reversing or alleviating the side effects of histamine in a mammal. The use of such compositions, either in conjunction with or following administration of histamine to a mammal is contemplated as a variant of the invention. While not wishing to be bound by any particular theory, it is believed that certain antihistaminic agents act by blocking, reversing, or antagonizing the binding of histamine to one or more species of histamine receptor, such as an H1 or an H2 receptor of histamine while not affecting the interaction of histamine with one or more other histamine receptors. Thus, certain antihistaminic agents may be particularly useful for preventing or reversing the undesirable side effects of administering histamine to a mammal while not affecting the vascular permeability-enhancing properties of histamine. Administration of such antihistaminic agents in conjunction with or following administration of histamine in the compositions, methods, and apparatus of the invention is contemplated in the present invention.

VEGF has been demonstrated to be a vascular permeability-enhancing agent that is efficacious at a far lower concentration than is histamine. Furthermore, VEGF does not induce all of the undesirable side effects induced by histamine (Roberts et al., 1995, J. Cell Sci. 108:2369–2379; Roberts et al., 1997, Cancer Res. 57:765–772; Sanger et al., 1990, Cancer Res. 50:1774–1778). Hence, VEGF is a preferred vascular permeability-enhancing agent of the invention.

The invention is also premised upon the observation that vasodilation of capillary beds improves the efficiency of gene transfer from the vascular space across the vascular endothelium to an extravascular tissue. This effect is less critical in liver due to the fenestration of this organ, but is crucial in the case of other extravascular tissues, such as muscle tissue, wherein most of the capillaries are not perfused at rest. Vasodilation causes broadening of the lumen of capillaries and, without being bound by any particular theory of operation, may also cause or improve fenestration of the vascular endothelium. Thus, vasodilation improves exudation from a blood vessel into an extravascular tissue. As described herein, a vasodilating compound improves delivery of a vascular permeability-enhancing agent to narrow portions of a blood vessel, thereby improving the efficacy of the agent by permitting it to act upon a greater proportion of the vessel's endothelial surface. Vasodilation also improves delivery of a macromolecular assembly to narrow portions of a blood vessel, thereby permitting improved transepithelial delivery of the assembly due to increased epithelial surface area available for such delivery. Numerous vasodilating agents are known in the art, including, but not limited to, papaverine, nimodipine, hydralazine, epoprostenol, nitric oxide, tolazoline, amrinone, milrinone, nitroglycerine, isosorbide dinitrate, isosorbide mononitrate, and numerous organic nitrate compounds.

Thus the present invention contemplates a composition comprising a macromolecular assembly, such as a gene delivery vector, a vascular permeability-enhancing agent, and a vasodilating agent. Preferably, the vasodilating agent is papaverine.

In one embodiment, the composition of the invention comprises a pharmaceutically-acceptable carrier, such as an isotonic buffering agent or the like. The composition may be administered to a mammal to deliver an amount of the macromolecular assembly in the range from one nanogram per kilogram of body weight per day to one hundred milligrams per kilogram of body weight per day. The composition may be administered in a single dose or in multiple doses, the multiple doses administered over a course of days, weeks, or months.

The vascular permeability-enhancing agent or the vasodilating agent or both of the composition of the invention may be provided to a blood vessel of a mammal in the form of a pharmaceutical composition. Pharmaceutical compositions that are useful in the methods of the invention may be administered systemically in oral solid formulations, ophthalmic, suppository, aerosol, topical or other similar formulations. In addition to the vascular permeability-enhancing agent or the vasodilating agent or both, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer the vascular permeability-enhancing agent or the vasodilating agent or both according to the methods of the invention.

In another embodiment, the composition of the invention further comprises an oxygen-transporting agent, so that oxygen may be delivered to the extravascular tissue, for example, during exposure of the tissue to the gene delivery vector. Any oxygen-transporting agent known in the art may be used, including, but not limited to, the blood of the mammal to which the composition is being administered, blood from a different individual of the same type of mammal, a perfluorochemical liquid, a hemoglobin-containing composition, or the like.

The composition of the invention may be provided in the form of a kit for delivering a macromolecular assembly to an extravascular tissue of a mammal, the kit comprising a vascular permeability-altering agent and a vasodilating agent. Preferably, the vascular permeability-enhancing agent is histamine or vascular endothelial growth factor and the vasodilating agent is papaverine. Where the kit is intended to be used to deliver a gene vector to an extravascular tissue, the kit may also comprise the gene vector, such as an adenovirus vector. Preferably, such a gene vector comprises a human gene, such as the gene encoding dystrophin, a gene encoding eutrophin, a gene encoding a sarcoglycan, or a gene encoding a minidystrophin. The gene vector may also comprise a promoter/regulatory region operably linked to the human gene, such as the human skeletal muscle creatine phosphokinase promoter/regulatory region, the murine skeletal muscle creatine phosphokinase promoter/regulatory region, a promoter/regulatory region of a gene which is ordinarily expressed in a human skeletal muscle cell, or a human constitutive promoter region. Methods of constructing gene vectors are well known in the art.

Other compositions of the invention may be provided in the form of a kit for delivering a macromolecular assembly specifically to cardiac myocardium. Preferred macromolecular assemblies for this kit include, for example, pharmaceutical or other therapeutic compositions which are useful for treating cardiomyopathies. Such compositions include gene vectors which comprise one or more polynucleotides encoding a gene product which, when expressed in cardiac myocardium, yields a therapeutic effect. Exemplary gene products include, by way of example and not limitation, an antisense oligonucleotide, such as one capable of interacting with a nucleic acid encoding angiotensin 1 receptor, or a protein, such as VEGF, angiopoietin 1, angiopoietin 2, a beta-adrenergic receptor, a beta-adrenergic receptor kinase, a beta-adrenergic receptor kinase inhibitor, or an alpha-adrenergic receptor.

The invention is further premised on the observation that mechanical circulatory support and extracorporeal oxygenation extends the pharmacological range of the composition of the invention. In other words, if a mammal is connected to a heart-lung machine, it is possible to do all of the following. The heart is protected functionally from the effects of the vascular permeability-enhancing agent and the effects of any vasodilating agent included in the composition. Massive vasodilatation in the absence of extracorporeal support results in reflex tachycardia and increased contractility to the heart, both of which would cause damage to an already genetically deficient heart, such as the heart of a human afflicted with muscular dystrophy. Furthermore, extracorporeal circulation permits independent control of pulmonary perfusion pressure, including that within the pulmonary artery. Placement of a large cannula in the right atrium of a human heart permits withdrawal of blood from the right atrium prior to right ventricular filling during cardiac diastole. This reduces systolic pulmonary artery pressure and decreases exudation from blood vessels into the pulmonary parenchyma, thereby preventing fluid accumulation in the lungs of the human. This is important to minimize the acute morbidity of the intervention. The extracorporeal circuit also ensures vascular access for rapid replacement of fluid which passes from the bloodstream to an extravascular tissue during exudation, and permits maintenance of adequate tissue oxygenation throughout the body during the procedure. The oxygenation provided by the heart-lung machine is independent of the alveolar-to-arterial gradient, thereby circumventing hypoxemia associated with pulmonary edema. In other words, blood which is circulating through the extracorporeal pump can be fully oxygenated prior to delivery to the body. The extracorporeal circuit can also be instituted by a minimally invasive access route.

Figure 8:
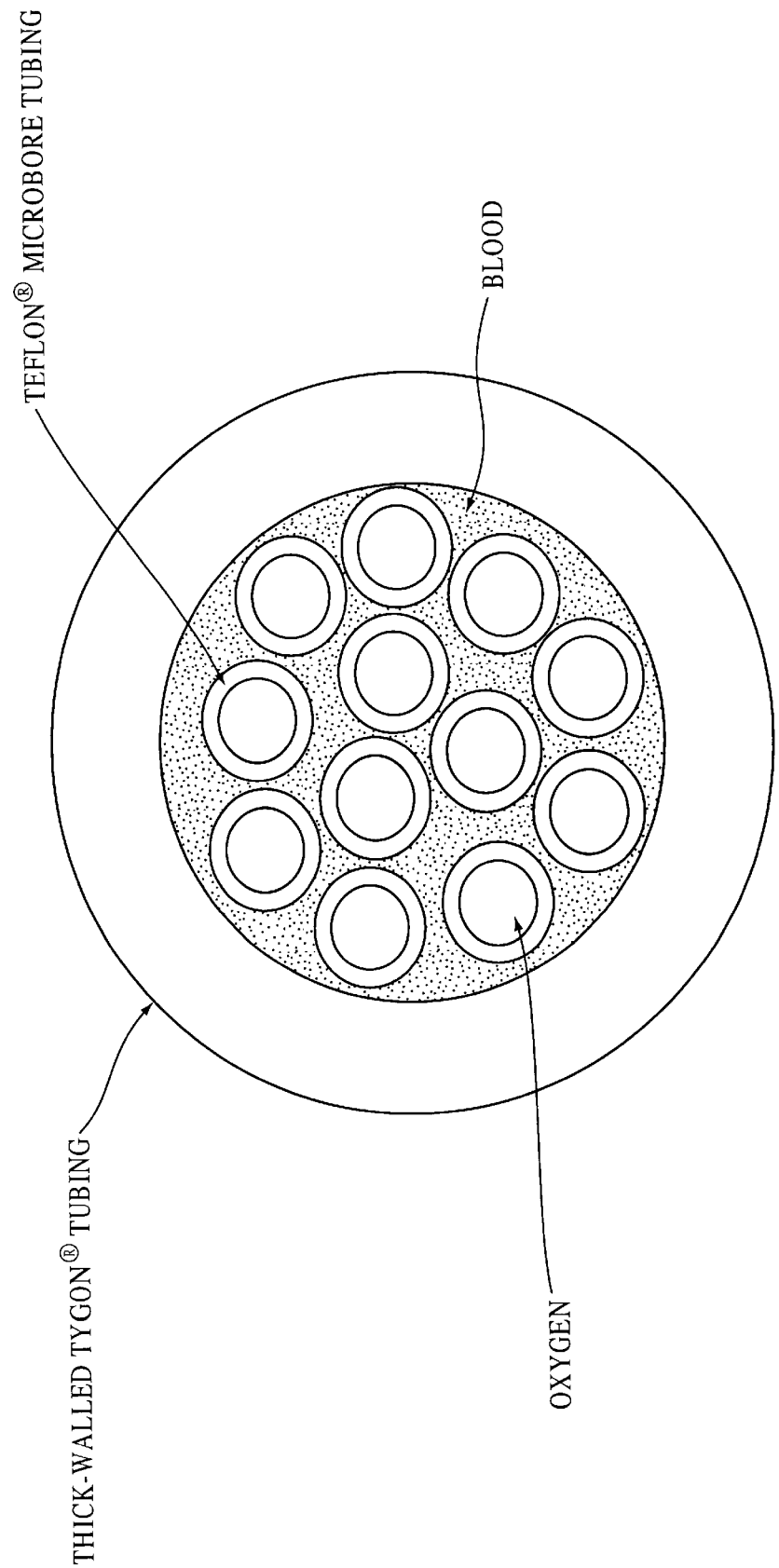
FIG. 8 is a diagram which illustrates the operation of one embodiment of the oxygenator depicted in FIG. 7.
Figure 10:
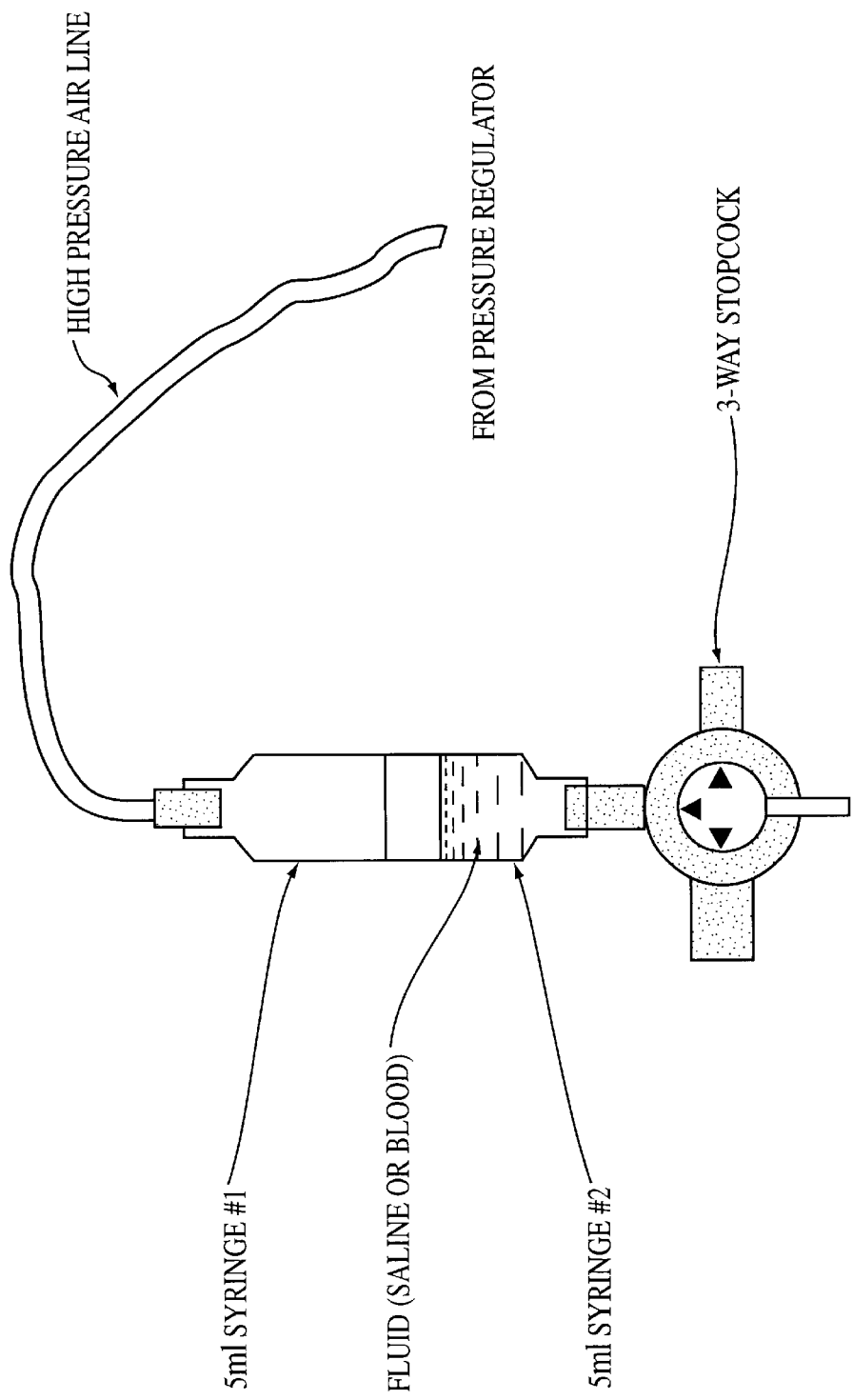
FIG. 10 is a diagram which illustrates the construction of one embodiment of the interface between the pressure regulator and the delivery mechanism depicted in FIG. 7.

Thus, the kit of the invention may also comprise an oxygen-transporting agent or at least one disposable element of an extracorporeal circulatory support and oxygenation system. For example, the at least one disposable element may be an oxygenator having a hollow body, a liquid inlet in fluid communication with the interior of the body, a liquid outlet in fluid communication with the interior of the body, a gas inlet for providing gas to the interior of a gas chamber, at least one gas-permeable membrane separating the gas chamber from the interior of the body, and a gas outlet for permitting gas to exit from the gas chamber, whereby gas exchange is enabled between a fluid in the interior of the body and a gas in the gas chamber. The oxygenator may be constructed analogously to that illustrated in FIGS. 8 and 9, wherein the gas-permeable membrane comprises PTFE tubing extending within at least a portion of the tube, and wherein the gas chamber comprises the interior of the PTFE tubing.

A kit which is useful for performing the method of the invention is contemplated which comprises, in addition to the composition of the invention, at least one disposable element of an extracorporeal circulatory support and oxygenation system and at least one cannula for providing the composition of the invention to a blood vessel of a mammal. Preferably, such a kit comprises all of the single-use components needed to perform the method of the invention, including a macromolecular assembly, a vascular permeability-enhancing agent, a fluid delivery instrument such as a syringe or a length of peristaltic pump tubing, and a cannula such as a hollow bore needle adapted to fit a syringe. Such a kit may also comprise a vasodilating agent, a pharmaceutically acceptable carrier, a second cannula, an oxygen-transporting agent, a clearance solution which is substantially free of the vascular permeability-enhancing agent, one or more blood vessel occluding devices, such as a clamp, hemostat, or tourniquet, a disposable oxygenator, and the like.

The method of the invention is a method of delivering a macromolecular assembly such as a gene vector to an extravascular tissue of a mammal. The extravascular tissue may optionally be isolated from systemic circulation (e.g. cardiac muscle tissue or limb muscle tissue isolated from systemic circulation. The method comprises the steps of providing a vascular permeability-altering agent to a blood vessel associated with the tissue to increase the permeability of the endothelial layer of the vessel and providing the gene vector to the vessel, whereby the vector is delivered to the tissue through the endothelial layer of the vessel. The vascular permeability-altering agent may be provided to the vessel simultaneously with the vector, or may be provided to the vessel before or after the vector is provided. Preferably, the vascular permeability-enhancing agent is histamine or VEGF. By way of example, a composition comprising 10 millimolar histamine and an adenovirus vector may be provided to a blood vessel of a mammal, wherein the histamine enhances the permeability of the blood vessel, whereby the adenovirus vector can pass through the endothelial layer of the blood vessel to an extravascular tissue, such as a muscle which is adjacent the blood vessel. The concentration of the vascular permeability-enhancing agent which is used in the method depends on the identity of the agent, but must be sufficient to enhance the permeability of the blood vessel, such that after exposure to the agent, the vessel has a greater permeability than it does before exposure to the agent. Useful concentrations of vascular permeability-enhancing agents are known in the art.

In another embodiment, the method of the invention further comprises providing a vasodilating agent to the vessel, preferably prior to providing the gene vector to the vessel, and also preferably prior to providing the vascular permeability-enhancing agent. The vasodilating agent may be provided before, during, or after provision of the composition of the invention. The concentration of the vasodilating agent is not critical, although it must be sufficiently great to induce vasodilation in the vessel. As noted herein, numerous vasodilating agents are known in the art, as are the concentrations of those agents which are useful for promoting vasodilation. It is contemplated that a higher concentration of the vasodilating agent may be used when the mammal to which the vasodilating agent is administered is subjected to mechanical circulatory support to compensate for the physiological side effects of the vasodilating agent. The use of papaverine in the method of the invention is preferred.

The method of the invention may be used to deliver a macromolecular assembly to any extravascular tissue including, but not limited to, muscle tissue, striated muscle tissue, cardiac muscle tissue, bone tissue, bone marrow tissue, skin tissue, brain tissue, and the like. As noted herein, it is not necessary to use the method of the invention to deliver such an assembly to certain fenestrated extravascular tissues, such as liver and spleen. Nonetheless, the method of the invention may be used to deliver a macromolecular assembly to any extravascular tissue, whether fenestrated or not.

The mammal to which the composition of the invention is provided is preferably a mammal, and even more preferably a human. Provision of the composition of the invention to a human afflicted with muscular dystrophy is particularly contemplated.

In a variation of the method of the invention, the perfusion pressure within the blood vessel is increased above the normal physiological perfusion pressure after providing the gene vector to the vessel. The increase in perfusion pressure may be within the range from 5 to 80 pounds per square inch or more. However, it is recognized that the greater the increase in perfusion pressure, the greater is the risk of structural damage to vascular and extravascular tissues. Nonetheless, one skilled in the art is able, using the information disclosed herein, to weigh the benefit to be gained by increasing perfusion pressure and the corresponding risk of tissue damage. It is contemplated that in situations in which a blood vessel has been isolated from the blood circulatory system of a mammal, and particularly from the mammal's heart, the risk of injury to the mammal is less dependent upon the increase in perfusion pressure, compared with the situation in which the blood vessel is not so isolated.

Blood vessel occlusion is useful in the method of the invention for a number of reasons. As described in the preceding paragraph, isolating a blood vessel prior to increasing the pressure in that vessel can minimize the pressure increase in other blood vessels and tissues of the mammal. Occlusion of the blood vessel to which the composition of the invention is provided can also minimize the amount of the composition that is available to the circulatory system of the mammal or to other tissues of the mammal. Particularly where a composition comprises an amount of a vascular permeability-enhancing agent or a vasodilating agent which would be harmful to the mammal if provided to the circulatory system of the mammal, sequestration of the composition to the desired blood vessel is beneficial, and can be achieved by occluding the desired blood vessel prior to providing the composition to the vessel. It may also be useful to provide a composition comprising an oxygen-transporting agent to the vessel if occlusion is to persist for more than a few minutes. It may be useful to continue occluding the blood vessel until the vascular permeability-enhancing agent, the vasodilating agent, or both have been metabolized to non-harmful levels.

Alternately, a clearance composition may be provided to the blood vessel following provision to the vessel of the composition of the invention. The clearance composition is substantially free of the vascular permeability-enhancing agent, and is preferably free of any vasodilating agent that was present in the composition of the invention. Provision of the clearance composition to the vessel after provision of the composition of the invention to the vessel can serve to dilute or 'wash out' any vascular permeability-enhancing agent or vasodilating agent which was provided to the vessel, but which was not metabolized or absorbed by a tissue of the mammal. Preferably, a plurality of individual aliquots of the clearance composition is provided to the blood vessel in a sequential fashion.

Particularly in situations in which the composition of the invention is provided to the blood circulatory system of a mammal, or to a portion of that system including the hepatic blood flow vessels, it may be useful to occlude blood vessels which supply tissues capable of sequestering the macromolecular assembly of the composition. For instance, as described herein, transient hepatic flow occlusion minimizes adenovirus vector sequestration. The Pringle maneuver involves the placement of the surgeon's forefinger behind the hepatoduodenal ligament so that the thumb can occlude against the finger the two major vessels providing blood supply to the liver, namely the hepatic artery and the portal vein. It is possible to perform this procedure in humans as young as about one year of age, and up to one hour of hepatic inflow occlusion is known to be tolerated.

Any method of occluding flow through a blood vessel may be used in the method of the invention. Numerous occlusion methods are known in the art, including digital occlusion wherein a surgeon occludes a blood vessel by applying finger pressure, use of a clamp, use of a hemostat, use of a tourniquet, use of an angiographically- or radiographically-placed balloon, and the like.

Where it is desired to provide the composition to the systemic blood circulation of a mammal, but not to the lungs of a mammal, the method of the invention further comprises the step of subjecting the mammal to extracorporeal circulatory support and oxygenation prior to providing the vascular permeability-enhancing agent. Preferably, a heart-lung machine is used according to methods known in the art. Extracorporeal circulatory support and oxygenation permits blood flow to the lungs of the mammal to be minimized, thus minimizing exudation from the pulmonary blood vessels of the mammal into the lungs.

Figure 3:
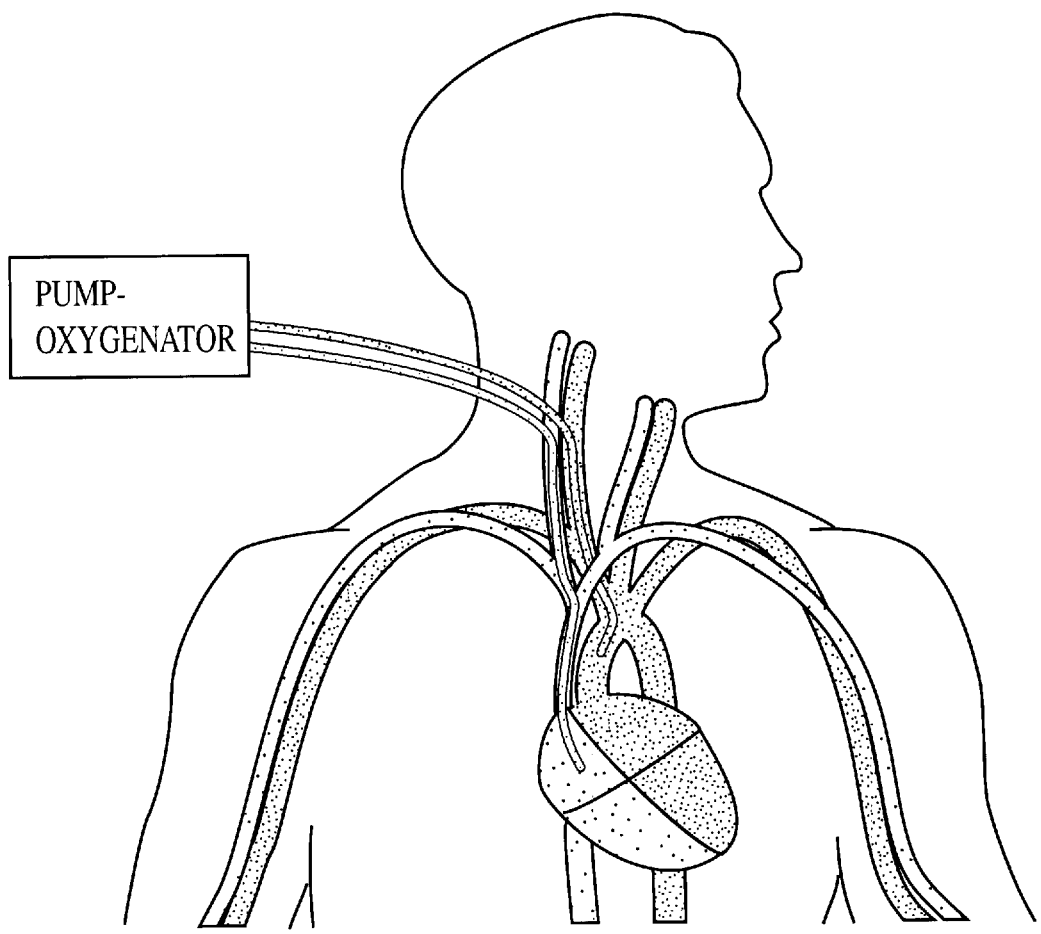
FIG. 3 is a diagram depicting the position of a pump oxygenator relative to a human patient.
Figure 4:
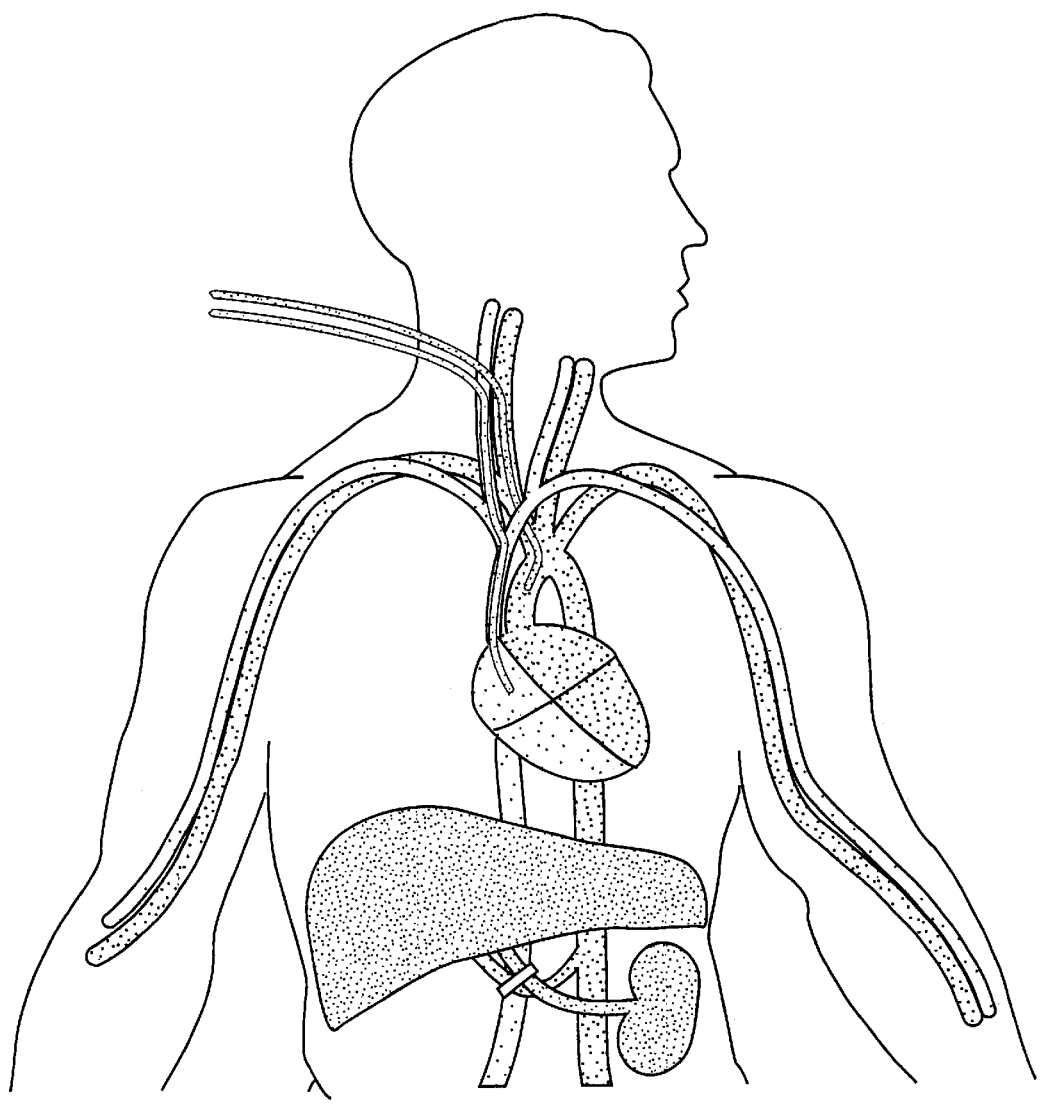
FIG. 4 is a diagram depicting the position of cannulation and a position useful for hepatic blood flow occlusion in a human patient.
Figure 5:
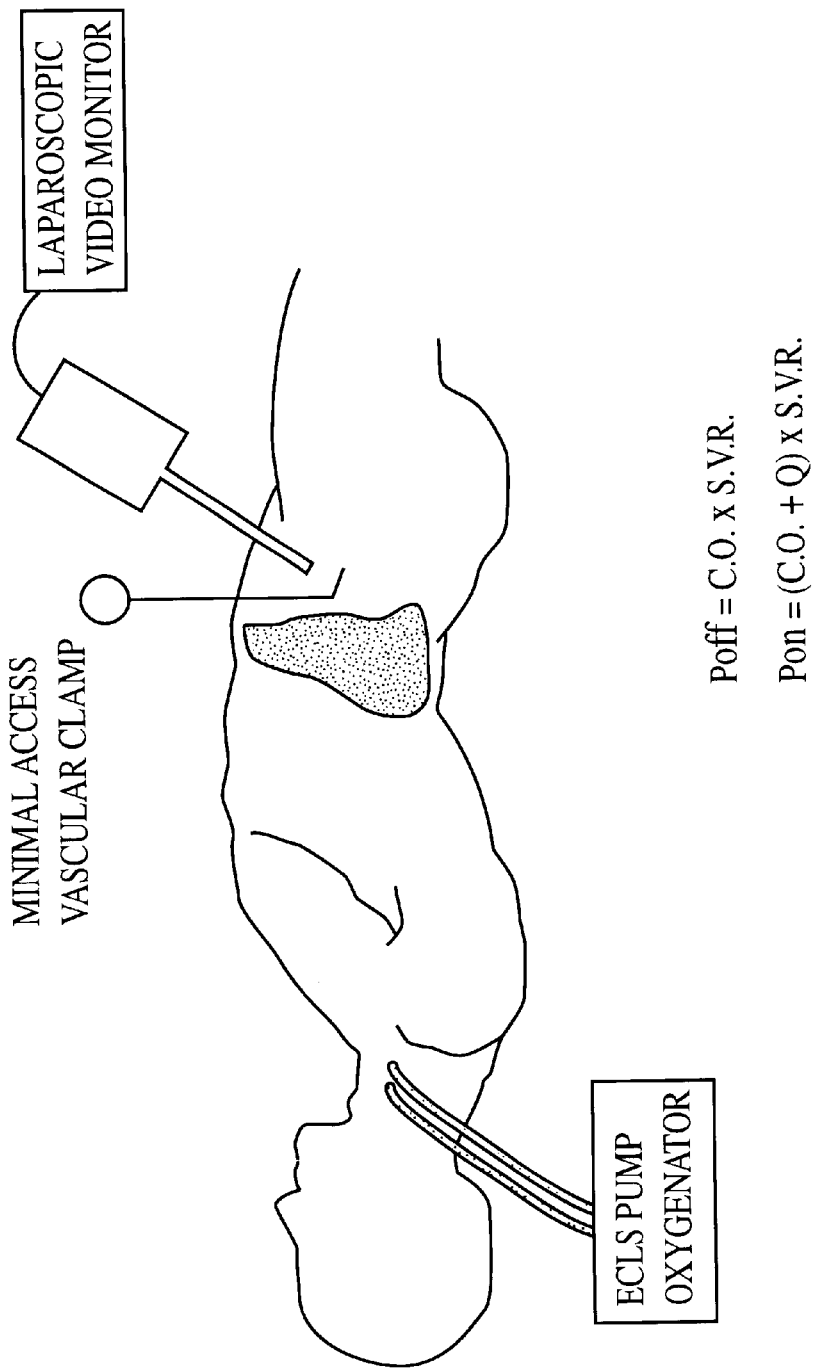
FIG. 5 is a diagram depicting the relative positions of a minimal access vascular clamp, an ECLS pump oxygenator, and a laparoscopic video monitor in a human patient.

A method of subjecting a human to extracorporeal circulatory support and oxygenation is illustrated in FIG. 5. In this method, an ECLS pump oxygenator is connected to a pair of cannulae inserted into the human as illustrated in FIG. 3, one cannula extending into the right atrium of the human, and the other cannula extending into the aorta of the human. Blood is withdrawn from the right atrium, oxygenated extracorporeally, and returned to a systemic (e.g. the aortic arch or a femoral artery) of the human at a controlled pressure and flow rate. Using this method, blood flow to the lungs is minimized, and exudation from pulmonary blood vessels into the parenchyma of the lungs is minimized. As illustrated in FIG. 4, hepatic blood flow in the human may also be occluded.

One contemplated embodiment of the method of the invention is a method of delivering a gene vector to an extravascular tissue of a mammal. The method comprises the following steps. A blood vessel associated with the tissue is isolated from the blood circulatory system of the mammal. Thereafter, a vasodilating agent is provided to the vessel. Thereafter a vascular permeability-enhancing agent is provided to the vessel to increase the permeability of the endothelial layer of the vessel, the gene vector is provided to the vessel, whereby the vector is delivered to the tissue through the endothelial layer of the vessel, the perfusion pressure within the vessel is increased above the normal physiological perfusion pressure, and an oxygen-transporting agent is provided to the vessel. Thereafter a clearance solution is provided to the vessel, the clearance solution being substantially free of the vascular permeability-enhancing agent.

Thus, according to this embodiment of the method of the invention, delivery of the gene vector to the extravascular tissue is enhanced by the presence of the vasodilating agent, the presence of the vascular permeability-enhancing agent, and the increased perfusion pressure within the blood vessel of the mammal. Furthermore, the gene vector and both agents remain localized in the blood vessel due to the occlusion of the vessel prior to delivery of the vector and the agents. Because an oxygen-transporting agent is provided to the vessel, the vessel may remain occluded, and the vector and agents may remain within the vessel for an extended period. Also, because a clearance solution is provided to the vessel, excess vector and agents are removed from the vessel prior to re-establishing systemic blood circulation in the mammal, thereby minimizing any potential undesirable effects caused by the presence of the vector or agents in an area of the mammal's body other than the vessel.

The method of the invention may be used to provide a gene vector to substantially all muscle tissues of a mammal. The method comprises the following steps. The mammal is subjected to extracorporeal circulatory support and oxygenation. Thereafter, a vasodilating agent is provided to the blood circulatory system of the mammal, a vascular permeability-enhancing agent is provided to the blood circulatory system to increase the permeability of the endothelial layer of the vessels of the blood circulatory system, the gene vector is provided to the blood circulatory system, whereby the vector is delivered to substantially all muscle tissues through the endothelial layer of the vessels of the blood circulatory system, and the perfusion pressure within the blood circulatory system is increased above the normal physiological perfusion pressure. In order to decrease sequestration of the gene vector in the liver of the mammal, the Pringle maneuver may be performed whereby hepatic blood flow to the liver is occluded. In order to decrease sequestration of the gene vector in viscera of the mammal, complete visceral inflow occlusion may be performed. Complete visceral inflow occlusion may be achieved, for example, by occluding blood flow through the celiac axis, the superior mesentery artery, and the inferior mesentery artery, and may be maintained for at least fifteen minutes. These three blood vessels may be accessed, for example, by a laparoscopic or surgical procedure or by passing a balloon through the femoral artery.

Another important embodiment of the invention is a method of providing a fluid (e.g. one comprising a gene vector) to cardiac muscle tissue of a mammal, but not to other muscle tissues in the body in an appreciable amount. This method comprises isolating the cardiac circulation from the systemic circulation of the mammal. The cardiac circulation of the mammal may be isolated from the systemic circulation using any of the methods described herein in Example 6. Use of the minimally-invasive technique involving use of the cardiac isolation catheter of the invention, as described herein, is preferred. These methods may be used, among other purposes, to provide a gene vector specifically to cardiac tissue. The inflammatory mediators of the invention may be used intracardially to enhance gene vector delivery to isolated myocardial tissue and washed from the cardiac circulation prior to re-mixing cardiac and systemic circulation.

The apparatus of the invention comprises an oxygenator that can be used to provide oxygen to an oxygen-transporting agent, such as the blood of a mammal, prior to provision of the agent to a blood vessel of the mammal. The oxygenator of the invention has a hollow body, a liquid inlet in fluid communication with the interior of the body, a liquid outlet in fluid communication with the interior of the body, a gas inlet for providing gas to the interior of a gas chamber, at least one gas-permeable membrane separating the gas chamber from the interior of the body, and a gas outlet for permitting gas to exit from the gas chamber, whereby gas exchange is enabled between a fluid in the interior of the body and a gas in the gas chamber. The oxygenator may be constructed analogously to that illustrated in FIGS. 8 and 9, wherein the gas-permeable membrane comprises PTFE tubing extending within at least a portion of the tube, and wherein the gas chamber comprises the interior of the PTFE tubing. Because of the simple construction of the oxygenator of the invention, it may be constructed inexpensively and treated as a single-use, disposable element of an extracorporeal oxygenation system. The simple construction of the oxygenator of the invention also permits it to be made with dimensions adapted to oxygenation of very small volumes of liquid, such as the volume of the contents of a blood vessel of a mammal. By altering the proportions of the oxygenator, particularly the surface area of the gas-permeable membrane which is capable of contacting the liquid phase within the body of the oxygenator, the oxygenator may be made to support nearly any liquid phase flow rate. Such proportioning techniques are well known in the art.

The oxygenator of the invention is used by passing an oxygen-transporting agent through the body of the oxygenator, whereby the agent contacts the gas-permeable membrane. Oxygen, air, or another gas supplied to the gas chamber is capable of diffusing through the gas-permeable membrane and into the agent, which may be supplied to a blood vessel of a mammal. As described herein, any oxygen-transporting agent may be used. An oxygenator having a relatively small volume within its hollow body may be used when the volume of agent to be supplied to an occluded blood vessel is small; similarly, an oxygenator having a proportionally greater volume may be used if the oxygenator is to be used to provide oxygen to a greater volume of agent.

Support for the hypothesis that mechanical circulatory support and extracorporeal oxygenation extends the pharmacological range of the inflammatory mediator/vasodilator mix is found in the following information. It has been found in the present invention that the isolated perfused heart survives infusion of the same histamine and papaverine doses used in skeletal muscle and these doses are tolerated as long as the mediator is flushed out before systemic circulation is restored. If these compounds gain access to the systemic circulation of an unsupported heart, cardiogenic shock ensues.

To support the heart during administration of histamine and papaverine, two approaches may be used. First, the heart of a suitable donor may be isolated and perfused ex vivo prior to transplantation of the heart into the mammal being treated. Second, the transplantation is performed first into the femoral circulation, the side branch vessels of the epigastric system are cannulated and the heart is perfused in situ, and before removing the cannula the system is flushed using a high hind limb tourniquet which prevents leaking of the pharmacological agents into the systemic circulation. Both of these procedures allow very transient use of the pharmacological agents in the supraphysiologic perfusion pressures that are possible with a modified pump oxygenator without the need for any circulatory support for the rest of the mammal. Therefore, the heart and lungs of the affected mammal are still functioning normally.

Apparatus and methods for providing a composition to a blood vessel are well known in the art and include, for example, cannulation methods, syringe-mounted hollow bore needle delivery, delivery via a length of flexible tubing engaged by a peristaltic pump, and the like. However, the invention includes certain new and useful apparatus for performing the methods described herein.

For example, the invention includes a cardiac isolation catheter which is insertable within the vena cava of a mammal such as a human. The cardiac isolation catheter comprises (a) a hollow tubular body having a venous blood flow lumen extending longitudinally therein, a proximal end, a distal end, a proximal port, and a distal port;

(b) a distal vessel seat attached to the body; and (c) a proximal vessel seat attached to the body.

The cardiac isolation catheter is positionable within the vena cava of the mammal such that one vessel seat is positioned in the superior vena cava of the mammal between the right atrium and the junction of the brachiocephalic veins and the other vessel seat is positioned in the inferior vena cava between the right atrium and the hepatic veins. This arrangement allows isolation of the right atrium from non-cardiac, non-pulmonary venous circulation, it being recognized that occlusion of the azygous vein may also be necessary in order to fully isolate the right atrium from non-cardiac blood circulation. The distal port of the cardiac isolation catheter is located distally with respect to the distal vessel seat. The proximal port is located proximally with respect to the proximal vessel seat. Because both the proximal and distal ports of the cardiac isolation catheter communicate with the venous blood flow lumen of the catheter, blood in the junction of the brachiocephalic veins and blood in the hepatic veins is in fluid communication with the venous blood flow lumen by way of the ports. Thus, emplacement of the cardiac isolation catheter within the vena cavae of a subject isolates the cardiac circulation from the non-pulmonary systemic circulation.

In one embodiment, the cardiac isolation catheter comprises one or more right atrium fluid access ports which communicate with a fluid access lumen extending longitudinally in the catheter from the ports to a proximal portion of the catheter. Fluid in the right atrium, the right ventricle, and the proximal portion of the pulmonary artery may be withdrawn from the heart through these ports. Such fluid flow may be motivated by intracardiac pressure, by extracorporeally generated suction applied to the fluid access lumen, or both. When suction is applied to the fluid access lumen, the fluid access lumen may also communicate with any suction port(s) associated with a vessel seat(s) on the catheter (otherwise, a separate suction lumen may be used). When a plurality of right atrium fluid access ports are present, they are preferably circumferentially arranged about the body of the catheter, in order to minimize the likelihood that all ports will be blocked by venous or cardiac tissue.

When the cardiac isolation catheter is used for delivery of a liquid (e.g. a fluid comprising a gene vector) to the cardiac circulation, it is not necessary to isolate the cardiac circulation from the pulmonary veins. Valves within the heart prevent retrograde passage of fluid from the left atrium and left ventricle into the pulmonary veins. However, in order to prevent the liquid from entering the pulmonary circulation from the heart, the pulmonary circulation may be isolated from liquid in the cardiac circulation by occluding the pulmonary artery. The pulmonary artery may be occluded using the cardiac isolation catheter of the invention and a second catheter having an occlusive device thereon.

By way of example, the second catheter may be a catheter having a distal portion and a vessel seat at the distal portion. The second catheter is insertable within at least one lumen (e.g. the fluid flow lumen thereof) of the cardiac isolation catheter, and emerges therefrom through an access port. The second catheter is positionable within the subject's heart such that the vessel seat of the second catheter passes from the access port, across the right ventricle, and into the root of the pulmonary artery. The second catheter may have a curved or manipulable portion to facilitate such placement. The second catheter may be made 'steerable' using methods well known in the art. Such methods generally include association of a stiff filament (e.g. a wire) with the catheter, whereby application of longitudinal or torque force to the filament deflects, displaces, or distorts the tip of the catheter, or induces a curvature in the catheter, whereby the catheter may be more easily guided through a non-straight passageway. Similarly, the catheter may be guidable by insertion of a stiff filament within a lumen of the catheter, whereby the shape of the catheter assumes the shape of the stiff filament, thereby permitting the catheter to be more easily guided through a non-straight passageway.

The second catheter may also, or alternately, have a shape adapted to the shape of the heart of the subject (e.g. a shape adapted to the interior of a human heart). When the second catheter has such an adapted shape, the catheter may have a withdrawable sheath covering it, whereby the sheath maintains the catheter substantially straight during insertion of the catheter but permits the second catheter to attain its adapted shape upon withdrawal of the sheath. Preferably, the vessel seat is located in the pulmonary artery at a position distal to the pulmonary valve. By seating the pulmonary artery against the vessel seat of the second catheter, fluid flow through the pulmonary artery is occluded. The vessel seat may be at the distal tip of the second catheter, or it may circumferentially surround the distal portion of the catheter, such that the distal end of the second catheter extends distally beyond the vessel seat.

Figure 17A:
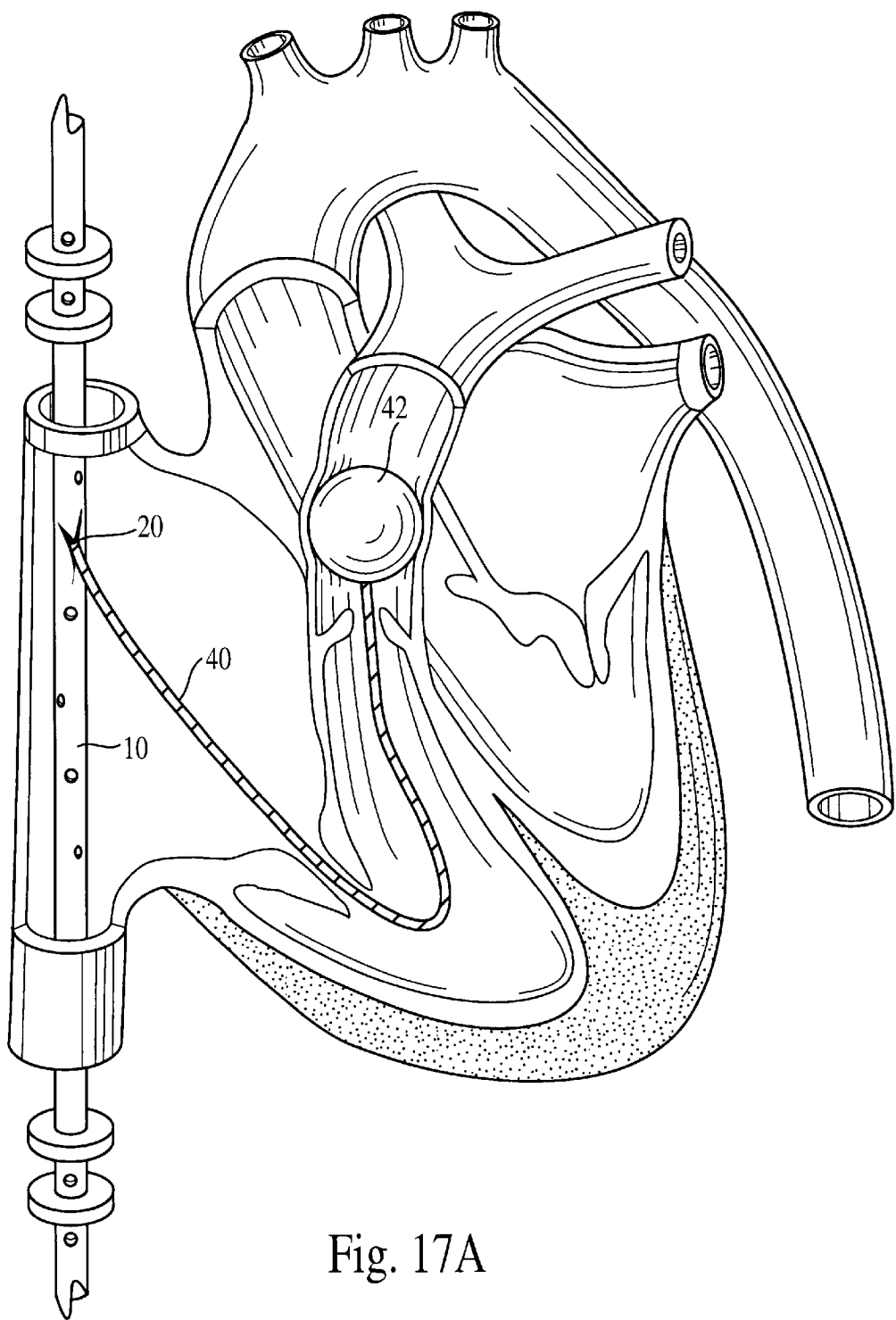
FIGS. 17A and 17B depicts a human heart having a cardiac isolation catheter threaded through the vena cava associated therewith and a second catheter emplaced within the pulmonary artery.
Figure 17B:
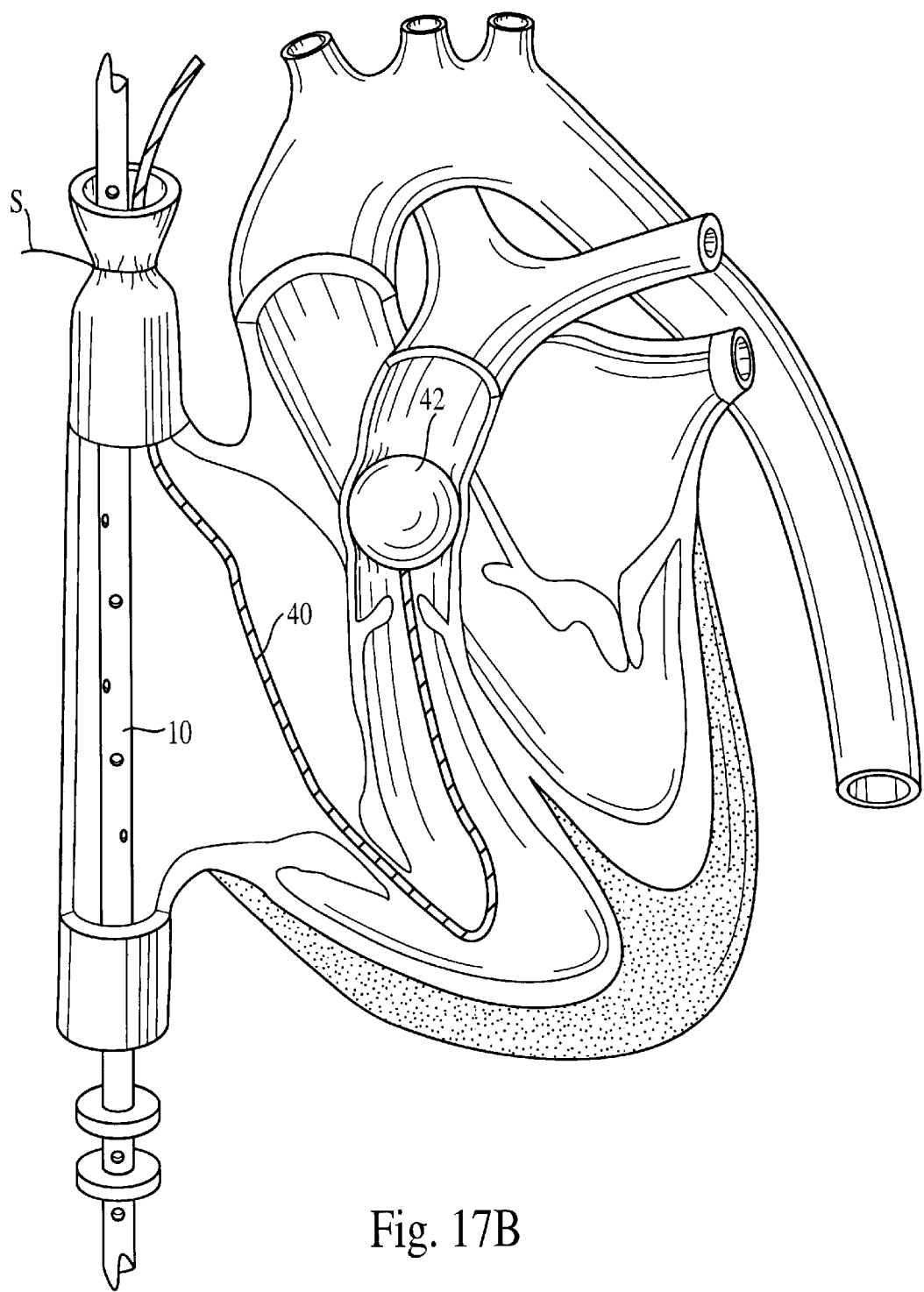

Alternately, the cardiac isolation catheter may have a notch or indentation in the exterior surface thereof which is adapted to the shape of the body of the second catheter. As illustrated in FIG. 17B, the second catheter 40 may be inserted into the vena cava independently of the cardiac isolation catheter 10 (and preferably before the cardiac isolation catheter), and aligned such that the body of the second catheter 40 fits into the notch in the cardiac isolation chamber at the point at which the vena cava is seated against the vessel seat of the cardiac isolation catheter.

When the distal tip of the second catheter extends distally beyond the vessel seat, the distal tip may have an orifice which communicates with a lumen extending longitudinally in the second catheter for withdrawing fluid from the lumen of the pulmonary artery. The second catheter may alternately, or also, have one or more ports located proximally with respect to the vessel seat which communicate with a lumen extending longitudinally in the second catheter, for withdrawing fluid from the right atrium, the right ventricle, or the root of the pulmonary artery (i.e. the portion of the pulmonary artery located proximally with respect to the vessel seat). Withdrawal of fluid from the pulmonary artery minimizes fluid flow which may leak past the vessel seat, and therefore further prevents mixing of the cardiac circulation with the pulmonary circulation. Prior withdrawal of fluid from the right atrium, the right ventricle, or the root of the pulmonary artery furthermore prevents mixing of a fluid provided to isolated cardiac circulation with systemic circulation upon re-mixing of the circulations.

In order to isolate cardiac circulation of a subject from both the venous and the arterial circulation of the subject, it is necessary to occlude systemic venous blood flow to the heart through the vena cava, using the cardiac isolation catheter of the invention, to occlude pulmonary arterial blood flow using a second catheter, and to occlude aortic blood flow from the aortic root to the systemic arterial circulation. Substantially any method of occluding aortic blood flow which is known (e.g. clamps, sutures, endoaortic balloons, and the like) or is hereafter developed may be used to occlude aortic blood flow. In order to minimize trauma to the subject, it is preferred that aortic blood flow is occluded using an endoaortic catheter which has an aortic vessel seat and which is positionable within the aorta of the subject such that the vessel seat is located superior to the coronary articles but inferior to the aortic arch (i.e. located proximally, with respect to the heart, to the brachiocephalic artery). By seating the aorta against the aortic vessel seat, the endoaortic catheter is emplaced and fluid flow through the aorta is occluded.

The endoaortic catheter preferably has a liquid access lumen extending longitudinally therein from a proximal portion thereof to a discharge port located distally with respect to the aortic vessel seat. Fluid provided to the liquid access lumen passes through the endoaortic catheter and enters the heart or aorta (depending on the location of the discharge port when the endoaortic catheter is emplaced). Fluid provided to the left ventricle or aortic root flows thence into the coronary arteries, and thence into lesser vessels within the heart.

The endoaortic catheter may also have a vent lumen extending longitudinally therein from a proximal portion thereof to a left ventricle vent port located distally with respect to the aortic vessel seat. The portion of the catheter having the left ventricle vent port therein may optionally be extendible with respect to the emplaced endoaortic catheter, whereby this portion may be extended past the aortic valve and into the left ventricle. Optionally, the discharge port and the left ventricle vent port may have a fixed location, relative to one another, such that, upon emplacement of the endoaortic catheter, either both ports are located in the left ventricle or the discharge port is located in the aortic root and the left ventricle vent port is located in the left ventricle. Withdrawal of fluid through the left ventricle vent port can minimize retrograde flow of the fluid across the bicuspid valve and prevent retrograde flow of the fluid into the pulmonary veins.

The vessel seats of the catheters described herein may have any of a number of forms, as is well known in the art The vessel seats may be elements (e.g. balloons) which occlude a vessel without the need for an extravascular element, or they may be elements (e.g. raised portions of the catheter body) which are designed to occlude a vessel in conjunction with an extravascular element (e.g. an extravascular clamp or snare) which seats the vessel against the vessel seat. Exemplary vessel seats include, but are not limited to, balloons, raised portions of the catheter body, expandable portions of the catheter body, indentations into the catheter body, rough or irregular portions of the catheter body, a pair of closely-spaced raised surfaces, or the like. When a balloon is used, it is important that the catheter have an inflation lumen 28 in communication with the interior of the balloon, for inflating the balloon with a fluid (e.g. air or phosphate-buffered saline). The catheters may also comprise one or more suction ports associated with a vessel seat, whereby upon application of suction to the suction port (i.e. via a suction lumen), the wall of the vessel in which the catheter is located is caused to seat more firmly against the vessel seat. The important characteristic of the vessel seats is that they provide a support by which, either independently or in cooperation with an extravascular element (e.g. a snare or clamp), the vessel may be occluded.

The catheters of the invention may further comprise one or more detectable indicia, whereby position and guidance of the catheters within the body of a subject is facilitated. The indicia may be indicia which are detectable using any known imaging technique including, but not limited to, fluoroscopic, radiographic, endotracheal echocardiographic, or sonographic techniques. The use of such indicia is well known in the art. The indicia are preferably placed near features of the catheters such as tips, vessel seats, ports, orifices, and the like.

The identities of the materials used to make the catheters described herein are not critical. The catheters described herein may be made from substantially any material which is presently known or hereafter developed for the manufacture of intraluminal catheters. Such materials include, by way of example, a biocompatible material selected from the group consisting of polyethylene, vinyl acetate, a copolymer comprising vinyl acetate, ethylene vinyl acetate copolymer, polyvinylchloride, acrylate, a copolymer comprising acrylate, polymethylmethacrylate, polyethylmethacrylate, polymethacrylate, ethylene glycol dimethacrylate, ethylene dimethacrylate, hydroxymethyl methacrylate, polyurethane, polyvinylpyrrolidone, 2-pyrrolidone, polyacrylonitrile butadiene, polycarbonate, polyamide, a fluoropolymer, polyvinyl fluoride, polytetrafluoroethylene, a copolymer of polytetrafluoroethylene and polyvinyl fluoride, polystyrene, styrene acrylonitrile, a copolymer comprising styrene acrylonitrile, cellulose acetate, acrylonitrile butadiene styrene, a copolymer of acrylonitrile butadiene styrene, polymethylpentene, polysulfone, polyester, polyimide, polyisobutylene, polymethylstyrene, silicone rubber, polyvinyl chloride elastomer, a polyolefin elastomer, a urethane-based elastomer, latex, and synthetic rubber.

The use of "wire-wrapped" catheters (i.e. catheters having a relatively stiff filament associated with, and usually embedded within, the walls of the catheter) is contemplated. Any other method which is known or hereafter developed to prevent kinking or (e.g. suction-induced) collapse of the catheter may also be used.

It is known that the site of the junction between the azygous vein and the inferior vena cava varies significantly among individuals. Depending upon the position at which the azygous vein empties into the vena cava, it may be necessary to occlude the azygous vein in order to isolate cardiac circulation from systemic circulation. Methods (e.g. angiography, etc.) of determining the location of the junction of the azygous vein and the vena cava are well known. If the azygous vein merges with the vena cava at a point that is located between the portions of the superior and inferior vena cavae that are seated against the vessel seats of the cardiac isolation catheter, then it is necessary to occlude the azygous vein prior to providing inflammatory mediator(s) to the cardiac circulation. The azygous vein may be occluded by substantially any method of occluding a blood vessel. By way of example, it may be surgically ligated or clamped, tourniquetted, or a balloon catheter may be threaded through an access port of the cardiac isolation catheter and into the azygous vein, wherein the balloon is inflated.

Although initial embodiments of the catheters described herein were designed to permit isolation of cardiac circulation from systemic circulation for the purpose of providing a gene vector specifically to cardiac, but not systemic, muscle tissue, it is apparent that the apparatus of the invention may be used for innumerable other purposes. Furthermore, with only relatively minor modifications, the catheters of the inventions may be used for an even greater variety of purposes.

By way of example, because the cardiac isolation catheter of the invention was designed to prevent venous blood flow from passing from the vena cavae of a mammal (especially a human) into the right atrium of the human, this catheter may be used in a wide variety of circumstances in which caval blood flow into the right atrium is considered undesirable. In addition to cardiac bypass, as described herein, such circumstances include, but are not limited to, open chest and other, less invasive thoracic (and particularly cardiac) surgical procedures.

Because the cardiac isolation catheter of the invention is emplaced within the vena cavae of a surgical subject, the visibility of a site anatomically near the vena cava can be improved, relative to prior art surgical procedures at such sites, by using the cardiac isolation catheter to divert, minimize, or occlude venous blood flow through the vena cava. Furthermore, because the cardiac isolation catheter of the invention can comprise one or more access ports by way of which a surgeon may provide apparatus (e.g. catheters, small surgical instruments, and the like), compositions (e.g. pharmaceutical compositions, imaging agents, gene vectors, or the like) to the interior of the venous cavities of the heart (i.e. the right atrium, the right ventricle, the pulmonary artery, and the coronary sinus) without making an incision in the myocardium. Other surgical procedures in which the cardiac isolation catheter of the invention may be advantageously employed include, but are not limited to, mitral valve surgeries, repair of tricuspid valves, treatment of atrial septal defects, and other heart disorders, as is evident to the skilled artisan in light of the present disclosure. By way of example, the cardiac isolation catheter of the invention may be used in place of a pair of single-stage cannulae inserted at the surgical site, thereby providing the surgeon with a less cluttered view of the surgical site and reducing the number of incisions required at the site.

The cardiac isolation catheter of the invention, used together with any of a variety of known endoaortic catheters (and optionally with any of a variety of known azygous vein occluders), can effectively isolate the cardiac circulation from the non-cardiac, non-pulmonary systemic circulation of a mammal. Furthermore, using an endopulmonary artery catheter, as described herein, to occlude fluid flow through the pulmonary artery, the cardiac circulation may also be isolated from the pulmonary circulation of the mammal. Such methods advantageously provide the practitioner with the opportunity to deliver agents specifically to the non-cardiac, non-pulmonary systemic circulation, to the combined cardiac and pulmonary circulation, or to the isolated cardiac circulation. The skilled artisan is able to select appropriate agents and appropriate circumstances in which to deliver them specifically to these compartments.

Thus, use of the term "cardiac isolation catheter" is not meant to indicate that the uses of these catheters is limited to situations in which complete isolation of the cardiac circulation from the non-cardiac, non-pulmonary circulation is desired. By way of example, the cardiac isolation catheter may be used without using an endoaortic catheter to divert caval blood flow away from the right atrium without isolating the cardiac circulation.

Figure 21:
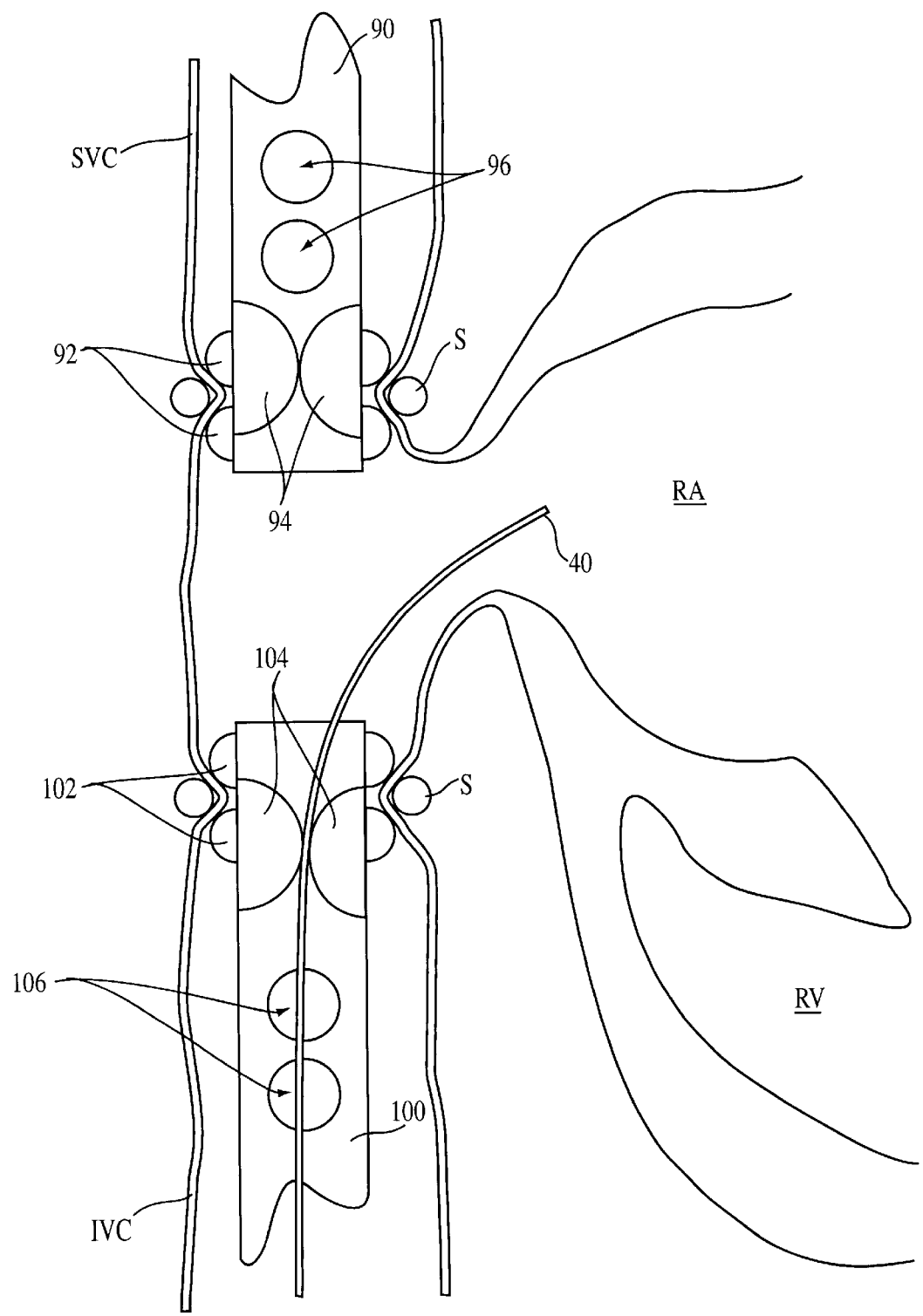
FIG. 21 is a cross-sectional image which depicts an embodiment of the cardiac isolation catheter of the invention, wherein the catheter comprises a pair of caval return catheters 90, 100 which have vessel seats 92, 102 seated against the superior vena cava SVC and inferior vena cava IVC, respectively, by way of snares S. A catheter 40 extends from an access port of one of the caval return catheters into the right atrium RA. Only the distal portions of the emplaced caval return catheters are shown.

An important embodiment of the cardiac isolation catheter of the invention is depicted in FIG. 21. In this embodiment, the cardiac isolation catheter comprises a pair of catheters, herein designated a superior caval return catheter 90 and an inferior caval return catheter 100. Each of these catheters has a vessel seat 92, 102 near the distal end thereof, a venous blood inlet port 96, 106, and a venous blood flow lumen extending longitudinally therein to carry blood from the venous blood inlet port to a proximal portion of the catheter.

This lumen may optionally be connected with an external device, such as a pump, an oxygenating unit, or the like. As depicted in FIG. 21, one or both of the caval return catheters may have an access lumen extending longitudinally therein from an access port to a proximal portion of the catheter. The access port may be at the distal tip of the catheter, as shown in FIG. 21, or it may be elsewhere, but preferably on a distal portion of the catheter. Compositions or apparatus (e.g. a second catheter 40, as described herein) may be passed through the access lumen and the access port into the heart of the subject, or into a portion of the subject's vena cava, depending on the position of the access port.

The access port preferably has a penetrable seal disposed within the access lumen, optionally at the access port. This penetrable seal 104 permits passage of an apparatus or composition in the distal direction along the access lumen, but does not permit fluid flow in the access lumen in the direction from the distal end of the catheter toward the proximal end. A wide variety of penetrable seals may be used, including both single-use and re-usable seals. By way of example, the penetrable seal may be a wax, paraffin, or rubber septum or one or more inflatable balloons. When a balloon is used as the penetrable septum, it is preferably connected with an inflation lumen that is separate from any other inflation lumen in the catheter, and is also preferably deflated to permit passage or movement of a composition or apparatus through the access lumen and inflated to prevent proximal fluid flow.

Figure 19A:
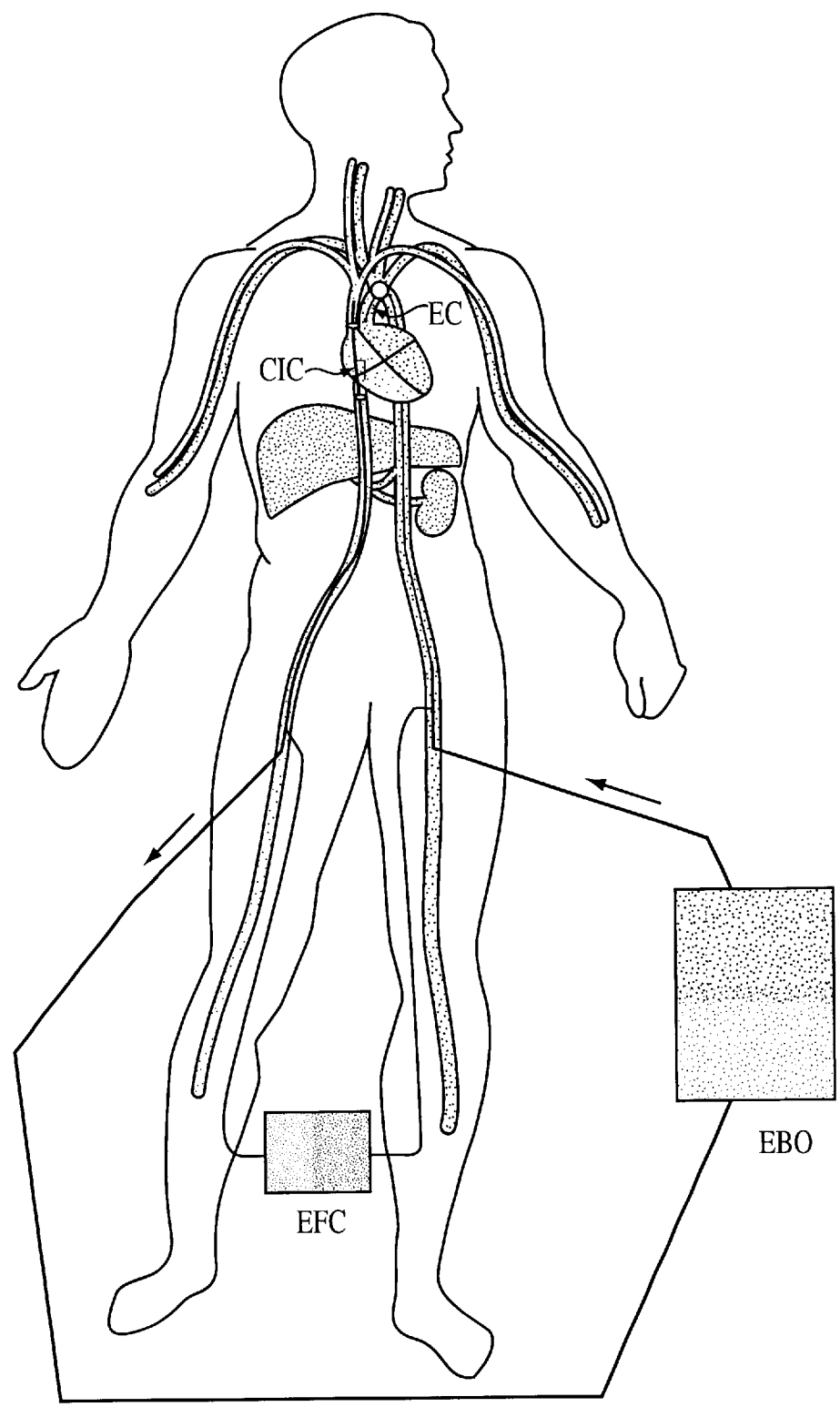
FIGS. 19A and 19B is a pair of diagrams of the arrangement of equipment in embodiments of the cardiac circulation isolation method described herein.
Figure 19B:
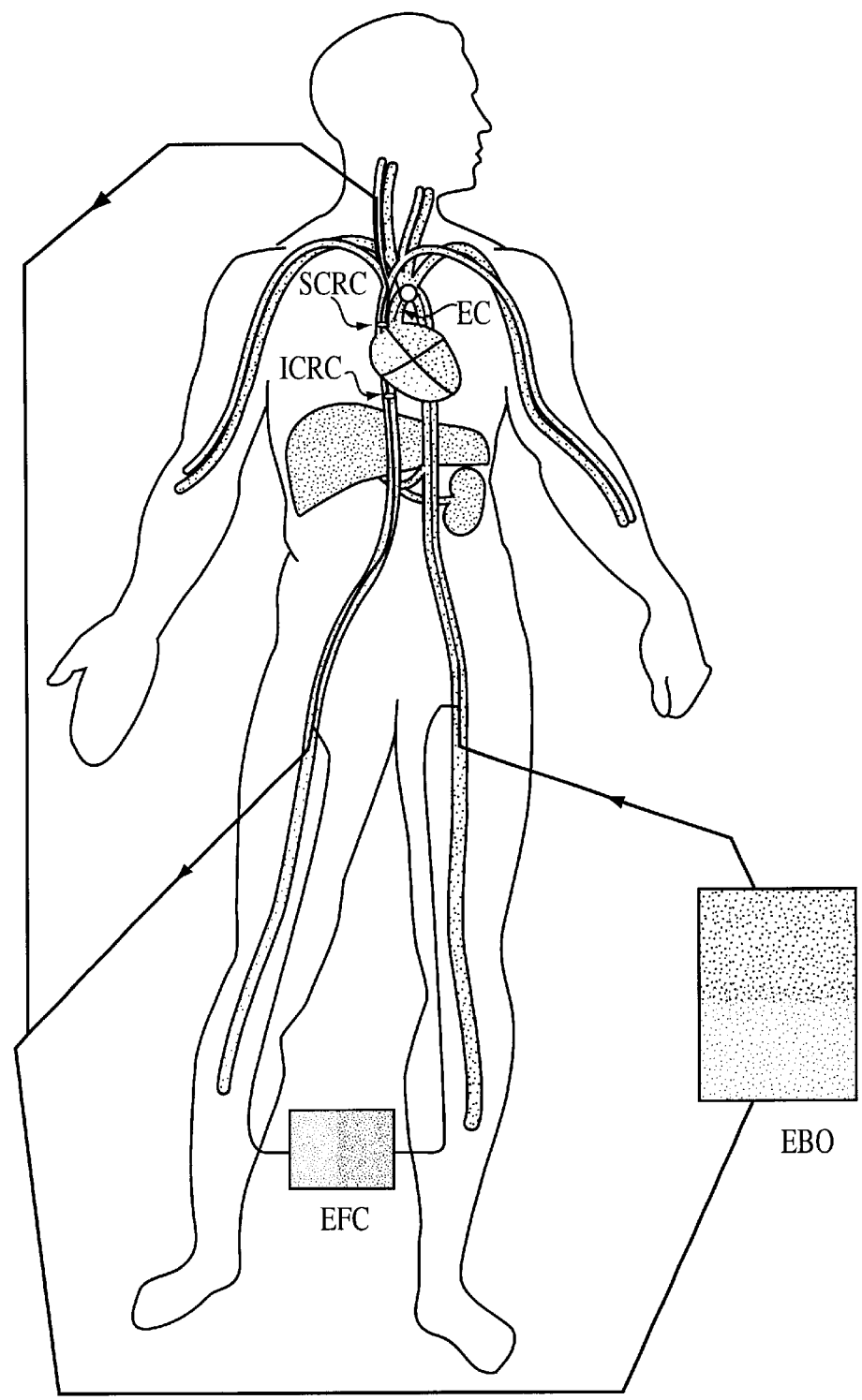
Figure 20A:
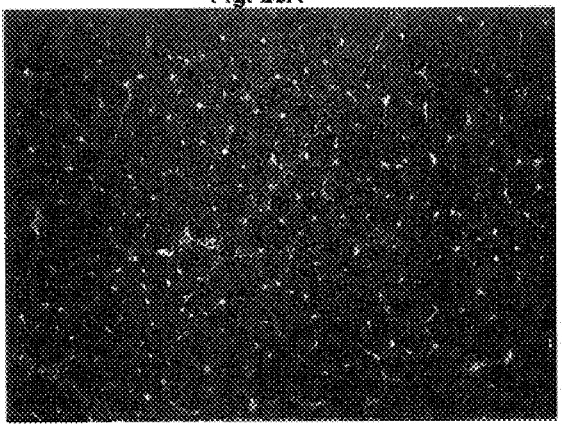
FIGS. 20A, 20B, 20C, and 20D, is a quartet of images which depict Evans blue dye labeling of canine myocardial and diaphragm tissue following delivery of Evans blue dye-labeled albumin to the isolated cardiac circulation of dogs. Diaphragm tissue is depicted in FIGS. 20A and 20B, at different magnifications. Myocardial tissue (left and right ventricular myocardium) is depicted in FIGS. 20C and 20D.
Figure 20B:
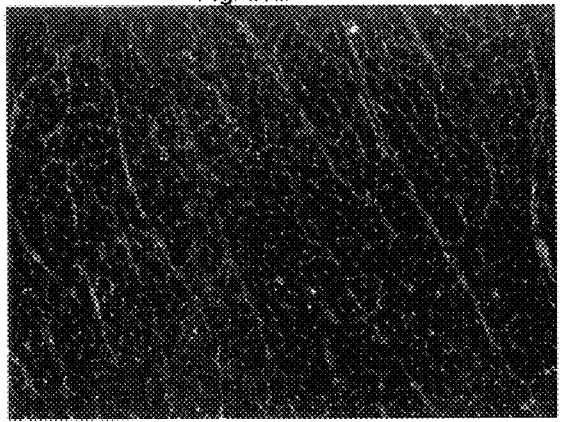
Figure 20C:
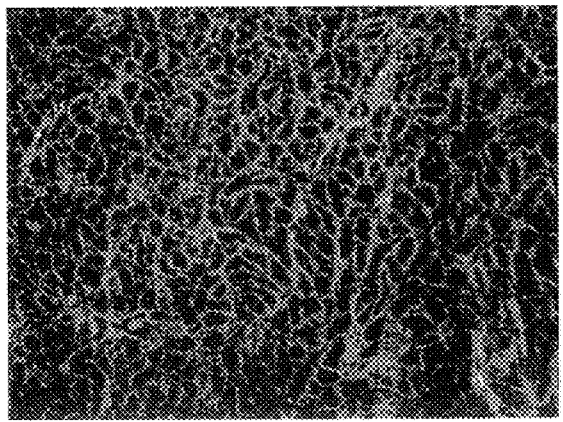
Figure 20D:
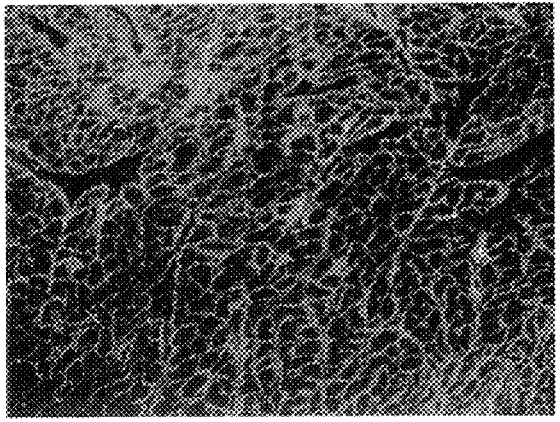

Use of an emplaced superior caval return catheter and an emplaced inferior caval return catheter in the cardiac isolation method of the invention, for example, is illustrated in FIG. 19B. As indicated in this Figure, the superior caval return catheter is emplaced by way of the right jugular vein of the subject and the inferior caval return catheter is emplaced by way of the right femoral vein of the subject. Both caval return catheters are connected with the venous limb of an extracorporeal blood oxygenating unit, and the inferior caval return catheter has an access port located distal to the vessel seat thereof which collects fluid from the heart and delivers it, by way of an access lumen extending longitudinally within the inferior caval return catheter, to the venous limb of an extracorporeal fluid circuit.

In an analogous fashion, a cardiac isolation catheter of the invention may be used in conjunction with a standard femoral or jugular venous catheter, in order to enhance uptake of venous blood from the vena cavae of a subject. This may be particularly advantageous in situations in which the caval anatomy of the subject does not permit use of a cardiac isolation catheter having a size sufficient to efficiently remove venous blood from the subject's vena cavae. In such situations, the cardiac isolation catheter is emplaced as described herein (i.e. with one vessel seat in the superior vena cava and the other in the inferior vena cava, and with the catheter extending between the two vessel seats) through either a femoral or a jugular vein of the subject, and the standard catheter is emplaced in another vein, preferably the vein in which the distal end of the cardiac isolation is emplaced. The venous blood uptake lumen and a lumen in fluid communication with a port at the distal end of the standard catheter are both connected to the venous limb of an extracorporeal oxygenator. The rate at which the subject's venous blood can be provided to the oxygenator is thereby enhanced.

The catheters described herein, particularly the cardiac isolation catheter of the invention, may be provided as a component of a surgical kit for isolating the heart of a mammal from the systemic circulation of the mammal. Such a kit could, for example, comprise (a) cardiac isolation catheter of the invention;

(b) a second catheter insertable within the cardiac isolation catheter for occluding the pulmonary artery of the mammal; and (c) an endoaortic catheter for occluding the aorta of the mammal.

The kit may further comprise additional components and compounds which would be useful for isolating the cardiac circulation of the mammal or for performing the methods described herein. Such additional components and compounds include, but are not limited to:

(d) one or more a cannulae for connecting the mammal's systemic circulation to an extracorporeal blood oxygenating unit;

(e) a pump for withdrawing blood from the venous blood flow lumen of the cardiac isolation catheter and providing blood to the arterial blood flow lumen of the cannula;

(f) a blood oxygenator for oxygenating blood removed from the mammal;

(g) an azygous vein occluder (e.g. a hemostat, a cross clamp, a balloon catheter, or a tourniquet);

(h) an inflammatory mediator such as a vascular permeability-enhancing agent (e.g. histamine) or a vasodilating agent (e.g. papaverine).

Definitions

Certain terminology is used herein as follows.

An "extravascular tissue" is a tissue which is located in sufficient proximity to a blood vessel that exudation from the vessel under conditions of high vascular permeability is capable of contacting the tissue. By way of example, muscle tissue, being highly vascularized, is an extravascular tissue because muscle cells are located in close proximity to blood vessels, and exudate from those blood vessels is capable of contacting muscle cells.

A "vascular permeability-enhancing agent" is a composition of matter which, when supplied to a blood vessel of a mammal, preferably a mammal, increases the permeability of the endothelial layer of the vessel, such that substances within the vessel may pass through the endothelial layer.

A "vasodilating agent" is a composition of matter which, when supplied to a blood vessel of a mammal, preferably a mammal, increases the luminal diameter of the vessel. Stated another way, a vasodilating agent, when administered to a blood vessel of a mammal, increases the caliber of the vessel.

The "perfusion pressure" within a blood vessel means the peak pressure differential between the fluid within the lumen of the vessel and the fluid surrounding the vessel. It is understood that the peak pressure within the vessel corresponds to the driving force for blood flow through the vessel by the beating action of the mammal heart.

The "normal physiological" perfusion pressure within a blood vessel means the perfusion pressure within the vessel of a healthy mammal in a resting state.

An "oxygen-transporting agent" means a composition of matter which, when in a liquid or solution form, is capable of capturing an oxygen molecule ($O_2$) and delivering the oxygen molecule to a biological oxygen carrier such as hemoglobin or myoglobin. By way of example, numerous synthetic blood substitutes and perfluorochemical liquids are oxygen-transporting agents.

The term "pharmaceutically-acceptable carrier" means a chemical composition with which a composition of the invention may be combined and which, following the combination, can be used to administer the composition of the invention to a mammal, preferably a mammal.

A "supraphysiologic level" of a vascular permeability-enhancing agent is the level of such an agent which is present in a mammal which is at rest and which is experiencing normal circulatory homeostasis.

By describing two nucleic acid sequences as "operably linked" is meant that a single-stranded or double-stranded nucleic acid moiety comprises each of the two nucleic acid sequences and that the two sequences are arranged within the nucleic acid moiety in such a manner that at least one of the two nucleic acid sequences is able to exert a physiological effect by which it is characterized upon the other.

A "macromolecular assembly" means a molecule or plurality of molecules, wherein the molecule or plurality of molecules is sufficiently large that it not capable of passing through the endothelial layer of a blood vessel of a mammal, preferably a mammal, and more preferably a human, in the absence of a supraphysiologic level of a vascular permeability-enhancing agent. By way of example, a macromolecular assembly may be a single-chain protein, a multimeric protein, a liposome, a linear nucleic acid, a virus such as an adenovirus, a picornavirus, or an adeno-associated virus, a gene vector such as a plasmid or a virus vector, or the like. Also by way of example, the macromolecular assembly may be an adenovirus vector comprising a human minidystrophin gene, as described (Ragot et al., 1993, Nature 361:647–650). Further by way of example, the macromolecular assembly may be an adenovirus vector comprising plasmid pAdDeltaRSV, modified in that the plasmid comprises a full length dystrophin cDNA (Koening et al., 1988, Cell 53:219–228), wherein the pAdDelta RSV plasmid comprises a pBSA-2 vector backbone comprising an RSV promoter operably linked to the dystrophin cDNA, the promoter-cDNA sequence being flanked by adenoviral 5'- and 3'-ITR sequences.

A "gene vector" means a composition of matter which comprises a nucleic acid and which is capable of delivering that nucleic acid to a mammal cell when the gene vector is contacted with the mammal cell. By way of example, a gene vector may be a virus which is capable of infecting a human muscle cell and which comprises a nucleic acid encoding the human dystrophin protein operably linked to a promoter/regulatory sequence, whereby when the virus contacts a human muscle cell, the nucleic acid is provided to the cell, and the cell is capable of expressing the protein.

A "promoter/regulatory sequence" means a DNA sequence which is required for expression of a gene operably linked to the promoter/regulatory sequence. In some instances, this sequence may be the core promoter sequence and in other instances, this sequence may also include an enhancer sequence and other regulatory elements which are required for expression of the gene in a tissue-specific manner.

"Extracorporeal circulatory support" means a mechanical device which is capable of circulating the blood of a mammal through all or a part of the circulatory system of the mammal without assistance from the heart of the mammal. By way of example, a heart-lung machine, which is well known in the art, is a device which is useful for providing extracorporeal circulatory support.

"Venorrhaphy" means surgical repair of a vein, for example by suturing an incision in the vein in such a way as to retain patency of the vein without hemorrhage.

Except as otherwise indicated herein, the "distal" end of a catheter refers to an end of a catheter which is within the body of a subject during use of the catheter. The "proximal" end of a catheter is an end of the catheter with is not within the body of a subject during use of the catheter. It is recognized that catheters generally have a single distal end and a single proximal end, although the use of forked or branched catheters, especially at the proximal end, is recognized as well.

A lumen "extends longitudinally" in or within a catheter if the long axis of the lumen (not including where the lumen communicates with a port in the catheter) is generally parallel to the long axis of the catheter.

A "non-invasively detectable marker" is a composition of matter associated with a catheter, such as with a port or other feature of a catheter, wherein the position of the marker within the body of a subject can be determined using a method which does not require puncturing or incising a tissue of the subject.

A first catheter is "insertable" within the lumen of a blood vessel or within a lumen of a second catheter if the geometric shape of the first catheter permits longitudinal movement of the first catheter within the lumen. When the first catheter is "insertable" within the lumen of a second catheter, it is not necessary that the two catheters be separable (i.e. the first catheter may be permanently contained within the lumen of the second).

A material or lumen is "in fluid communication" with another material or lumen if a fluid may flow from the material or lumen to the other material or lumen without breaching a physical barrier.

A "rod" is an elongate body having a circular or non-circular (e.g. oval, square, rectangular, or irregular) cross-section. A rod may have one or more lumens extending longitudinally therein.

A portion of a catheter, a rod, or a vessel seat is "expandable" if the circumference (including the circumference of catheters, rods, and vessel seats having a non-circular cross section) of the portion may be increased or decreased.

A fluid "oxygenator" is an apparatus which increases the concentration of dissolved oxygen in the fluid.

A "pump" is any fluid displacement device.

An agent is "therapeutic" if delivery of the agent to at least one tissue of a mammal afflicted with a disease decreases the severity of or frequency with which a symptom of the disease is experienced by the mammal.

"Caval" is an adjective which describes one or both of the superior and inferior vena cavae of a mammal, either collectively or individually.

A "notch" is an elongate portion of a surface having a concavity which is significantly greater than the concavity of the surface in general.

A notch is "adapted to fit" a body if the internal geometric shape of the notch is such that the body may be longitudinally moved along the long axis of the notch.

An "imaging agent" is a composition of matter which, when delivered to a cavity, tissue, or surface within a mammalian body, facilitates detection of the cavity, tissue, or surface. Numerous imaging agents are known and described in the literature. By way of example, compounds, the presence of which may be directly detected may be used, such as compounds which emit gamma radiation or which fluoresce, and may be detected using known detection apparatus.

While the invention is described with reference to the following examples, these examples are provided for the purposes of illustration only, and the invention should in no way be construed as being limited to these examples, but rather, should be construed to encompass any and all variations which become evident as a result of the teaching provided herein.

EXAMPLE 1

Convectional Transport of Adenovirus Across the Microvascular Barrier Promotes Systemic Gene Transfer Data which supports the hypothesis that transient hepatic inflow occlusion minimizes unwanted viral sequestration are now presented. The experimental Pringle maneuver was performed on rats which were administered recombinant adenovirus into the central circulation. This resulted in greatly reduced hepatic staining intensity relative to control mammals on which the Pringle maneuver was not performed.

The methods used in the experiments presented in this Example are now described.

Construction and amplification of the E1, E3 deleted recombinant adenovirus vector designated AdCMVlacZ has been described (Kozarsky et al., 1993, Som. Cell Molec. Genet. 5:449–458). Recombinant adenovirus was administered to rats using a total dose of approximately $10^9$ particles per gram of rat body weight. A frozen aliquot of the virus stock, which comprised 10% (v/v) glycerol, was thawed and diluted 1:5 in PBS immediately prior to infusion, yielding a titer of $10^{12}$ particles per milliliter. Mammals were anesthetized by forelimb intramuscular injection of 75 milligrams per kilogram body weight of ketamine and 5 milligrams per kilogram body weight of xylazine. C57B110 mice and Fisher 355 rats were used.

The experiments presented in this Example were designed to investigate differences in convectional transport of a suspension of adenovirus from the lumen of vascular capillaries to the interstitium of muscle tissue, which differences resulted from alterations in the age of the mammal used, the method of providing the suspension to the mammal, the composition of the suspension, or a combination of these factors. Approximately $5 \times 10^{10}$ AdCMVlacZ particles per gram of body weight were administered to all mammals in these experiments. Owing to the outflow resistance of the micropipettes and microcannulae used to administer AdCMVlacZ in these experiments, it is understood that applied infusion pressures are always much higher than the pressures achieved in the vascular beds. Consistency was maintained by using regulated pressures to drive fluid flow through these devices. Tissue specimens obtained from the mammals used in these experiments were whole mount stained for β-galactosidase activity as described (Sanes et al., 1986, EMBO J. 5:3133–3142) following perfusion-fixation with 0.2% (v/v) glutaraldehyde and 2% (v/v) paraformaldehyde in PBS at necropsy. The results of these experiments are summarized in Table 1.

AdCMVlacZ was administered to each of the newborn rats of series A of Table 1 by injecting the virus vector into the retro-orbital vein of the rat using the tip of a glass micropipette, wherein virus vector suspension flow was driven by a picopump under foot pedal control.

AdCMVlacZ was administered to each of the newborn rats of series B of Table 1 by injecting the virus vector into the common femoral artery of the rat using the tip of a glass micropipette, wherein virus vector suspension flow was driven by a picopump under foot pedal control.

AdCMVLacZ was administered to each of the 2 week-old rats of series C of Table 1 immediately following laparotomy and placement of an occlusive vascular clamp across the hepatic inflow vessels. The virus vector was injected into the femoral vein, and the clamp was left in place for 30 minutes before being released.

The 2 week-old rats of series D of Table 1 were intended to serve as control mammals relative to the mammals of series C. The rats of series D were injected with the same amount of virus vector as those of series C, but hepatic inflow occlusion was not performed on the rats of series D.

The adult rats of series E of Table 1 underwent femoral artery and vein isolation and a 3-0 prolene tourniquet was placed at the level of the proximal thigh. Heparin at 100 units per kilogram of body weight was intravenously administered to the blood circulatory system of the each rat, and the femoral artery or each was cannulated using a heat-tapered polyethylene tube (PE 10, Becton Dickinson, Sparks, Md.), the lumen of which was in fluid communication with the lumen of a 30 gauge needle mounted at the end of the tube not inserted into the artery. Following tightening of the tourniquet, microvascular clamps were placed to occlude blood flow through the femoral vessels. Infusion of AdCMVlacZ suspension and a 1 milliliter "chase" volume of PBS through the tube and into the artery was driven by a regulated pressure supply, which provided the virus vector suspension continuously at 20 pounds per square inch gauge pressure. The clamps and tourniquet were left in place from five to forty-five minutes, after which time they were removed and arteriotomy was repaired using 11-0 suture (Sharpoint, Reading, Pa.). The small groin incision was closed using a resorbable suture.

The adult rats of series F in Table 1 were treated the same as the rats of series E, except that the regulated pressure supply provided the virus vector suspension continuously at 80 pounds per square inch gauge pressure.

The mice of series G of Table 1 underwent femoral artery injection, as described for the rats of series B, except that a proximal thigh tourniquet and clamps occluding blood flow through the femoral artery were applied prior to delivery of the virus vector. A 100 microliter aliquot of the virus vector was provided using a glass micropipette, followed by a 1 milliliter aliquot of saline. The aliquots were permitted dwell in the artery for five minutes.

The mice of series H of Table 1 were treated the same as the mice of series G, except that 100 microliters of a solution which comprised either 10 millimolar histamine or 0.3 milligram per milliliter papaverine was provided to the artery immediately prior to infusion of the virus vector.

The mice of series I of Table 1 were treated the same as the mice of series H, except that both histamine and papaverine was administered to each mouse.

The mice of series J of Table 1 were treated the same as the mice of series I, except that venorrhaphy was performed on each mouse immediately prior to release of the tourniquet.

The rats of series K of Table 1 underwent femoral artery and vein isolation, and a 3-0 prolene tourniquet was placed at the level of the proximal thigh. Hindlimb circulation was primed by infusing into the artery a composition comprising either 150 micrograms of papaverine in 500 microliters of PBS at pH 7.4 or 500 microliters of 10 millimolar histamine in PBS at pH 7.4. Five minutes later, $6 \times 10^{10}$ AdCMVlacZ particles suspended in 500 microliters of the composition were infused into the artery, followed by a 1 milliliter chase volume of PBS driven from a reservoir maintained at 80 pounds per square inch gauge. The clamps and tourniquet remained in place for a total of forty-five minutes following which the limb circulation was flushed with 3 milliliters of PBS.

The rats of series L of Table 1 were treated the same as the rats of series K, except that the composition comprised both histamine and papaverine, at the concentrations indicated.

In each of the rats of series M of Table 1, limb perfusion was performed as in the rats of series K, except that two overlapping tourniquets were placed to allow complete isolation with transmuscular placement of two overlapping tourniquets as well as vascular access via the superficial inferior epigastric vessel. This required advancement of a second catheter across a venous valve at the junction of this side branch with the greater saphenous vein. Furthermore, the composition comprised both histamine and papaverine at the concentrations indicated, and venorrhaphy was performed on each rat immediately prior to release of the tourniquets.

Newborn mice pups were anesthetized after feeding to ensure a stomach filled with milk, for the purpose of providing optical contrast. The skin of an individual mouse was incised over the abdominal wall and was reflected laterally to provide access to the rectus abdominus muscle in the distribution of the superior epigastric artery. Through a dissecting microscope at approximately 100×magnification, single erythrocytes were readily visualized as they coursed single-file through the skeletal muscle capillaries. Histamine, papaverine, or both, dissolved in PBS, were applied topically to the capillaries. Video recordings were made against a time line with an attached camera. Similar observations were made in the adult mouse and the adult rat of perfusion in the distal portion of the adductor muscles as they overlie the proximal tibia, again to optimize optical contrast in a thin muscle.

The results of the experiments presented in Example 1 are now described.

A novel system for the study of microvascular dynamics has been used to assess the ability of recombinant human adenovirus vector AdCMVlacZ (which has a Stoke's radius of approximately 70 nanometers; Stewart et al. 1993, EMBO J. 12:2589–2599) to cross the endothelial barrier of mammalian blood vessels in vivo. Several interventions having synergistic effects on microvascular permeability have been identified, and a strategy for efficient gene transfer to the majority of muscle fibers in the adult rat hindlimb has been developed. Given the similarity among mammalian muscle tissues, it is clear that the present system can be used analogously in any mammal, and perhaps even any mammal.

Among gene transfer vectors considered for therapeutic use, recombinant adenoviruses are notable for extraordinarily efficient local gene transfer following intramuscular injection in newborn mice (Quantin et al., 1992, Proc. Natl. Acad. Sci. 89: 2581–2584; Acsadi et al., 1994, Hum. Molec. Genet. 33: 579–584). Adenovirus vectors have been used to transduce gene expression in murine models for several human diseases (Kozarsky et al., 1996, Nature Genet. 13: 54–62; Ragot et al., 1993, Nature 361: 647–650). The muscle mass of the newborn mouse hindlimb comprises approximately 30 milligrams of tissue. Diffusion of adenovirus vector for several millimeters through the immature extracellular matrix of newborn mouse muscle tissue enables transduction of most of the nascent muscle fibers. However, the limitations of focal delivery become apparent in older mice and rats, in which gene transduction effected by intramuscular injection of an adenovirus vector becomes progressively less efficient and remains localized to a volume of several cubic millimeters around the site of injection (Acsadi, 1994, supra).

Adenovirus vector delivery via the intravenous route offers access primarily to the liver, where a discontinuous endothelium is thought to facilitate gene transfer from the vascular space to the parenchymal cell mass (Kozarsky, 1996, supra; Kozarsky et al., 1994, J. Biol. Chem. 268: 13695–13702).

The shortcomings of adenovirus vector delivery via direct injection or intravascular delivery may be overcome by developing adenovirus vector delivery methods which are useful for transepithelial delivery, where possible (e.g. Raper et al., 1996, Pancreas 12: 401–410).

Adenovirus vector transport across the continuous endothelial barrier of skeletal muscle can be described as the sum of three delivery components: convective, diffusive, and vesicular exchange delivery (Weinbaum et al., 1995, Symp. Soc. Exp. Biol. 49:323–345). The classical studies of Starling (1896, J. Physiol. 19:312), Krogh (1919, J. Physiol. 52: 409), and Pappenheimer et al. (1951, Am. J. Physiol. 167:13–28) provide relevant data from experiments with skeletal muscle in which transport rates for solutes of different molecular dimensions and lipid solubilities were quantified.

Figure 1B:
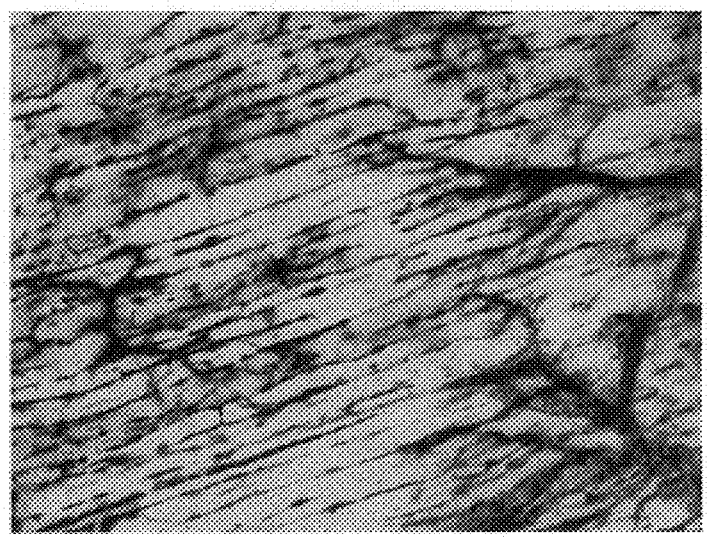
FIG. 1b is an image depicting, at 350×magnification, marker gene activity in the tibialis anterior of an adult rat as assessed by Xgal staining at higher pressure infusion (Table 1 series e).
Figure 1C:
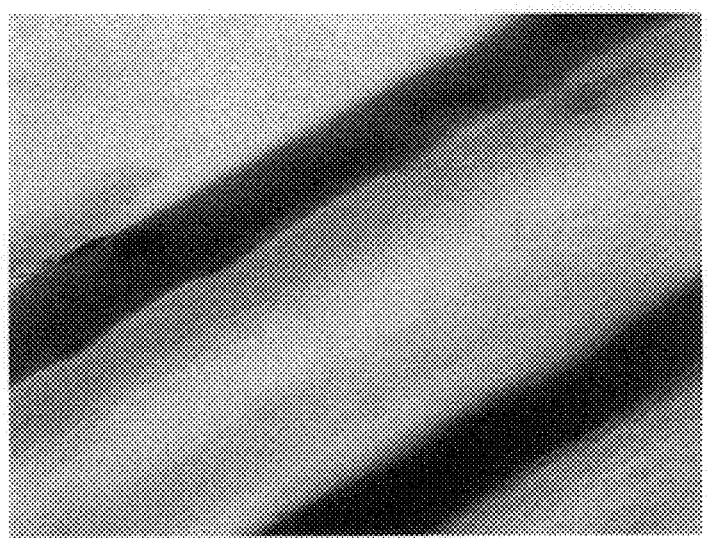
FIG. 1c is an image depicting, at 500×magnification, marker gene activity in the tibialis anterior of an adult rat as assessed by Xgal staining of a whole mount specimen. Focal gene transduction limited to this portion of the tibialis anterior was the result of intramuscular injection of $5 \times 10^{10}$ particles of AdCMVlacZ three days prior to obtaining the image.
Figure 2A:
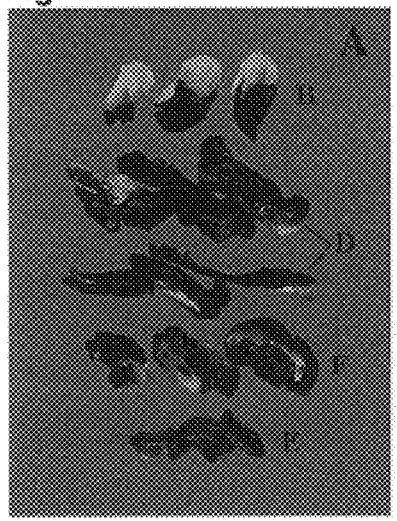
FIG. 2, comprising Panels A–F, is a series of images depicting highly efficient gene transfer to adult rat skeletal muscle fibers following gene vector delivery in the presence of histamine and papaverine. Panel A is an image depicting the entire hindlimb from a rat which was dissected before whole mount staining to expose multiple cross sections. Panel B is an image depicting marker gene distribution in the quadriceps (top row in Panel A) as assessed by light microscopy at 100×magnification. This image illustrates that placement of a tourniquet at the level of the common femoral artery occludes primary blood supply to the rectus femoris. Panel C is an image which illustrates the relative positions of muscle groups depicted in the images shown collectively in FIG. 2. Panel D is an image which depicts, at 25×magnification, the semimembranosus, the adductor brevis, and the adjacent saphenous artery (in the upper right of the Panel). Panel E is an image depicting a 300×Nomarski micrograph of a portion of the tibialis anterior, and depicts the unstained wall of arteriole (in the left center portion of the Panel) and numerous uniformly stained muscle fibers. Panel F is an image depicting, at 25×magnification, the gastrocnemius following gene delivery thereto.
Figure 2B:
Figure 2C:
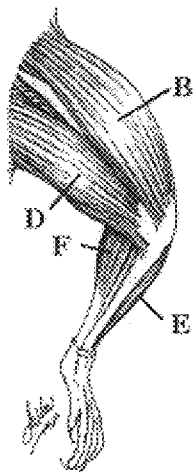
Figure 2D:
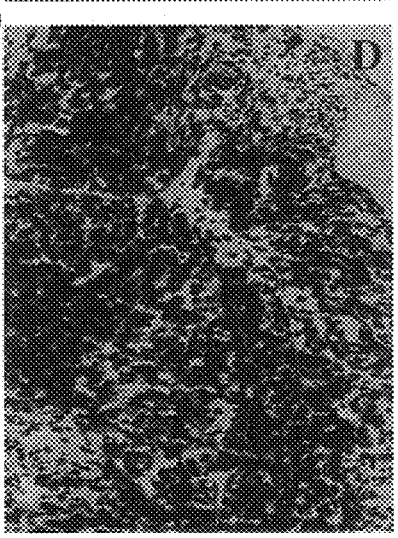
Figure 2E:
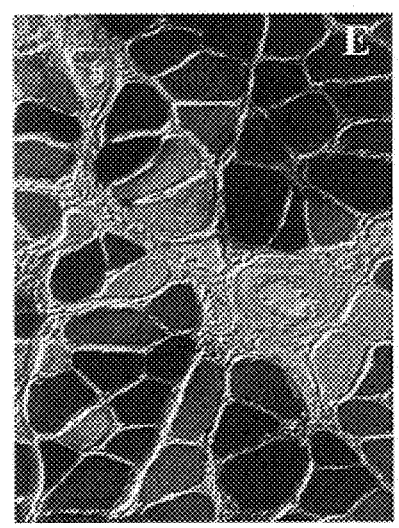
Figure 2F:

The behavior of larger macromolecules was more recently quantified, giving rise to the two-pore theory of transvascular exchange, wherein only one in thirty thousand pores are large enough to admit particles up to a quarter the diameter of the adenovirus (Rippe et al., 1994, Physiol. Rev. 74:163–219). As predicted by extrapolation from these data, recombinant adenovirus administered intravascularly gains minimal access to skeletal muscle fibers, as confirmed by the staining of muscle fiber depicted in FIG. 1a. Intravascular delivery of adenovirus vector was not significantly improved by applying supraphysiologic perfusion pressures simultaneously with vector administration to increase Starling forces in favor of transudation, as indicated by the staining pattern depicted in FIG. 1b and by the data presented in Table 1. These results indicate that the vascular epithelium has remarkable integrity and implies that the rates of vesicular and convectional transport of virus vector to muscle tissue from the interstitium is inconsequential. These results also suggest that intravascular delivery of an adenovirus vector is an inefficient systemic gene transfer strategy.

TABLE 1

EXPERIMENTS ON ADENOVIRUS UPTAKE BY MICROVASCULATURE, LIVER, AND MUSCLE FIBERS FOLLOWING CIRCULATORY DELIVERY

| Series | Species | Age | Infusion Site Devices Used | Infusate | Pressure | n | Xgal Pattern |
|---|---|---|---|---|---|---|---|
| A | Rat | N | IV, Microppt | None | Low | 3 | V+, L++ |
| B | Rat | N | Femoral artery, Microppt | None | Mod | 3 | V+, L++ |
| C | Rat | 2w | IV, Hepatic inflow occlusion | None | Low | 2 | V+, L+ |
| D | Rat | 2w | IV, Microppt | None | Low | 2 | V+, L++ |
| E | Rat | A | Femoral Artery, Cath, Tqt#1 | H | Mod | 3 | V++, L+ (FIG. 1a) |
| F | Rat | A | Femoral Artery, Cath, Tqt#1 | None | High | 3 | V++, L+ (FIG. 1b) |
| G | Mouse | A | Femoral artery Microppt, Tqt#1 | None | Mod | 3 | V+, L++ |
| H | Mouse | A | Femoral artery Microppt, Tqt#1 | H or P | Mod | 2 | V++, L+ |

TABLE 1-continued

EXPERIMENTS ON ADENOVIRUS UPTAKE BY MICROVASCULATURE, LIVER, AND MUSCLE FIBERS FOLLOWING CIRCULATORY DELIVERY

| Series | Species | Age | Infusion Site Devices Used | Infusate | Pressure | n | Xgal Pattern |
|---|---|---|---|---|---|---|---|
| I | Mouse | A | Femoral artery Microppt, Tqt#1 | H + P | Mod | 3 | Lethal |
| J | Mouse | A | Femoral artery Microppt, Tqt#1 | H + P | Mod, D | 1 | V+, L+, M+ |
| K | Rat | A | Epigastric artery, Cath, Tqt#1 | H or P | Mod | 3 | V+, L+, M+ |
| L | Rat | A | Epigastric artery, Cath, Tqt#1 | H + P | High | 1 | Lethal |
| M | Rat | A | Epigastric artery, Cath, Tqt#2 | H + P | High, D. | 9 | M+++ (FIG. 2) |

Abbreviations used:
N: neonate;
2w: two weeks;
A: adult;
IV: intravenous;
Tqt#1: Tourniquet,
Tqt#2: modified (transmuscular) tourniquet;
Microppt: glass micropipette;
Cath: plastic catheter;
D: venous drainage;
H: histamine;
P: papaverine;
V: vascular;
L: liver;
M: muscle;
+: weakly present; ++: strongly present;
Low: 5 psig (Pounds per square inch gauge);
Mod: 20 psig;
High 80 psig.

An alternative approach was investigated, based upon the pathophysiology of inflammation in skeletal muscle, which can be reproduced by topical application of histamine or another vascular permeability-enhancing agent. There is ultrastructural evidence for the transient appearance of gaps between adjacent endothelial cells following application of such an agent to endothelial tissue, the gaps having a width on the order of 1 micrometer. Moreover, electron micrographs document the ability of colloidal HgS particles up to 35 nanometers in diameter and of larger chylomicrons to traverse these intercellular gaps. (Majno et al., 1961, supra).

It was hypothesized that an induced process of inflammatory exudation, would promote vector delivery from the circulation to adult skeletal muscle in vivo by enhancing convectional transport of the vector across the vascular epithelium. The systemic side effects of vasoactive mediator infusions were avoided through the application of an isolated limb perfusion system. As indicated by the data presented in Table 1, the synergistic effects of histamine, papaverine (a potent endothelium-independent vasodilating agent; Wennmalm, 1994, J. Int. Med. 235:317–327), and application of supraphysiologic perfusion pressure resulted in highly efficient gene transfer from the vascular space to the muscle fibers en masse.

The homogeneity of gene transduction in response to these manipulations is depicted in FIG. 2 where Xgal staining of the majority of the muscle fibers in the adult rat hindlimb is visible at several levels of magnification. Although retention of particles smaller than the adenovirus vector at the capillary basal lamina has been documented by electron microscopy (Majno et al., 1961, supra), the results described herein indicate that this barrier has been traversed.

The composite intervention using histamine, papaverine, and suprapysiologic perfusion pressure was lethal if the circulatory isolation of the limb to which the intervention was directed was incomplete. However, mammals in which circulatory isolation of the limb was adequate tolerated the procedure well and returned to normal ambulation.

These results presented in this Example indicate that delivery of an adenoviral vector in conjunction with providing a vascular permeability-enhancing agent, a vasodilating agent, and supraphysiologic perfusion pressure is efficient and well tolerated by mammals. This method of adenovirus vector delivery achieves an efficiency and volume of vector distribution which is essential for gene therapy in numerous genetic diseases such as muscular dystrophy.

The histological appearance of two adjacent muscles of the quadriceps, as depicted in FIG. 2, Panel B, demonstrates the absence of artifactual staining in non-perfused tissue. In FIG. 2, Panel B, blood supply to the rectus femoris was occluded using a tourniquet. The results describe herein also establish the existence of an epimysial tissue barrier to adenovirus diffusion, as depicted in FIG. 2, Panels A and B.

In the experiments presented in this Example, a dramatic reduction in gene delivery to the limb vasculature was also noted, as indicated in FIG. 2, Panels C and D. This observation suggests that the endothelial cells of the muscle tissue vasculature either lost the ability to take up virus as a transient side effect of the mediator infusion or were effectively bypassed by the convectional flow of fluid into the interstitium. This observation further suggests that the method of the invention can be used to deliver an adenovirus vector specifically to an extravascular tissue, without significant uptake of the vector by the endothelial cells of the blood vessel(s) supplying that tissue.

Microvascular perfusion as viewed in real time through a dissecting microscope was initially used to evaluate several pharmacologic agents. Topical application of 10 millimolar histamine rapidly induced vasodilation, and was followed within seconds by progressive capillary stasis. Topical application of 300 micrograms per milliliter papaverine resulted in capillary recruitment and increased local perfusion. Topical application of both agents resulted in sustained perfusion of capillaries, and there was evidence of local edema formation. These findings suggest that the synergistic effects of these mediators on vector delivery relate to the ability of papaverine to overcome the autoregulatory or edema-induced closure of precapillary resistance vessels. The acute toxicity of the mediators noted during inadequate hindlimb isolation relates to their hemodynamic side effects (Thom et al., 1995, J. Clin. Oncol. 13:264–273).

The hemodynamic side effects of the mediators complicates their use in the central circulation during attempted systemic gene delivery (see, e.g., Eyre, 1970, J. Pharm. Pharmacol. 22:104–109; Silverman et al., 1988, J. Appl. Physiol. 64:210–217). Furthermore, concurrent use of adrenergic agonists to support the circulation may reverse the desired effects on gene delivery and/or result in myocardial damage, especially in the setting of cardiomyopathy.

Using the blood vessel occlusion techniques described herein, or other such techniques known in the art, the side effects resulting from systemic delivery of the mediators may be minimized or avoided. In addition, these side effects could theoretically be overcome by the institution of extracorporeal circulatory support prior to the systemic infusion of mediators. In this context, rapid clearance of circulating virus vector by the liver could emerge as a secondary problem. However, the data provided in Table 1 regarding the reduction of hepatic virus uptake by hepatic inflow occlusion suggests that a minimally invasive surgical procedure, such as a laparoscopic procedure, could largely overcome this problem.

The proposed combination of surgical and pharmacological approaches described in this Example represents a general method for systemic gene delivery. The clinical significance of the method is dependent upon how well the procedure is tolerated in larger mammals than those used in this Example. This issue is described further in Example 3 herein.

EXAMPLE 2

Additional Compounds Useful for Enhancing Microvascular Permeability

Compounds which may also function to enhance microvascular permeability in addition to histamine and papaverine, include, but are not limited to, platelet activating factor, serotonin, bradykinin and nitroprusside. Capillary permeability induced following administration of these compounds may be assessed by quantifying the uptake of fluorescently labeled 70- to 100-nanometer-diameter dextran particles.

Given the data which has been described, the invention may be extended as follows.

Systemic gene transfer may be accomplished in large mammals, including humans using a combination of inflammatory and vasodilatory agents provided extracorporeal support is in place.

Provision of adequate circulatory support and oxygenation depends directly on the implications of allometric scaling, i.e., the mathematical relationship which governs the organ function of mammals of different size. Each muscle cell or fiber in the murine heart and diaphragm works about 10–15 times the rate of the human heart and diaphragm. Thus, a heart-lung bypass circuit for small rodents must transport oxygen and blood at 10–15 times the rate needed in humans. The fluid dynamic resistance, as determined by Poiseuille's law, becomes rate limiting because of the wall thickness of the cannulae.

Straightforward solutions to the problem are to perform the experiments in large enough mammals to model the flow rates achievable in humans and to use the paradigms of pediatric and adult cardiovascular and critical care management. The cannulation sites in the mammal will dictate the flow rate. The carotid and jugular approach will be preferentially used because of its minimally invasive nature and because of the fact that it has been used successfully for years even in pediatric extracorporeal membrane oxygenation (ECMO). If necessary, the aortocaval cannulation may be used as it is used in open heart surgery. The types of cannulation and positions of the pump, etc., are illustrated in FIGS. 3, 4 and 5.

It is important to determine whether inflammatory mediators alter the immune response to neo-antigen expression. In addition, it is important to determine the relationship between the level of gene transfer achieved and the magnitude of the physiological disturbance resulting from the initial intervention. In the case of muscular dystrophy, it is known that there is a threshold effect of gene dosage and if it is not possible to achieve this dose, then it is not likely that the procedure will be beneficial. It is possible to compensate for gene transfer inefficiency and enhance the gene therapy effect by using stronger promoter sequences to drive gene expression. Tissue specific expression may also be possible using tissue specific promoter sequences.

It is anticipated that a patient in need of the procedure described herein would undergo general endotracheal intubation anesthesia, would undergo a neck incision as is currently used for extracorporeal membrane oxygenation, and would undergo placement of laparoscopic ports for timely performance of a Pringle maneuver. The flow through the ECMO circuit would commence followed by infusion of vasodilator, then virus and then inflammatory mediator, with flow rates and additional volume used as needed to achieve a hyperdynamic circulation. After completion of a short period of exudation which may be of the order of as little as five minutes, blood would be cleansed of the residual inflammatory mediator to promote rapid weaning from ECMO. This would be accomplished through the use of a cell saver, one or more hemofiltration or hemodialysis units connected in series, or other recovery device. The patient would then be progressively weaned from extracorporeal oxygenation. In the mammal models studied thus far, treated mammals are ambulatory within a short period following surgery.

EXAMPLE 3

Extracorporeal Circulatory Support and Blood Oxygenation in Sheep

The experiments described in this Example were performed to confirm that the circulatory system of a mammal larger than a mouse or a rat can be supported extracorporeally under the conditions described herein for delivery of a macromolecular assembly such as an adenovirus vector. Sheep were subjected to cardiopulmonary bypass, and were then administered either 3.75 or 7.5 milligrams per kilogram body weight of papaverine and either 25 micrograms per kilogram body weight or 125 milligrams per kilogram body weight of histamine. Relevant physiological characteristics of the sheep were monitored in real time.

The materials and methods used in the experiments presented in this Example are now described.

Surgical Procedure

The extracorporeal circulation support system described herein was designed to permit the mammal to tolerate massive fluid exudation under the influence of histamine and papaverine.

Healthy sheep were orally administered a Nichol's prep which consisted of one gram of erythromycin and one gram of neomycin base the night before surgery to minimize intestinal dilatation with air. The sheep were fasted overnight (i.e. at least twelve hours) with ab libitum access to water. The mammals, after constraint using a squeeze cage, were sedated by intramuscular administration of 10 milligrams per kilogram body weight of ketamine and induced for anesthesia using intravenous bolus doses of 30 milligrams per kilogram of pentobarbital. The vocal cords of each were sprayed with 2% (v/v) lidocaine, after which the mammals were endotracheally intubated and connected to a mechanical ventilator. Tidal volume was set at 15 milliliters per kilogram body weight with a respiratory rate of 20 per minute. The mammals were weighed to update records. Anesthesia was started using 3% (v/v) isoflurane and was maintained using 1–2% (v/v) isoflurane.

The depth of anesthesia was determined by lightly pinching the mammal's tail at fifteen minute intervals throughout the procedure. If any antalgic response was noted the mammal was given additional anesthetic by doubling the percentage isoflurane for five minutes and then reverting to the original percentage only when the antalgic response to tail pinch ceased.

Each mammal was positioned in dorsal recumbency and electrocardiogram leads were placed on the extremities. All mammals underwent cannulation as described herein. In addition to access for cardiopulmonary bypass, the cannula was used, after euthanasia, for saline perfusion of the mammal to replace plasma in the vascular space. In all cases the mammals were euthanized after the experimental pump run following barbiturate overdose by disconnecting the ventilator for ten minutes immediately prior to saline perfusion.

The peritoneal cavity was entered through a right subcostal incision and the hepatoduodenal ligament was identified and mobilized. A Rammel tourniquet was placed in position to ultimately occlude the portal vein and hepatic artery, but the clamp was left in the open position. The fascial edges of the abdominal incision were then loosely approximated with towel clips.

A small vertical incision was made over the palpable left carotid pulse and deepened just far enough to allow placement of an arterial catheter for pressure monitoring purposes. A longitudinal incision was then made over the pulse of the right common carotid artery. This incision was deepened to enable full exposure of the right external jugular vein and common carotid artery. A 29-inch wire-wrapped venous cannula was placed in the right external jugular vein and carefully advanced inferiorly until its tip assumed a position estimated to be in the right atrium, wherein the estimate was based on surface landmarks and on the distance the catheter was advanced. Next, a 14-inch wire wrapped cannula was placed in the right common carotid artery. In both cases, vascular cannulation presupposed the achievement of proximal and distal control. The carotid cannula was advanced until its tip assumed a position estimated to be in the aortic root, near the aortic valve.

The left external jugular vein was cannulated with a cordis port, following which a Swan-Ganz catheter was advanced until its tip was in the pulmonary artery. The appropriate ports of the Swan-Ganz were then attached to pressure transducers to allow simultaneous monitoring of pulmonary artery pressure and central venous pressure.

The right groin was then incised longitudinally over the palpable pulse of the right common femoral artery, and a 14 French wire-wrapped cannula was inserted between the proximal and distal control points and advanced against arterial flow retrograde to the point where its tip was in the right common iliac artery.

Once all cannulae were secured into position, they were attached to the circuit of a pump oxygenator primed with a solution which comprised 120 millimolar sodium chloride, 5 millimolar potassium chloride, 3 millimolar magnesium chloride, 24 millimolar sodium bicarbonate, and which was bubbled with a carbogen mixture, comprising 5% (v/v) carbon dioxide and 95%(v/v) oxygen, until a pH of 7.4 was achieved. Throughout the remainder of the experiment, the carbogen mixture was allowed to flow through the bubble oxygenator at an empirically determined rate high enough to ensure a carbon dioxide partial pressure of 40 torr. This served to fix the arterial pH at approximately 7.4 throughout the entire length of the pump run.

One hundred cubic centimeters of blood was drawn into a pair of sixty cubic centimeter syringes, each containing sixty units of heparin. The heparinized blood was quickly centrifuged to separate red blood cells from plasma. The plasma was then mixed with a filtered solution of Evans blue dye in PBS, approximately 0.5 grams of plasma in 5 milliliters of PBS. Hepatic inflow occlusion was achieved by tightening the Rammel tourniquet previously placed around the hepato-duodenal ligament. After one minute of swirling to gently mix the Evans blue dye with the plasma, the plasma was re-mixed with the separated red blood cells and the entire solution was returned to the mammal's blood stream by way of the central venous cordis through the left external jugular vein. Completion of the infusion of the Evans blue dye defined time point $t=-1$ minute. At $t=0$ minutes, bypass was begun at a pump rate of 3 liters per minute. At $t=2$ minutes, the mammal was infused with a bolus of 150 milligrams of papaverine in 5 milliliters of vehicle by way of the distal-most port on the arterial line leaving the pump oxygenator unit. It was anticipated that this potent NO-independent vasodilator would bring about an immediate drop in the blood pressure of the mammal. Over the ensuing two minutes, the mammal's blood pressure was normalized by increasing the flow rate through the pump and infusing an additional volume of the same solution used to prime the pump. At $t=4$ minutes, a bolus of histamine comprising 25 micrograms per kilogram per kilogram was infused intra-arterially through the point most distal from the pump of the arterial line of the pump oxygenator.

After a thirty-minute pump run, the pump was stopped for two minutes to assess the contractility of the heart and to measure the pulmonary-arterial, central venous, and aortic pressures in the absence of extra-corporeal circulation. As soon as these values were obtained, the mammal was humanely euthanized with a massive overdose of barbiturate.

The configuration of the pump oxygenator was altered to permit infusion of a 140 millimolar sodium chloride solution adjusted to pH 7.4 using 10 millimolar Tris hydrochloric acid by way of the arterial cannulae. Immediately prior to exsanguination, the Rammel tourniquet occluding hepatic inflow was released. The venous cannulae was attached to a separate roller pump to allow complete exsanguination of the euthanized mammal into an appropriate receptacle. The mammal was exsanguinated using 10 liters of the sodium chloride solution. Following exsanguination, incisions were made to permit access to the following organs to obtain tissue specimens: heart, lung, liver, kidney, small and large intestine, brain, testicle, and the following skeletal muscles: diaphragm, left and right biceps and triceps from the thoracic extremity, left quadriceps, biceps femorus, gastrocnemious soleus, extensor digitorum longus from the pelvic extremity, iliopsoas, and posterior body wall muscle at point of maximal compression by mammal's body weight against the operating table. The last muscle specimen listed served to establish the variability introduced by the pressure points in positioning the mammal on the operating table.

Each tissue sample was immediately placed in an aluminum foil-wrapped, 50 cubic centimeter conical centrifuge tube having an identifying label. The individual specimens were weighed and a fragment comprising approximately 2 grams of tissue was removed for mincing and for formamide extraction. Evans Blue Dye content was quantitated spectrophotometrically and was normalized to tissue wet and dry weights.

The results of the experiments presented in this Example are now described.

Figure 6A:
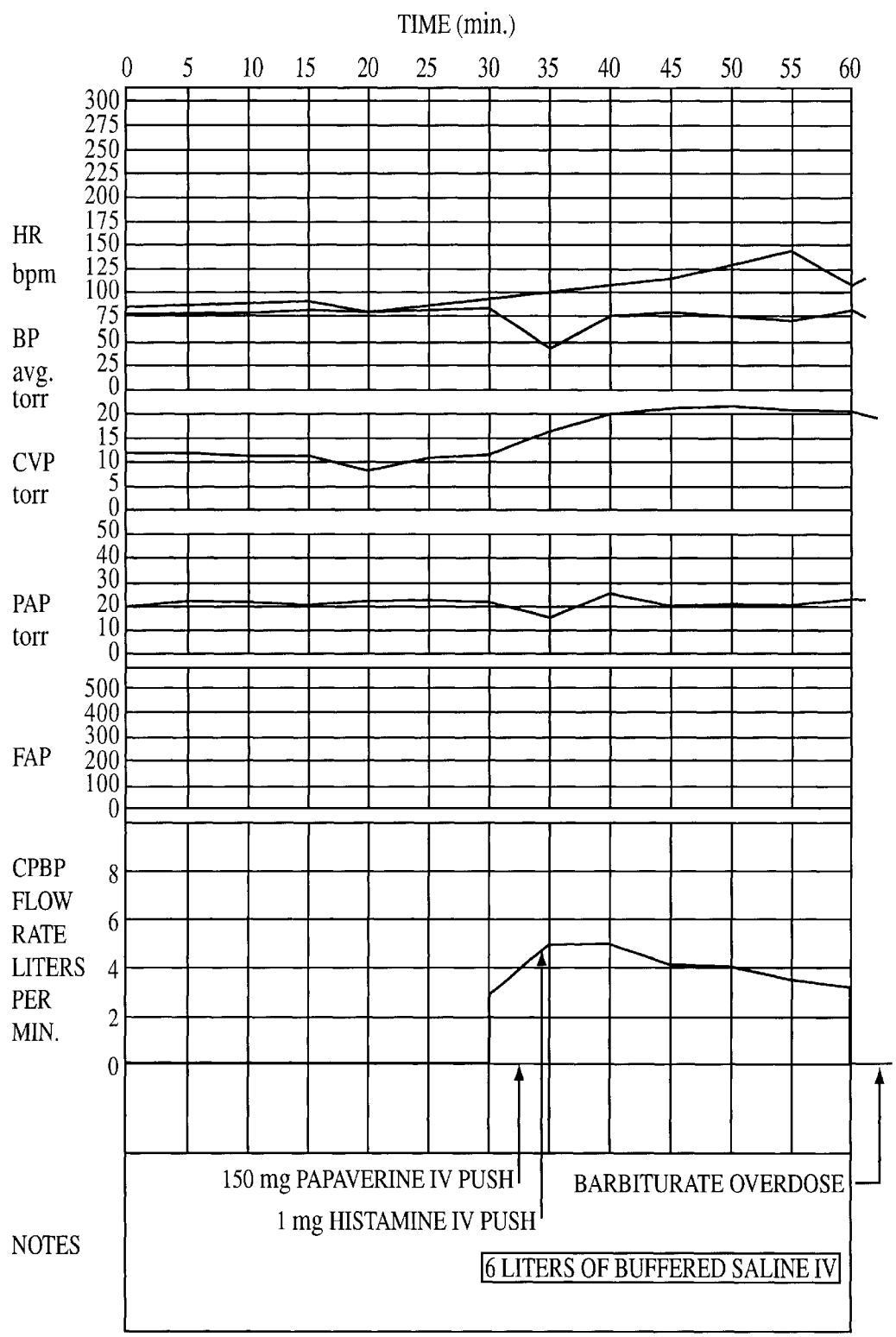
FIG. 6a is a graph which summarizes physiological data obtained from an approximately 40 kilogram sheep to which 150 milligrams of papaverine and 1 milligram of histamine were administered. HR means heart rate in beats per minute. BP means average blood pressure measured in torr. CVP means central venous pressure measured in torr. PAP means pulmonary arterial pressure measured in torr. FAP means femoral arterial pressure measured in torr. CPBP means cardiopulmonary by-pass unit flow rate in liters per minute.
Figure 6B:
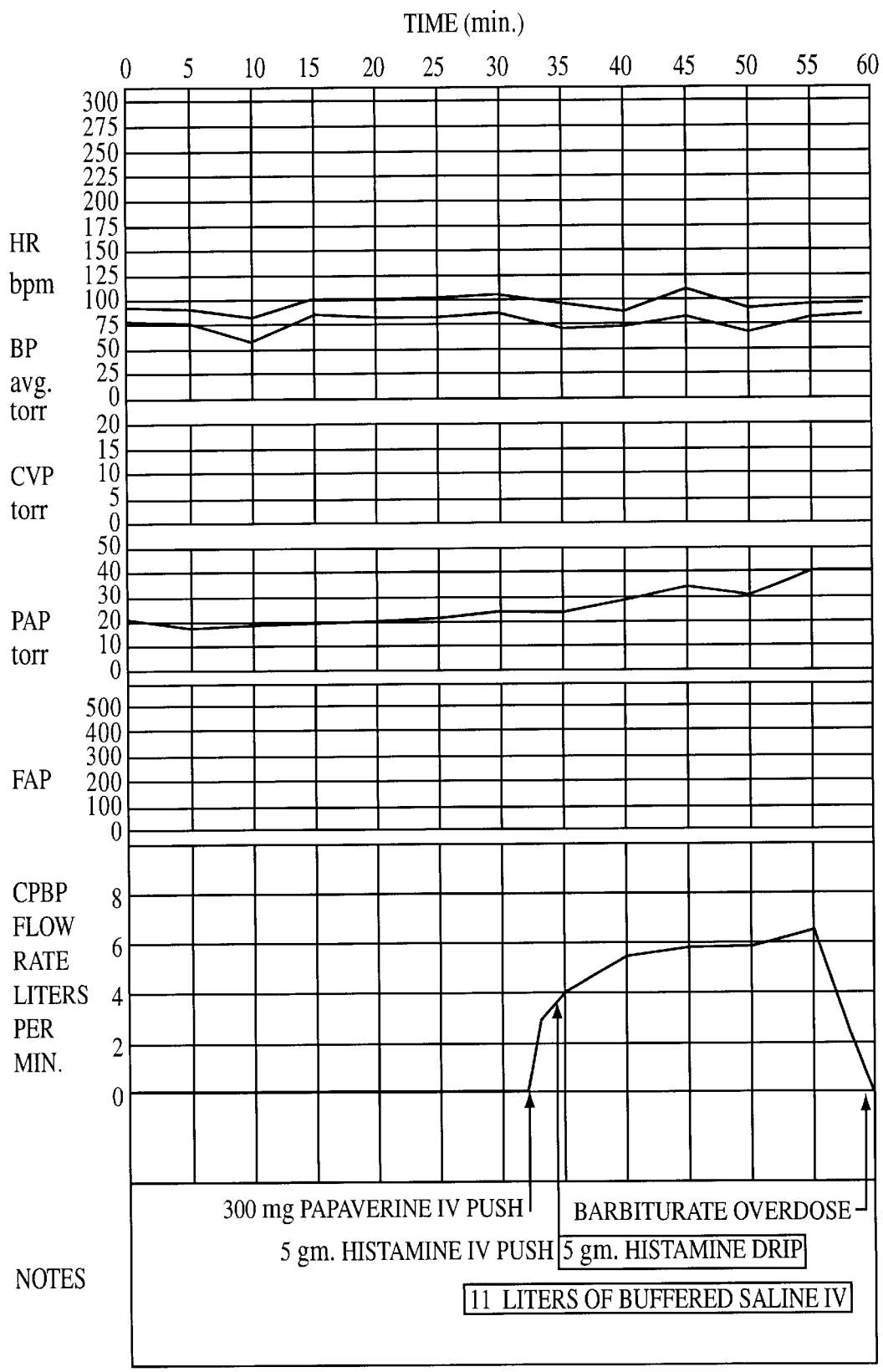
Figure 7:
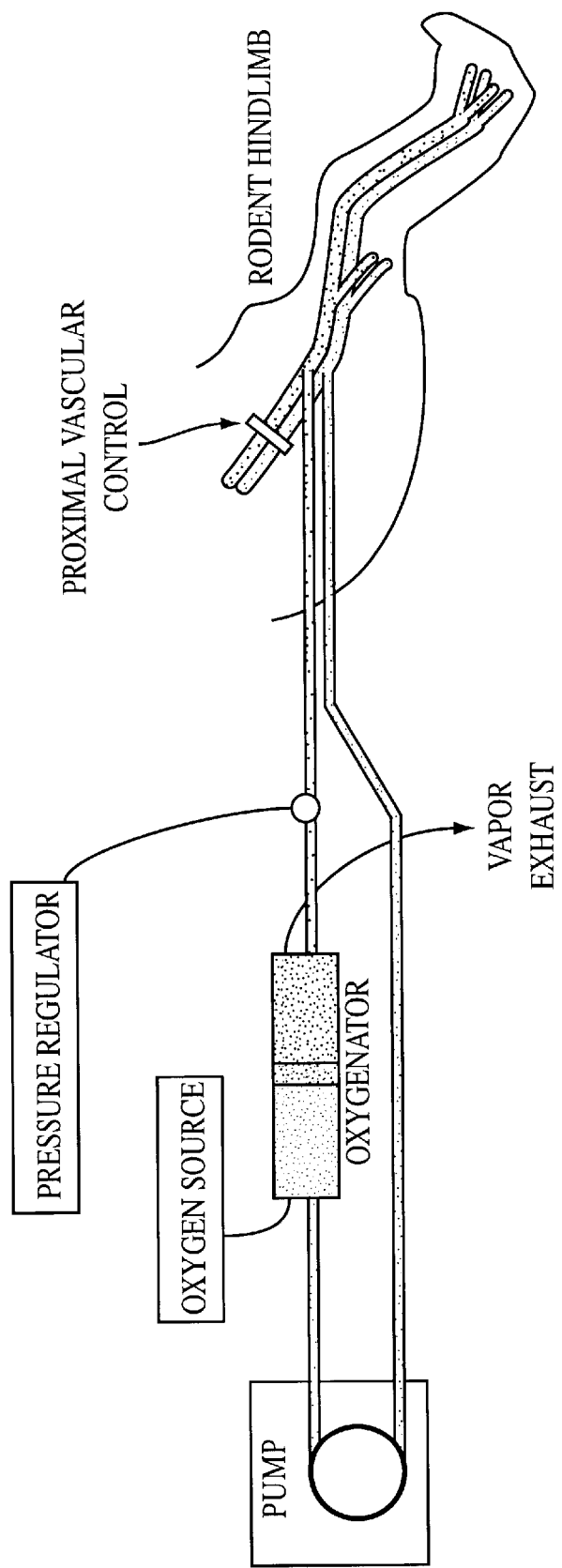
FIG. 7 is a diagram which illustrates the use of a pump, oxygenator, and pressure regulator to deliver a gene vector to an occluded rodent hindlimb. The system operates as follows. An artery and a vein in the rodent's hindlimb are isolated from the rodent's blood circulatory system using a tourniquet or the like. The gene vector is introduced into the artery. A venous catheter connects the vein to the inlet of a pump. The pump passes blood withdrawn from the vein through an oxygenator and into the artery through a second catheter. A pressure regulator maintains a constant perfusion pressure in the artery of the rodent.

The experiments presented in this Example have been performed using two sheep, and the results of those experiments are summarized in FIGS. 6a and 6b.

One 40 kilogram sheep was intravenously administered 150 milligrams of papaverine and 1 milligram of histamine, and physiological data recorded using this sheep are depicted in FIG. 6a. As expected, the blood pressure of the sheep dropped following administration of the vasodilating agent, papaverine, and the vascular permeability-enhancing agent, histamine. However, as depicted in FIG. 6a, the extracorporeal circulatory support system was able to stabilize the hemodynamic state of the sheep to the extent that, from approximately ten minutes after administration of the compounds, the sheep's blood pressure was approximately equal to the blood pressure prior to administration. As noted in the figure, the extracorporeal circulatory support system supplied 6 liters of PBS to the sheep, suggesting that approximately 6 liters of fluid had been exuded from the vascular system of the sheep to extravascular tissues.

A second 40 kilogram sheep was intravenously administered 300 milligrams of papaverine and 5 grams of histamine, and physiological data recorded using this sheep are depicted in FIG. 6b. As expected, the blood pressure of the sheep dropped following administration of the vasodilating agent, papaverine, and the vascular permeability-enhancing agent, histamine. However, as depicted in FIG. 6b, the extracorporeal circulatory support system was able to stabilize the hemodynamic state of the sheep to the extent that, from at least twenty-five minutes after administration of the compounds, the sheep's blood pressure was approximately equal to the blood pressure prior to administration. As noted in the figure, the extracorporeal circulatory support system supplied 11 liters of PBS to the sheep, suggesting that approximately 11 liters of fluid had been exuded from the vascular system of the sheep to extravascular tissues.

These results confirm that the extracorporeal circulatory support system described herein is capable of stabilizing the hemodynamic state of a mammal under the conditions described herein for delivery of a macromolecular assembly such as an adenovirus vector.

Experiments in rats indicated that distribution of Evan's blue dye complexed with albumin is predictive of tissue infectivity by recombinant marker adenoviruses delivered by way of the bloodstream. Following intravascular administration of AdCMVlacZ and Xgal staining, blue color was detectable throughout the liver, but was undetectable in skeletal muscle. When Even's blue, results were similar, with an estimated quantitative ratio greater than 1000:1 distribution between liver and skeletal muscle. It was discovered that performance of the Pringle maneuver decreased this ratio to about 200:1 (liver:skeltal muscle) without increasing uptake by skeletal muscle. This ratio was approximately 6:1 in the sheep to which 150 milligrams of papaverine and 1 milligram of histamine were administered and was approximately 2:1 in the sheep to which 300 milligrams of papaverine and 5 grams of histamine were administered. These data are strongly predictive of widespread global transfer of adenovirus vector to skeletal muscle by way of the vascular space in mammals.

EXAMPLE 4

Transfer of a Human Mini-Dystrophin Gene to Rat Muscle Tissue and Expression Therein The adenovirus vector designated AdCMVΔ17-48dys was constructed as follows. A plasmid comprising the Sal I linkered Δexon 17-48 mini-dystrophin cDNA cloned into pUC18, as described (Acsadie et al., 1991, Nature 352:815–819) was obtained. The plasmid pAdCMVlacZ as described (Kozarsky et al., 1994, J. Biol. Chem. 268:13695–13702), was also obtained. pAdCMVlacZ is a shuttle plasmid comprising map units 0–1 and 9–16 of human adenovirus 5 flanking a cytomegalovirus (CMV)-based transcriptional cassette which drives constitutive expression of the *E. coli* lacZ gene. pAdCMVlacZ was cleaved at a Xho I endonuclease site and the cDNA from the plasmid comprising the cDNA was subcloned in the sense orientation with respect to the CMV promoter of pAdCMVlacZ as a Sal I restriction fragment to yield a plasmid designated pADCMVMini-1.

AdCMVA17-48dys was made by linearizing plasmid pADCMVMini-1 with the unique-site-cutting endonuclease Pvu I and was co transfected with a Cla I-restricted adenoviral genome d1327 into 293 cells, as described (Graham et al., 1977, J. Gen. Virol. 36:59–74). Plaques resulting from growing recombinant viruses were isolated and expanded as described (Graham et al., 1991, In: *Methods in Molecular Biology*, Murray, ed., Humana, Clifton, N.J., 109–128). Lysates from the plaque expansions were used to infect 293 cells which were subsequently collected and subjected to immunofluorescent staining with the primary antibody, NCL-Dys-2 (Novocastra Laboratories, Newcastle upon Tyne, UK). Recombinant viruses that stained positive for the presence of dystrophin in 293 cells were subjected to Western blot analysis, and viruses expressing a mini-dystrophin protein of the expected size were selected for amplification. Following three rounds of purification, the virus stocks were expanded, and adenovirus preparations were generated using standard methods. 293 cells were infected at a multiplicity of infection of about 100 particles per cell, and the transduced cells were analyzed by immunofluorescence and Western blot. These preparations were used in place of AdCMVlacZ in perfusion of rat hindlimbs, as described for the rats of Series M in Example 1 herein.

Figure 11A:
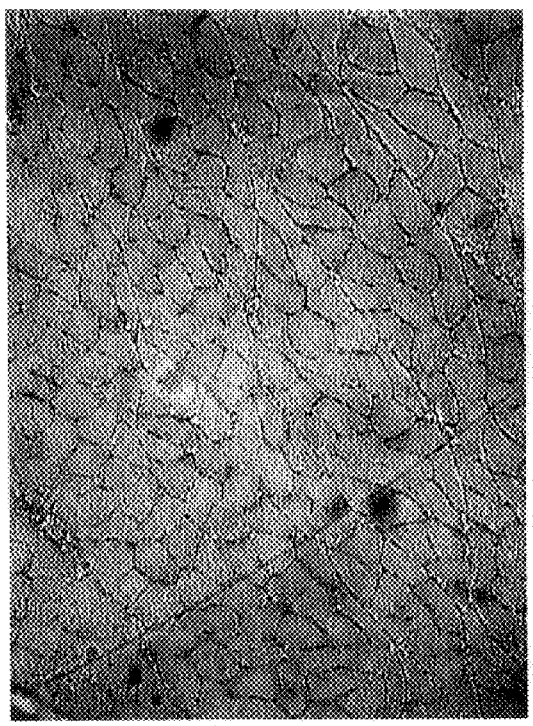
FIG. 11a is an image which depicts a cross-section of a rat gastrocnemius muscle to which the adenovirus vector, AdCMVΔ17-48dys, was delivered and which was immunofluorescently stained using NCL-Dys-2, which is a fluorescently-labeled antibody which specifically binds to an epitope which is present in human dystrophin but which is not present in rat dystrophin.
Figure 11B:
FIG. 11b is an image which depicts a cross-section of a rat gastrocnemius muscle to which the adenovirus vector, AdCMVlacZ, was delivered and which was immunofluorescently stained using NCL-Dys-2.

Cryosections of gastrocnemius muscle obtained from rats one week after perfusion with AdCMVΔ17-48dys were immunofluorescently stained with NCL-Dys-2, which specifically binds to an epitope of human dystrophin, but which does not bind to rat dystrophin. As depicted in FIG. 11a, the vector was delivered to cells of the rat gastrocnemius, and the mini-dystrophin protein encoded by AdCMVA17-48dys was expressed in those cells. Moreover, the staining pattern is identical to that expected for endogenous dystrophin production in the rat cells. Rat gastrocnemius cells to which no virus vector was delivered and rat gastrocnemius cells to which the vector AdCMVlacZ were delivered (as depicted in FIG. 11b) exhibited no immunofluorescent staining using NCL-Dys-2.

The results presented in this Example demonstrate that the compositions and methods described herein are useful for intravascular delivery of a gene vector to mammalian muscle cells and that such muscle cells are able to express a gene delivered thereby.

EXAMPLE 5

Adeno-Associated Virus Vectors for Gene Transfer to Muscle Tissue

As described herein, experiments involving adenovirus-mediated gene transfer to skeletal muscle established that the microvascular endothelium restricts access from the vascular space to muscle fibers in mammals. Histamine (and other vascular permeability-enhancing agents) transiently permeabilizes the microvascular endothelium, thereby inducing a dramatic increase in the efficiency of adenovirus-mediated gene transfer to skeletal muscle, and this effect is greatly augmented by concurrent use of a vasodilating agent such as papaverine. Highly efficient gene therapy has also been demonstrated in isolated perfused cardiac muscle tissue using an adenovirus vector.

Recent demonstrations by others (Xiao et al., 1996, J. Virol. 7:8098–8108; Fisher et al., 1997, Nature Med. 3:306–312) of persistent transgene expression in muscle tissue, following transduction of the tissue using vectors derived from human adeno-associated virus (AAV), suggests that AAV vectors may be useful in the methods described herein for gene transfer to skeletal and cardiac muscle tissues. By way of example, an AAV vector for gene transfer to muscle tissue may comprise a nucleic acid encoding all or a portion of a human sarcoglycan, such as delta-sarcoglycan.

Figure 12:
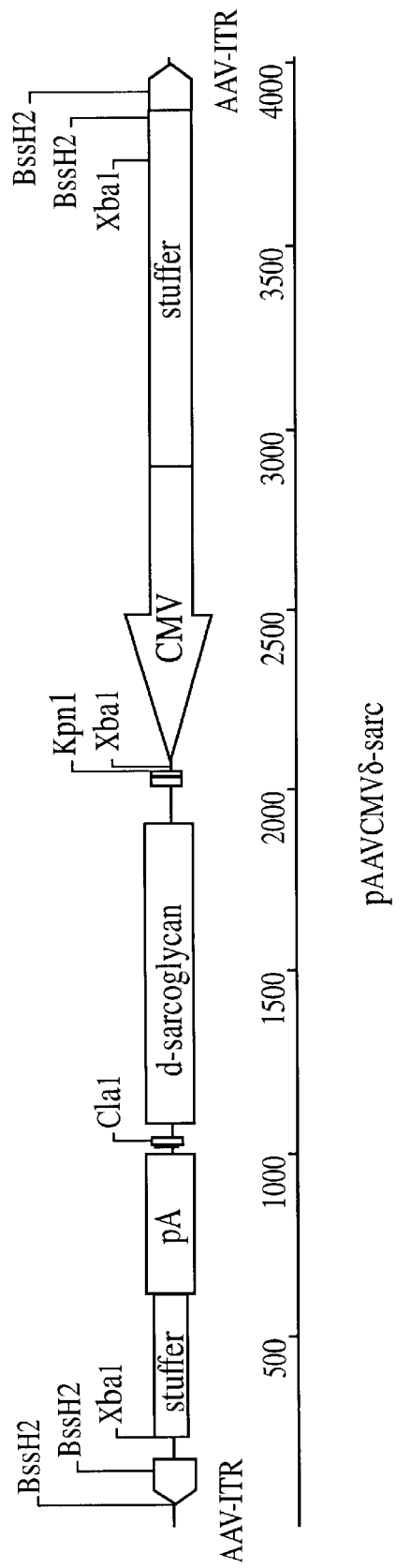
FIG. 12 is a representation of an adeno associated virus gene vector designated "AAV-CMV-delta-sarcoglycan," as described herein.

A vector, herein designated AAV-CMV-delta-sarcoglycan, has been constructed and is depicted in FIG. 12. This vector comprises a copy of the cDNA for human delta-sarcoglycan (Accession #X95191) operably linked with the gene, promoter, and pA regions are interposed between AAV inverted terminal repeats (AAV-ITR), and sufficient "stuffer" DNA is included in the construct to fill the AAV vector capsid. The "stuffer" DNA that was used included part of the 3'-most 500–1000 base pairs of the human embryonic myosin heavy chain cDNA, which is transcriptionally inactive and does not have known transcription factor binding properties in mammalian cells.

The cardiomyopathic Syrian hamster strain designated BIO 14.6 comprises a mutated delta-sarcoglycan gene, and is therefore a mammal model of human limb-girdle muscular dystrophy (Nigro et al., 1997, Hum. Mol. Genet. 6:601–607). In the BIO 14.6 hamster, expression of the mutated delta-sarcoglycan gene leads to formation of inoperative sarcoglycan complexes. By providing the AAV-CMV-delta-sarcoglycan to a muscle tissue of a BIO 14.6 hamster, the sarcoglycan complex in the hamster was 'rescued,' meaning that hamster expressed normal delta-sarcoglycan protein and formed operative sarcoglycan complexes comprising immunofluorescently detectable alpha-, beta-, gamma-, and delta-sarcoglycan.

In cardiac perfusion experiments in which the rodent heart is heterotopically transplanted, contractility of the heart is maintained if cardiac hypothermia is maintained during cardiac muscle endothelial permeabilization and gene transfer. Heterotopic transplantation refers to transplantation of a tissue obtained from one site in a donor animal to a different site in a recipient animal. In this Example, the heart from one rat was transplanted at a femoral position of another rat.

The results of these experiments indicate that AAV vectors may be used to deliver therapeutic gene constructs to muscle tissue using the methods described in the present disclosure. The size restrictions of AAV upon the incorporated gene construct are recognized, but nonetheless permit delivery of gene constructs within the size capacity of AAV virus vectors (i.e. about 1 to 4.5 kilobases). Thus, gene constructs encoding relatively small proteins, or biologically active portions of larger proteins, may be used. By way of example, vascular endothelial growth factor (VEGF) has been implicated as a central mediator in control of endothelial cell proliferation during normal and pathologic angiogenesis (Ferrara et al., 1996, Nature 380:439–442). A VEGF isoform comprising 121 amino acid residues may be encoded by a nucleic acid in an AAV vector, and exhibits the biological activity of VEGF in muscle fibers transformed using such a vector. Furthermore, the 121-amino acid VEGF isoform may be operably linked with a muscle-specific transcriptional cassette (e.g. the muscle creatine kinase promoter/enhancer cassette; Jaynes et al., 1988, Mol. Cell. Biol. 8:62–70) to enhance the specificity of isoform expression to transfected muscle tissue alone.

The results of the experiments described in this Example also suggest the usefulness of maintaining cardiac (or whole-body) hypothermia while performing gene transfer to cardiac muscle tissue isolated from systemic circulation.

EXAMPLE 6

Delivery of a Gene Vector to Systemically Isolated Cardiac Muscle Tissue in vivo This Example describes a method and device useful to facilitate somatic transfer of genetic material to adult myocardium via the coronary vasculature. According to this method, a separate coronary circulation is established in vivo, which effectively isolates the cardiac circulation from systemic blood circulation. Isolation of cardiac tissue from systemic circulation permits a substantial increase in the efficiency of gene vector transfer to the myocardium because the myocardium may be exposed to the gene vector for a long period, either by prolonged provision of fresh gene vector-containing medium to the myocardium or by recirculation (optionally coupled with oxygenation) of a gene vector-containing medium through the myocardial circulation. A particular advantage of this method is that, as described herein, inflammatory mediators such as vasodilating agents (e.g. papaverine) and vascular permeability-enhancing agents (e.g. histamine) may be included in the medium provided to or circulated within the myocardium without providing those mediators to the systemic circulation in large or harmful amounts. Furthermore, because the cardiac circulation is isolated from the systemic circulation using this method, the pressure within the cardiac circulation may be altered during the procedure without significantly affecting the pressure within the systemic circulation. Therefore, this method permits use of inflammatory mediators in amounts great enough to significantly enhance myocardium-specific uptake of a gene vector, while minimizing the systemic effects of those mediators.

The method is performed using one of at least two different types of cardiac circulation-isolating procedures. An "open-chest" procedure is accomplished using known aortic, venous, and left and right ventricular vent catheters and surgical instruments. A "minimally invasive" procedure is accomplished using a cardiac isolation catheter, as described herein. Regardless of the type of cardiac circulation-isolating procedure used in the method, perfusion of non-cardiac tissue in the subject is maintained using an extracorporeal oxygenator and a blood circulating pump. Venous blood is obtained from the subject, for example, by cannulating the femoral vein of the subject and passed through the oxygenator and pump. Oxygenated blood is provided, for example, by cannulating the femoral artery of the subject, as illustrated in FIGS. 19A and 19B.

Open-Chest Cardiac Circulation-Isolating Procedure

Cardiac circulation may be isolated in vivo using at least two different open-chest surgical procedures. The first of these two procedures is performed as follows.

(i) Via a median sternotomy, purse strings sutures are placed in the proximal ascending aorta, in the distal ascending aorta, in the proximal superior vena cava, and in the right atrium adjacent the inferior vena cava.

(ii) The distal aorta is cannulated, the purse string suture is drawn tight about the cannula, and this distal aortic cannula is connected to the arterial limb of an extracorporeal systemic cardiopulmonary bypass circuit comprising a blood oxygenator and a pump. The distal aortic cannula may, for example, be a 6.5 millimeter curved, metal-tipped Sam's cannula.

Figure 14:
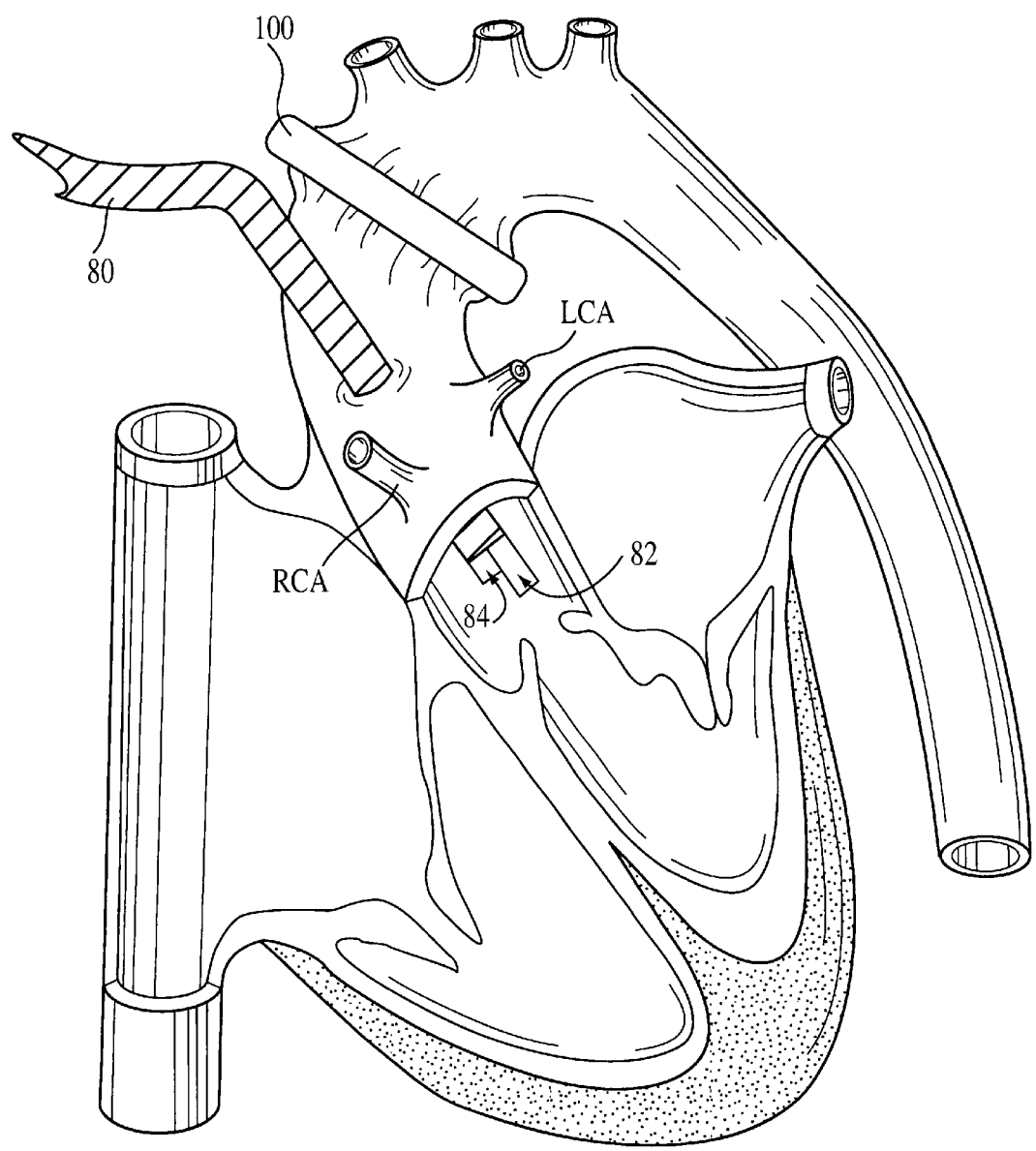
FIG. 14 depicts a human heart having a cannula 80 piercing the aorta thereof and a clamp 100 occluding the aorta. RCA indicates the approximate position of the right coronary artery, and LCA indicates the approximate position of the left coronary artery.

(iii) A proximal aortic cannula (element 80 in FIG. 14; e.g. a standard DLP cardioplegia cannula) is passed through the purse string suture in the proximal ascending aorta, and the suture is drawn tight. A gene vector delivery lumen 82 of the proximal aortic cannula is placed in fluid communication both with the aortic root distal to the aortic valve and with a gene delivery circuit comprising a gene vector reservoir for receiving the gene vector (e.g. a vessel, a piece of flexible tubing, or the like) and a pump for providing fluid to the lumen of the endoaortic catheter. A vent lumen 84 of the proximal aortic cannula is placed in fluid communication both with a pressure relief device (e.g. a reservoir partially filled with a liquid) and with the interior of the aortic root.

(iv) A right-angle venous cannula is placed through the lumen of the purse string suture in the superior vena cava, and a second right-angle venous cannula is placed through the lumen of the purse string suture in the right atrium adjacent the inferior vena cava. The purse string sutures are drawn tight around them, and these two right-angle cannulae are connected, via a Y connector, to the venous limb of the systemic cardiopulmonary bypass circuit. Tourniquets are placed around the portions superior and inferior vena cavae, either at portions surrounding the right-angle cannulae or at portions located between the right-angle cannulae and the right atrium, to allow diversion of all systemic venous return other than that emanating from the coronary sinus and the Thebesian veins into the venous limb of the systemic cardiopulmonary bypass circuit. The tourniquets surrounding the superior and inferior vena cavae are tightened. Thus, all blood returning from the systemic circulation is routed via the superior and inferior vena caval cannulae to the extracorporeal systemic cardiopulmonary bypass circuit, and from there into the distal aortic cannula. Cardiopulmonary bypass is initiated, maintaining the subject's blood at 37□C.

(v) Ventricular vent catheters are then placed in the right ventricle and the left ventricle, These vent catheters are secured with purse-string sutures and are connected, via a Y-connector, to the venous limb of the gene delivery circuit.

(vi) The azygous vein is occluded (e.g. by clamping it, ensnaring it, ligating it, or inflating a balloon in the lumen thereof).

(vii) The ascending aorta is occluded distal to the left and right coronary arteries, for example, using a clamp 100 or by inflating a balloon therein.

(viii) A cardioplegia-inducing solution (e.g. PLEGISOL™) is introduced through the proximal aortic cannula into the myocardium (i.e. via the aortic root), resulting in cardioplegia.

(ix) The pulmonary artery is occluded distal to the pulmonary valve. After each of these steps is performed, oxygenated fluid and/or fluid containing the gene vector is provided through the proximal aortic cannula and perfuses the cardiac circulation via the left and right coronary arteries. The left ventricular vent catheter recovers any coronary arterial flow which is regurgitated across the aortic valve. This portion of the circuit is important if elevated aortic pressures are used to enhance the efficiency of gene delivery to avoid left ventricular distention. All blood or crystalloid returning from the heart via the coronary sinus or the Thebesian veins is routed via the right ventricular vent catheter to the venous limb of the gene delivery circuit. The blood or crystalloid is oxygenated and returned to the cardiac circulation via the proximal aortic cannula.

Figure 13:
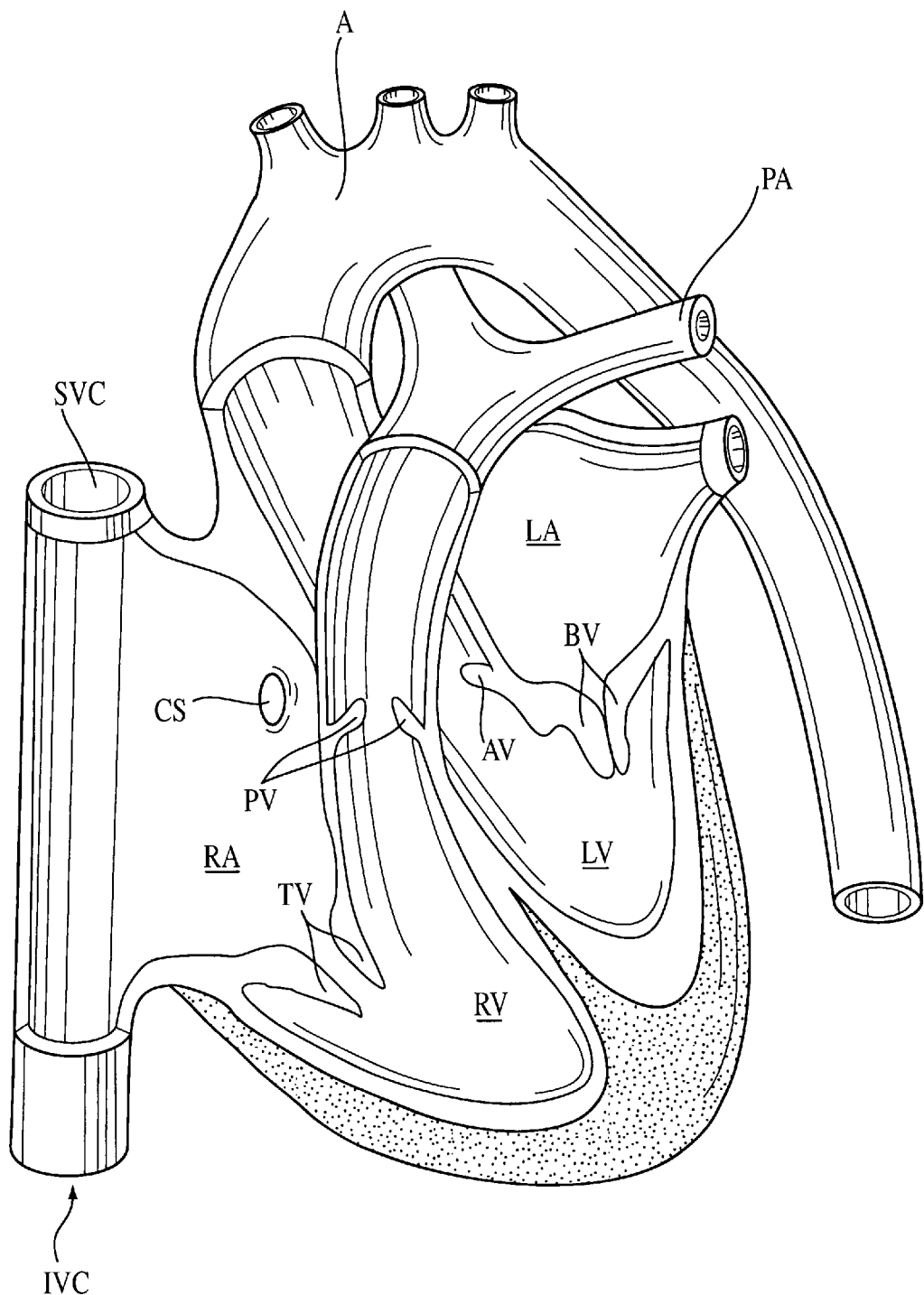
FIG. 13 is a diagram of a human heart, wherein the descending aorta is displaced and several surfaces are removed for clarity. Labels indicate anatomical features as follows: SVC, superior vena cava; IVC, inferior vena cava; RA, right atrium; CS, coronary sinus (only the ostium of the coronary sinus is visible in this view); TV, tricuspid valve; RV, right ventricle; PV, pulmonary valve; PA, pulmonary artery; LA, left atrium; BV, bicuspid valve; LV, left ventricle; AV, aortic valve; A, aorta.

Alternately, the second of the two open-chest surgical procedures for isolating cardiac circulation is performed. This second procedure is substantially the same as the first, except that a coronary sinus effluent catheter is used in place of the right ventricle vent catheter to take up fluid into the gene delivery circuit. The coronary sinus effluent catheter is placed by surgically opening the right atrium after tightening the tourniquets on the superior and inferior vena cavae, to expose the coronary sinus (CS in FIG. 13). A purse string suture is placed circumferentially around the ostium of the coronary sinus. The distal end of the coronary sinus effluent catheter is inserted through the ostium, a balloon on the end of that catheter is inflated, and the purse-string suture is drawn tight, thereby securing the coronary sinus effluent catheter in the coronary sinus. In this second method, the right ventricular vent catheter need not be used, and the pulmonary artery need not be occluded.

Once the cardiac circulation has been isolated from the systemic circulation, inflammatory mediators are infused into the cardiac circulation, together with a gene vector, thereby enhancing the efficiency of egress of the gene vector from the cardiac circulation into the myocardial interstitium and increasing the efficiency of gene uptake and expression by cardiac myocytes. This system permits re-circulation of the liquid containing the gene vector almost exclusively through the cardiac circulation. The liquid may be a oxygen-transporting agent which is capable of containing a high level of dissolved oxygen (e.g. a perfluorochemical liquid) or it may be occasionally or constantly supplemented with an oxygen-containing liquid (e.g. oxygenated blood or crystalloid), in order to permit a longer period of isolation of the cardiac circulation, whereby survival of myocytes and uptake of the gene vector by myocytes are enhanced. The temperature of the fluid in the gene delivery circuit may also be controlled, since temperature also affects the efficiency of vector-mediated gene delivery to the myocardium (e.g. uptake of gene vectors by cardiac myocytes is more efficient at 37□C than at 4–10□C in isolated myocytes and in cardiac myocardium treated ex vivo).

After the cardiac circulation has been isolated for a selected time, gene vector delivery is halted by replacing the liquid containing the gene vector and inflammatory mediator(s) with another liquid which is at least substantially free of the vector and mediator(s). This other liquid may be used to flush the cardiac circulation in a single pass, or it may be recirculated. The tourniquets around the superior and inferior vena cavae and the clamps on the aorta and (when used) the pulmonary artery are removed when the amount of residual vector and mediator(s) is determined or estimated to be at a safe level for systemic exposure. At this point, the systemic and cardiac circulations are merged into a single circulation. The subject is then weaned from cardiopulmonary bypass using appropriate support techniques, such as those described elsewhere herein, and possibly including modified ultrafiltration methods to remove residual mediator(s) and vector from the bloodstream.

The open-chest version of this procedure has been performed in dogs. In preliminary experiments, Evans blue dye-labeled albumin was infused into isolated cardiac circulation in the dogs. Table 2 indicates the subsequent concentration of Evans blue dye-labeled albumin in the coronary and systemic circulations after 20 minutes of cardiac perfusion using the isolation system described above. These results demonstrate that the concentration of Evans blue dye-labeled albumin was approximately 50 to 100 times higher in the coronary circulation than in the systemic circulation, indicating a 98 percent to 99 percent efficiency of isolation of the cardiac circulation in vivo using this approach.

TABLE 2

| Experiment # | Mean Systemic Conc. (μg/ml) | Mean Coronary Conc. (μg/ml) | Systemic/ Coronary Ratio | Efficiency (%) |
|---|---|---|---|---|
| 4 | 1.29 | 125.93 | 97.62 | 98.98 |
| 6 | 0.31 | 17.16 | 46.48 | 97.85 |
| 7 | 0.80 | 36.96 | 55.35 | 98.19 |
| Mean | 0.80 | 60.02 | 66.48 | 98.34 |

FIG. 20 depicts cross-sections of myocardium and diaphragm obtained from dogs that underwent isolation of cardiac circulation in vivo. A cocktail comprising histamine, papaverine, and Evans blue dye labeled-albumin was infused into the isolated cardiac circulation but not into the dogs' systemic circulation circuits. Extensive extravasation of Evans blue dye-labeled albumin into the interstitium between cardiac myocytes, as indicated in FIGS. 20C and 20D, is consistent with specific delivery of the labeled albumin to the cardiac interstitium. In contrast, there is scant staining of the interstitium between skeletal myocytes in the diaphragm, as indicated in FIGS. 20A and 20B. These data indicate that the open-chest cardiac circulation isolation method described herein may be used to effect highly efficient isolation of the cardiac circulation in vivo and that when inflammatory mediators are provided to the isolated cardiac circulation, specific exudation of macro-molecular substances into the myocardial interstitium, but not into the interstitium of systemic tissues such as the diaphragm, is achieved. These results therefore demonstrate the usefulness of this method for providing gene vectors (e.g. plasmids, virus vectors, etc.) to the myocardium.

Minimally Invasive Procedures

Isolation of cardiac circulation may also be achieved using various minimally invasive procedures, in which various catheters are threaded through blood vessels of the subject (e.g. one or more of the jugular vein, the femoral vein, the femoral artery, the superior vena cava, and the inferior vena cava). Because these catheters may be used in place of certain of the cannulae and clamps described herein in the open-chest procedure, these minimally invasive procedures may be performed using only minimal incisions. It is understood that a combination of the methods described in the open-chest procedure and the minimally invasive procedure described herein may be used.

One embodiment of the minimally invasive procedure for isolating cardiac circulation may be performed using known apparatus, such as those of the HEARTPORT® EndoCPB® System (Heartport Inc., Palo Alto, Calif.). In this embodiment, the systemic circulation of the subject is maintained by cannulating the vena cava of the subject (preferably at or inferior to the level of the right atrium) and a femoral artery of the subject. The femoral cannula is connected to the arterial branch of an extracorporeal pump/oxygenator unit, and the venous cannula is connected to the venous branch of the unit. The cardiac circulation of the subject is isolated using a HEARTPORT® Endocoronary Sinus™ catheter, a HEARTPORT® Endopulmonary Vent™ catheter, and a HEARTPORT® Endoaortic Clamp™ catheter.

Figure 18:
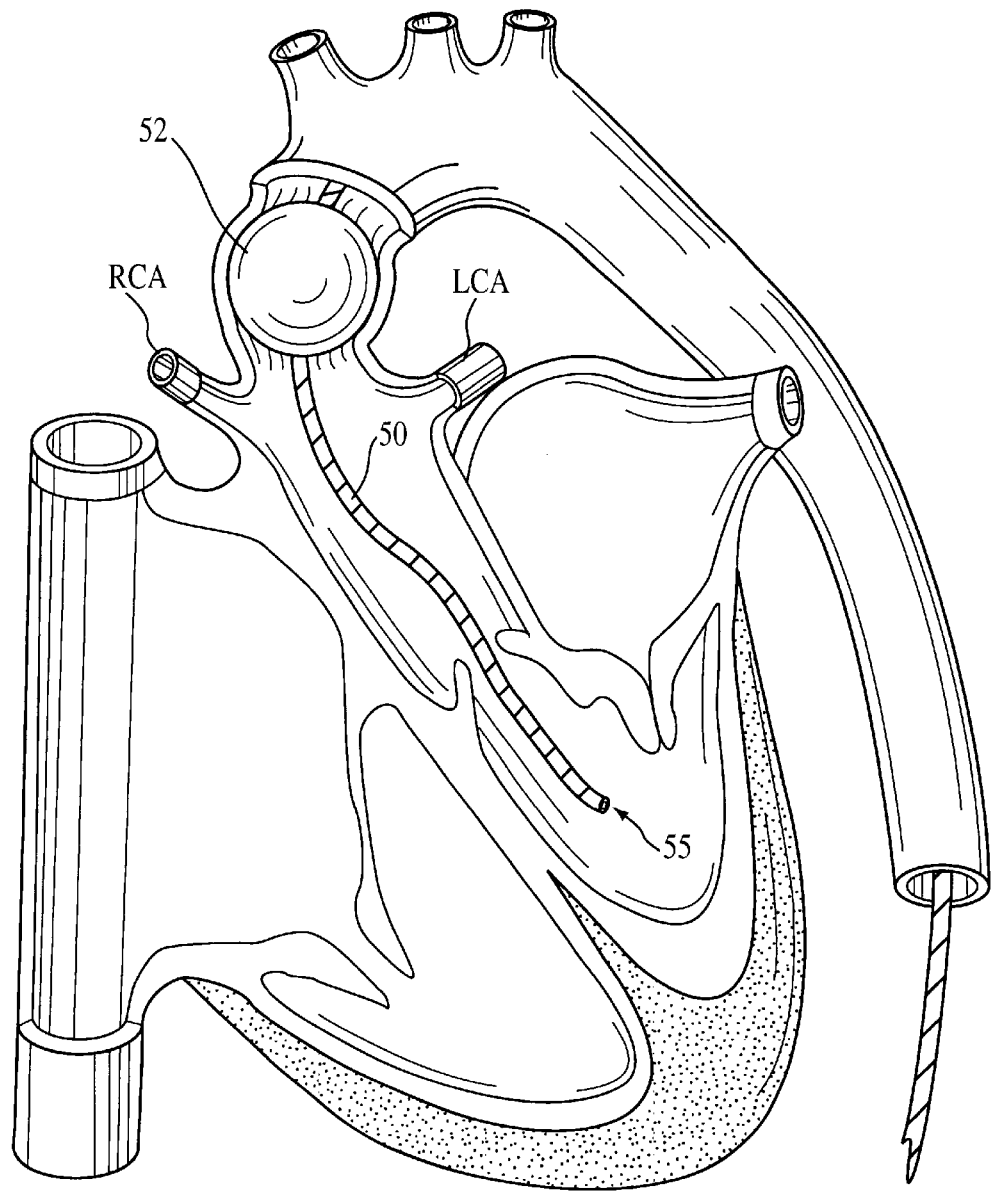
FIG. 18 depicts a human heart having an endoaortic catheter placed within the aortic root thereof, as described herein.

According to this method, the HEARTPORT® Endocoronary Sinus™ catheter is inserted through the internal jugular vein of the subject, through the superior vena cava, into the right atrium, and through the ostium of the coronary sinus. The balloon on the HEARTPORT® Endocoronary Sinus™ catheter is then inflated to secure the catheter in place. The HEARTPORT® Endopulmonary Vent™ catheter is also inserted through the internal jugular vein, through the superior vena cava, and into the right atrium of the subject. This catheter is then guided through the tricuspid valve and into the root of the pulmonary artery, preferably extending proximally through the pulmonary valve. The HEARTPORT® Endoaortic Clamp™ catheter is inserted into the femoral artery of the subject, advanced along the descending aorta, and into the ascending aorta. The balloon of the HEARTPOR® Endoaortic Clamp™ catheter is inflated within the ascending aorta at a level which does not occlude fluid flow from the aortic root into the cardiac arteries but which does occlude fluid flow into the arch of the aorta (i.e. as indicated in FIG. 18). Optionally, the portion of the HEARTPORT® Endoaortic Clamp™ catheter which is distal to the balloon thereof is extended through the aortic valve and into the left ventricle.

Once these cannulae and catheters have been put into place, cardiac bypass is established in the subject using the venous and femoral cannulae. A cardioplegia-inducing solution is provided via the HEARTPORT® Endoaortic Clamp™ catheter to the aortic root, thereby causing the heart to stop beating. A gene delivery circuit is established, whereby liquid containing a gene vector is then provided to the aortic root via the HEARTPORT® Endoaortic Clamp™ catheter, flow through the coronary arteries and the coronary veins into the coronary sinus, and thence into the HEARTPORT® Endocoronary Sinus™ catheter for return to the gene delivery circuit. The gene delivery circuit may be operated by gravity (e.g. a reservoir containing the liquid suspended over the subject) or by a pump. When the gene delivery circuit is pump-driven, it may be a single-pass system, or a circulating system, whereby liquid recovered by the HEARTPORT® Endocoronary Sinus™ catheter is returned to the aortic root. The liquid may further contain one or more inflammatory mediators, as described herein.

It is understood that there are significant drawbacks to this procedure (i.e. using the HEARTPORT® equipment). Not all blood that is supplied to the coronary arteries is returned to the right atrium by way of the coronary sinus. About five percent of this blood flows into the right atrium and right ventricle by way of passageways designated 'Thebesian vessels.' Thus, according to this method, a portion of the liquid supplied to the aortic root by the gene delivery circuit mixes with venous blood in the right atrium and right ventricle, and is thereby mixed with blood that is provided systemically by the cardiac bypass circuit. Mixing of liquid from the gene delivery circuit with venous blood of the cardiac bypass circuit cannot be minimized by withdrawing fluid from the HEARTPORT® Endopulmonary Vent™ catheter, whereby venous blood mixed with gene delivery circuit liquid is withdrawn from the pulmonary artery and the right ventricle. Of course, venous blood withdrawn through this catheter must be replaced by providing additional blood to the cardiac bypass circuit. Thus, given quantity of blood which would need to be replaced, this method is not practical. Because at least one catheter (i.e. the HEARTPORT® Endocoronary Sinus™ catheter), and preferably a second (i.e. the HEARTPORT® Endopulmonary Vent™ catheter) must traverse one arm of the vena cava and the right atrium, occlusion of either the vena cava or the right atrium is not practical using the HEARTPORT® equipment. Of course, either or both of the HEARTPORT® catheters could be inserted through purse-string sutures in the wall of the right atrium, but this would require sternotomy of the subject, thereby destroying the minimally invasive character of the method.

A further drawback of the procedure involving the HEARTPORT® equipment is that endocoronary sinus catheters reduce coronary blood flow in the heart. Numerous coronary veins open into the coronary sinus at or very near the ostium of the coronary sinus. Emplacement of a catheter with in the endocoronary sinus involves inflation of a balloon or similar device within the sinus, and the balloon must be seated against the ostium in order to occlude blood flow therethrough. However, seating a balloon against the ostium occludes coronary veins which open into the coronary sinus at or near the ostium, thereby preventing or reducing coronary blood flow through those veins. When an agent (e.g. a gene vector) is to be delivered to myocardial tissue by way of those veins, delivery of the agent to myocardium associated with those veins is inhibited or prevented. Therefore, the use of an endocoronary sinus catheter inhibits delivery of agents to at least a portion of myocardial tissue, and is preferably avoided. The procedure involving the HEARTPORT® equipment relies on use of an endocoronary sinus catheter, and is therefore not favored.

An alternate minimally invasive procedure may be used which does not have the drawbacks of the procedure described above (i.e. using the HEARTPORT® equipment). In this alternate method, the HEARTPORT® Endopulmonary Vent™ catheter and the HEARTPORT® Endocoronary Sinus™ catheter are replaced by a multi-functional venous return cannula (herein alternately designated a "cardiac isolation catheter"). The cardiac isolation catheter is inserted through the inferior and superior vena cavae, has vessel seats (e.g. balloons or raised portions) which can be used to occlude the inferior and superior vena cavae, and has a venous blood flow lumen which is in fluid communication with at least a pair of ports, at least one port being located superior to the vessel seat in the superior vena cava, and at least one port being located inferior to the vessel seat in the inferior vena cava. Once the vena cavae are occluded by seating them against the vessel seats, venous blood flow through both vena cavae passes through the venous blood flow lumen of the cardiac isolation catheter.

Figure 15:
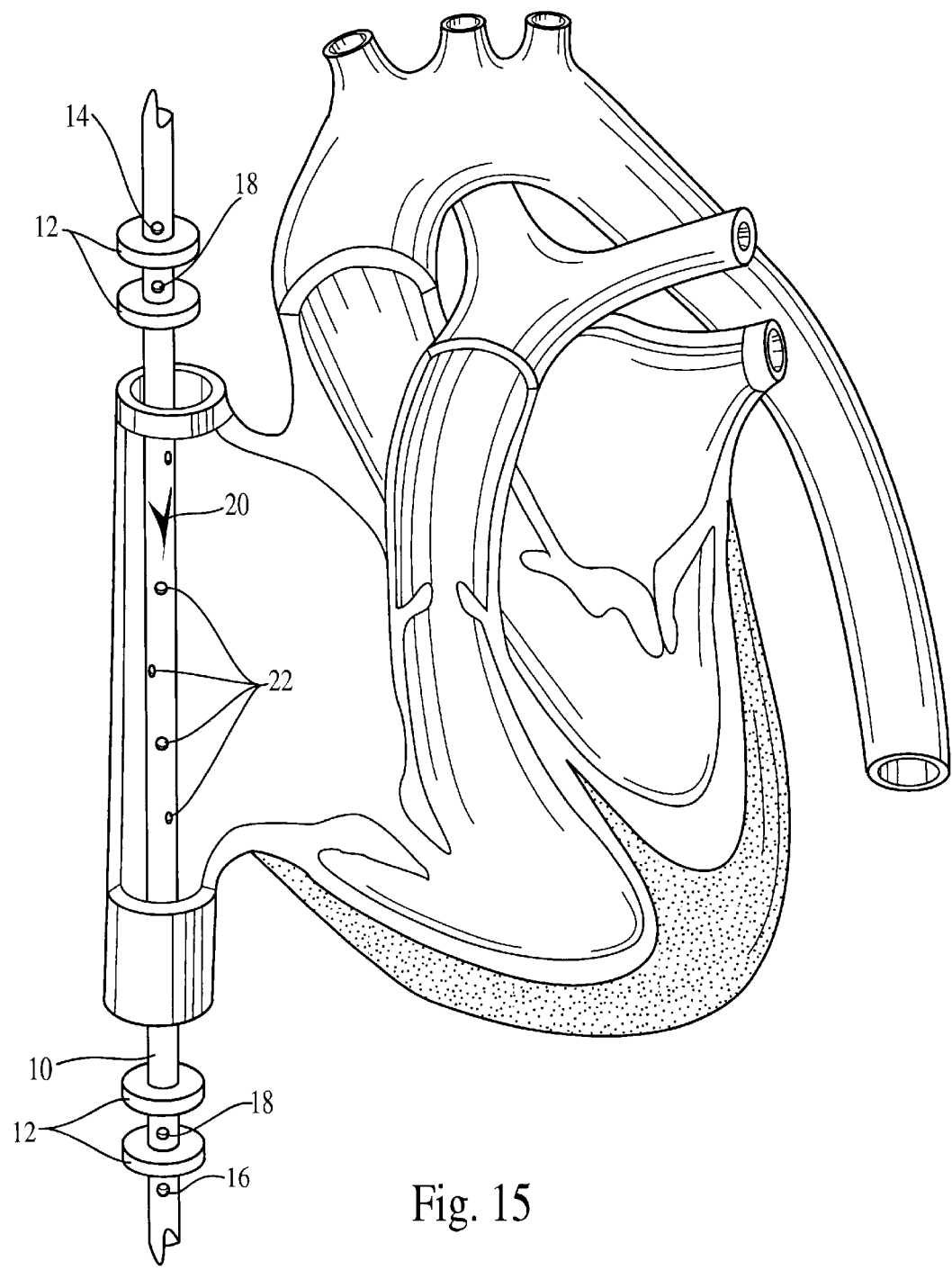
FIG. 15 depicts a human heart having a cardiac isolation catheter threaded through the vena cava associated therewith, as described herein.
Figure 16A:
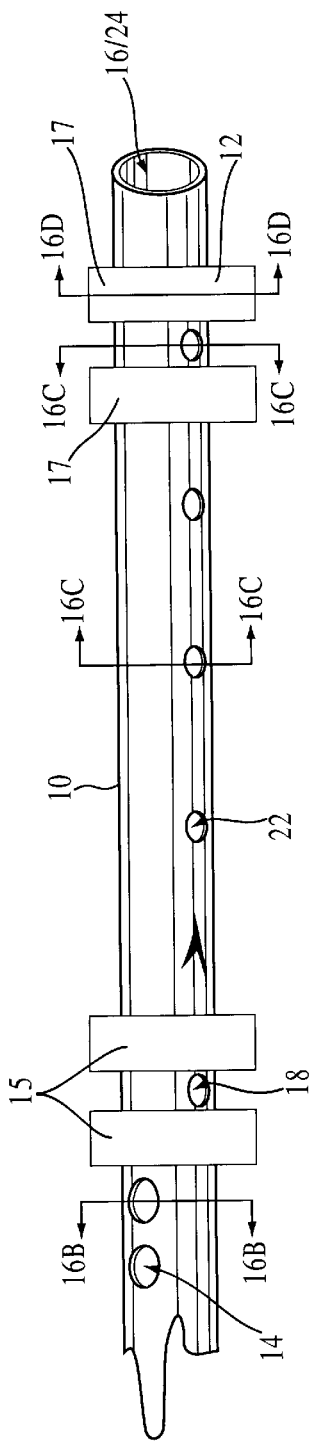
FIGS. 16A, 16B, 16C, and 16D, is a quartet of diagrams which depict the structure of one embodiment of the cardiac isolation catheter of the invention.
Figure 16D:
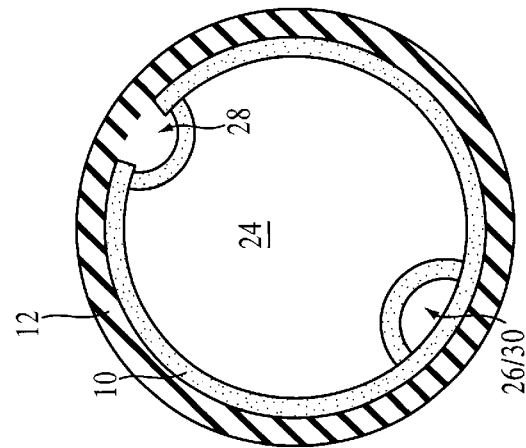
Figure 16C:
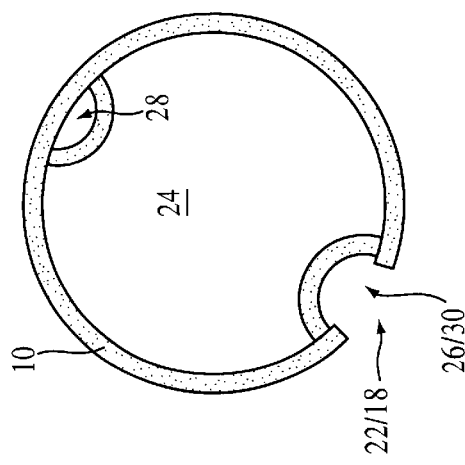
Figure 16B:
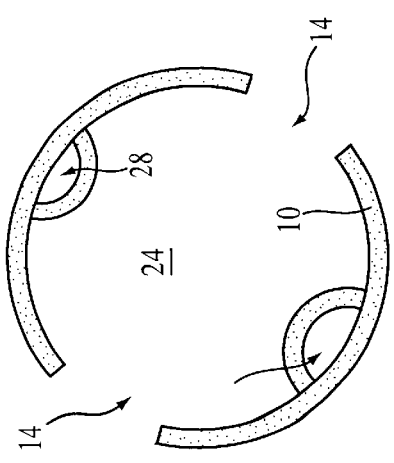

Alternate embodiments of the cardiac isolation catheter are depicted in FIGS. 15 and 16A. In FIG. 15, both the proximal port 14 and the distal port 16 are radial holes through the catheter body 10 which communicate with the venous blood flow lumen (not shown in FIG. 15). In FIG. 16A, the distal port 16 is merely an opening at the distal end of the catheter body 10 that is a continuation of the venous blood flow lumen 24. As indicated in FIG. 15, the vena cavae may be occluded by inflating the balloons 12 of the catheter without occluding blood flow from the superior portion of the superior vena cava into the proximal port 14 or from the inferior portion of the inferior vena cava into the distal port 16. The venous blood flow lumen of the cardiac isolation catheter may be connected to the venous limb of an extracorporeal pump/oxygenator apparatus as part of a cardiac bypass circuit.

As indicated in FIGS. 15 and 16, the cardiac isolation catheter may further comprise one or more access ports 20, one or more right atrium fluid access ports 22 located between the distal vessel seat 17 and proximal vessel seat 15, and one or more suction ports 18. The right atrium fluid access ports 22 communicate with one or more fluid flow lumens 30, through which fluid may be recovered from the right atrium. Preferably, at least gentle suction (i.e. −0.1 to −5 psig) is applied to the fluid flow lumen 30 in order to enhance fluid uptake from the right atrium. The suction ports 18 communicate with one or more suction lumens 26, which may optionally be the same as a fluid flow lumen 30, as in FIG. 16. Providing at least gentle suction (i.e. −0.1 to −5 psig) to the suction lumen(s) 26 may enhance seating of the vena cavae in the vessel seats (e.g. the pairs of balloons 12 in FIGS. 15 and 16). The access ports 20 may communicate with a lumen dedicated to the access port 20 or with one of the other lumens of the cardiac isolation catheter (e.g. the venous blood flow lumen 24, the suction lumen 26, or the fluid flow lumen 30). The access ports 20 are included in order to provide an orifice through which compositions, catheters, or other devices may be inserted in the region of the right atrium of the subject (e.g. as in FIG. 17A).

The cardiac isolation catheter may be threaded through the vena cava in either a superior-to-inferior direction or in the reverse (i.e. inferior-to-superior) direction. When the catheter is inserted in the superior-to-inferior direction, it is preferably inserted into a human subject thorough the right jugular vein, although it may be inserted through the left jugular vein or through another vein which communicates with the superior vena cava. When the catheter is inserted in the inferior-to-superior direction, it is preferably inserted into a human subject thorough a femoral vein of the subject, although it may be inserted through another vein which communicates with the inferior vena cava. Alternately, the catheter may be threaded entirely through the subject (e.g. extending from both the subject's femoral vein and the subject's jugular vein). Flexibility in the orientation in which the catheter may be inserted is advantageous, in that the venous anatomy of all patients varies to some degree, and, in some cases, may preclude insertion of the catheter in one orientation. In such cases, the catheter may be inserted from another location, in the same or a different orientation. This flexibility is an important aspect of the catheter.

Regardless of the orientation of the cardiac isolation catheter, it is used in substantially the same way, as follows.

The cardiac isolation catheter is threaded through the superior and inferior vena cavae of the subject, such that the distal vessel seat 17 is in on of the superior and inferior vena cavae and the proximal vessel seat 15 is in the other. The catheter is then secured in place. Preferably, the vessel seat in the superior vena cava is situated between the right atrium and the junction of the brachiocephalic veins and the vessel seat in the inferior vena cava is situated between the right atrium and the junction of the hepatic veins with the inferior vena cava. The vessel seats 15 and 17 may be, for example, balloons 12, raised portions of the catheter body 10, expandable portions of the catheter body 10, indentations into the catheter body 10, rough or irregular portions of the catheter body 10, or the like. The cardiac isolation catheter may also comprise one or more suction ports associated with a vessel seat, whereby upon application of suction to the suction port, the wall of a vena cava is caused to seat more firmly against the vessel seat. The important characteristic of the vessel seats is that they provide a support by which, either independently or in cooperation with an extravascular element (e.g. a snare or clamp), the cardiac isolation catheter may be secured in place within the vena cavae of the subject.

An endoaortic catheter is threaded through an artery of the subject and into the ascending aorta, as depicted in FIG. 18. The endoaortic catheter comprises a flexible rod 50 and an aortic vessel seat 52. The rod 50 has a distal end and a distal tip, and there is a discharge port 55 in the distal end, distally located with respect to the aortic vessel seat. The rod optionally has a left ventricle vent port 57 located at or near the distal end of the rod. The discharge port 55 and the left ventricle vent port 57 may optionally be the same port, in which case the fluid feed to the discharge port 55 is fitted with a pressure relief device in order to prevent pressure build-up within the left ventricle and aortic root. The discharge port 55 of the endoaortic catheter is in fluid communication with a liquid access lumen 54 which extends longitudinally in the endoaortic catheter. Thus, liquid provided to the liquid access lumen 54 can flow through the length of the endoaortic catheter and exit the catheter at the discharge port 55. The aortic vessel seat may be any device attached to, surface feature of, or surface treatment of the endoaortic catheter which serves to secure the endoaortic catheter in place within the aorta of the subject. For example, any of the vessel seats described for use with the cardiac isolation catheter may be used with the endoaortic catheter. Seating the aorta against the aortic vessel seat occludes fluid flow past the aortic vessel seat within the aorta. The endoaortic catheter may, for example, be a commercially available catheter such as the HEARTPORT® Endoaortic Clamp™ catheter described herein.

The distal end of endoaortic catheter is placed within the aortic root or within the left ventricle, and the aorta is seated against the aortic vessel seat between the coronary arteries and the arch of the aorta. One appropriate arrangement of the endoaortic catheter is depicted herein in FIG. 18. In this Figure, the discharge port 55 is present in the left ventricle and fluid flow through the aorta is occluded by seating the aorta against the aortic vessel seat 12, in this case an endoaortic balloon.

The fluid flow lumen 30 of the cardiac isolation catheter is placed in fluid communication of with the venous limb of an extracorporeal fluid flow circuit. The arterial limb of this fluid flow circuit is connected with the fluid access lumen 54 of the endoaortic catheter. The fluid flow circuit may comprise, for example, a reservoir containing a gene vector, a pump, a fluid, and a fluid oxygenator. The fluid may be substantially any fluid which may be provided to the interior of the subject's heart or cardiac blood vessels without causing serious harm thereto. By way of example, the fluid may be phosphate buffered saline or another buffer, blood obtained from the subject or from a donor, a oxygen-transporting agent, a perfluorochemical liquid, or the like. The fluid may also, as described herein, comprise one or more inflammatory mediators including, but not limited to, a vascular permeability-enhancing agent such as histamine, and a vasodilator such as papaverine.

The non-cardiac tissues of the subject are perfused by obtaining systemic venous blood from the subject by way of the venous blood flow lumen 24 of the cardiac isolation catheter, oxygenating this blood using an extracorporeal blood oxygenator, and providing the oxygenated blood to an artery of the subject using, for example, a femoral artery catheter. This systemic blood oxygenation methodology is illustrated in FIG. 19A. Alternately, the endoaortic catheter may have an oxygenated blood flow lumen and an oxygenated blood outlet near the distal end thereof, but proximally located with respect to the aortic vessel seat. Providing oxygenated blood to the oxygenated blood flow lumen causes the oxygenated blood to flow in the subject's arteries beginning from a point near the aortic arch, which may provide blood supply that is more similar to normal physiological blood supply than flow induced by providing blood at any other point in the subject.

Once the cardiac isolation catheter is secured in place in the vena cavae of the subject, a second catheter having a distal end may be threaded through a lumen of the cardiac isolation catheter, through an access port 20 which communicates with that lumen, and thereby into the right atrium of the subject. The second catheter may be advanced through the tricuspid valve, into the root of the pulmonary artery, or even beyond the pulmonary valve, in order to minimize or prevent passive flow of blood from the interior of the heart into the pulmonary artery. The second catheter may have a balloon 42 or other vessel-occluding device on or near the distal end thereof, as illustrated in FIG. 17A. The second catheter may also have a fluid uptake port in either or both of its distal end or in a curved portion which may be advanced into the right ventricle, wherein fluid from the pulmonary artery or the right ventricle may be taken up through a fluid uptake lumen which extends longitudinally in the second catheter and which communicates with the opening. This fluid withdrawal may be useful to prevent systemic, pulmonary, or other damage which might be caused by inflammatory mediator(s) which accumulate in the left ventricle or proximal to the pulmonary valve.

All of the catheters described herein may be emplaced under fluoroscopic, radiographic, endotracheal echocardiographic, or sonographic techniques, as is well known in the art. In order to facilitate such placement, one or more sonographically opaque, radiographically opaque, or otherwise detectable markers may be incorporated onto or into the catheters. Such markers are well known in the art.

Once the cardiac isolation catheter, the second catheter, and the endoaortic catheter have been emplaced (e.g. as in FIGS. 17 and 18) and the azygous vein has been occluded, if necessary, fluid flow through the isolated cardiac circulation may be initiated. Fluid may be provided through the liquid access lumen 54 and discharge port 55 of the endoaortic catheter, either at or slightly (e.g. 0.1 to 5 psig) above atmospheric pressure or at significantly increased pressure, as described elsewhere herein. The fluid provided to the isolated cardiac circulation may, for example, be synthetic (e.g. a perfluorochemical liquid or a buffer such as Tris-Cl at pH 7.4), naturally occurring (e.g. the subject's blood), or a combination thereof (e.g. blood supplemented with a buffer). The fluid may be provided to the cardiac circulation in a single pass (i.e. fluid is discarded after exiting the cardiac circulation) or in a circulating mode (i.e. whereby fluid exiting the cardiac circulation is re-supplied to the cardiac circulation). The duration of the period during which isolated cardiac circulation is maintained may be increased if the liquid provided to the isolated cardiac circulation contains an oxygen-transporting agent, such as red blood cells or a perfluorochemical liquid. The liquid provided to the isolated cardiac circulation may initially contain an inflammatory mediator such as histamine or papaverine, or such mediators may be added to the liquid after fluid flow to the isolated cardiac circulation has begun. Likewise, this liquid may initially comprise a gene vector, or the gene vector may be added after isolated cardiac circulation has begun.

Prior to recombining cardiac and systemic circulations, it may be desirable to flush any free gene vector(s) or inflammatory mediator(s) from the isolated cardiac circulation in order to prevent undesirable systemic exposure to these components. Such components may be flushed from the circulation by providing a liquid that is free of the components to the liquid access lumen of the endoaortic catheter. At least a few cardiac circulation volumes should be passed through the isolated cardiac circulation prior to merging the cardiac and systemic circulations. By way of example about 0.5 to 1 liter of liquid may be flushed through the cardiac circulation of a human subject.

If inflammatory mediators have been provided to the isolated cardiac circulation, then it is advisable that extracorporeal circulatory support be provided to the subject, as described elsewhere herein.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A cardiac isolation catheter insertable within the vena cava of a mammal, the catheter comprising
   (a) a hollow tubular body having a venous blood flow lumen extending longitudinally therein, a proximal end, a distal end, a proximal port, and a distal port;
   (b) a distal vessel seat attached to the body; and
   (c) a proximal vessel seat attached to the body;
   wherein the body has an access lumen extending longitudinally therein that communicates with an access port positioned on the body between the distal vessel seat and the proximal vessel seat and that is adapted to accommodate passage of a second catheter therethrough,
   wherein the cardiac isolation catheter is positionable within the vena cava of the mammal such that one vessel seat is positioned in the superior vena cava of the mammal between the right atrium and the junction of the brachiocephalic veins and the other vessel seat is positioned in the inferior vena cava between the right atrium and the hepatic veins, wherein the distal port is located distally with respect to the distal vessel seat, wherein the proximal port is located proximally with respect to the proximal vessel seat, wherein at least one of the distal vessel seat and the proximal vessel seat comprises a pair of closely-spaced raised surfaces, and wherein the body has a suction lumen extending longitudinally therein and communicating with a suction port situated between the pair of closely-spaced raised surfaces, whereby the vena cava may be securely seated at the vessel seat by application of suction to the suction lumen and blood in the junction of the brachiocephalic veins and blood in the hepatic veins is in fluid communication with the venous blood flow lumen by way of the ports.

* * * * *